(12) United States Patent
Bousquet-Gagnon et al.

(10) Patent No.: US 7,307,148 B2
(45) Date of Patent: Dec. 11, 2007

(54) METHOD FOR PURIFICATION OF ALBUMIN CONJUGATES

(75) Inventors: Nathalie Bousquet-Gagnon, St-Jérôme (CA); Omar Quraishi, Hudson (CA); Dominique P. Bridon, San Francisco, CA (US)

(73) Assignee: ConjuChem Biotechnologies Inc., Montreal (Quebec) (CA)

( * ) Notice: Subject to any disclaimer, the term of this patent is extended or adjusted under 35 U.S.C. 154(b) by 0 days.

(21) Appl. No.: 11/112,277

(22) Filed: Apr. 22, 2005

(65) Prior Publication Data

US 2005/0267293 A1 Dec. 1, 2005

Related U.S. Application Data

(60) Provisional application No. 60/565,228, filed on Apr. 23, 2004.

(51) Int. Cl.
*C07K 1/00* (2006.01)
(52) U.S. Cl. ...................................... 530/364
(58) Field of Classification Search ................ 514/12; 530/350
See application file for complete search history.

(56) References Cited

U.S. PATENT DOCUMENTS

| | | | |
|---|---|---|---|
| 4,206,199 A | 6/1980 | Fujino et al. | |
| 4,251,631 A | 2/1981 | Simon | |
| 4,423,034 A | 12/1983 | Nakagawa et al. | |
| 4,462,941 A | 7/1984 | Lee et al. | |
| 4,678,671 A * | 7/1987 | Feijen et al. ............... | 424/443 |
| 4,745,100 A | 5/1988 | Gilbard et al. | |
| 4,766,106 A | 8/1988 | Katre et al. | |
| 4,859,604 A | 8/1989 | Gould et al. | |
| 4,902,505 A | 2/1990 | Pardridge et al. | |
| 5,103,233 A | 4/1992 | Gallagher et al. | |
| 5,118,666 A | 6/1992 | Habener | |
| 5,120,712 A | 6/1992 | Habener | |
| 5,424,286 A | 6/1995 | Eng | |
| 5,493,007 A | 2/1996 | Burnier et al. | |
| 5,545,618 A | 8/1996 | Buckley et al. | |
| 5,574,008 A | 11/1996 | Johnson et al. | |
| 5,580,853 A | 12/1996 | Sytkowski | |
| 5,612,034 A | 3/1997 | Pouletty et al. | |
| 5,612,458 A | 3/1997 | Hyldig-Nielsen et al. | |
| 5,614,487 A | 3/1997 | Battersby et al. | |
| 5,614,492 A | 3/1997 | Habener | |
| 5,654,276 A | 8/1997 | Barrett et al. | |
| 5,705,483 A | 1/1998 | Galloway et al. | |
| 5,725,804 A | 3/1998 | Yen | |
| 5,770,570 A | 6/1998 | Paul et al. | |
| 5,807,827 A | 9/1998 | Lee et al. | |
| 5,840,733 A | 11/1998 | Krantz et al. | |
| 5,843,440 A | 12/1998 | Pouletty et al. | |
| 5,855,866 A | 1/1999 | Thorpe et al. | |
| 5,869,602 A | 2/1999 | Jonassen et al. | |
| 5,874,408 A | 2/1999 | Nayar | |
| 5,939,390 A | 8/1999 | Flodgaard et al. | |
| 5,942,620 A | 8/1999 | Krantz et al. | |
| 5,958,909 A | 9/1999 | Habener | |
| 5,981,488 A | 11/1999 | Hoffmann | |
| 6,005,081 A * | 12/1999 | Burton et al. ............... | 530/399 |
| 6,006,753 A | 12/1999 | Efendic | |
| 6,087,375 A | 7/2000 | Bridon et al. | |
| 6,103,233 A | 8/2000 | Pouletty et al. | |
| 6,107,489 A | 8/2000 | Krantz et al. | |
| 6,133,235 A | 10/2000 | Galloway et al. | |
| 6,191,102 B1 | 2/2001 | DiMarchi et al. | |
| 6,268,343 B1 | 7/2001 | Knudsen et al. | |
| 6,277,583 B1 | 8/2001 | Krantz et al. | |
| 6,277,819 B1 | 8/2001 | Efendic | |
| 6,277,863 B1 | 8/2001 | Krantz et al. | |
| 6,284,725 B1 | 9/2001 | Coolidge et al. | |
| 6,329,336 B1 | 12/2001 | Bridon et al. | |
| 6,403,324 B1 | 6/2002 | Krantz et al. | |
| 6,437,092 B1 | 8/2002 | Ezrin et al. | |
| 6,440,417 B1 | 8/2002 | Thibaudeau et al. | |
| 6,500,918 B2 | 12/2002 | Ezrin et al. | |
| 6,506,724 B1 | 1/2003 | Hiles et al. | |
| 6,514,500 B1 | 2/2003 | Bridon et al. | |
| 6,528,486 B1 | 3/2003 | Larsen et al. | |
| 6,583,111 B1 | 6/2003 | DiMarchi et al. | |
| 6,593,295 B2 | 7/2003 | Bridon et al. | |

(Continued)

FOREIGN PATENT DOCUMENTS

EP 0602290 6/1994

(Continued)

OTHER PUBLICATIONS

U.S. Appl. No. 09/623,533, filed Sep. 5, 2000, Boudjellab et al.

(Continued)

*Primary Examiner*—Karen Cochrane Carlson
*Assistant Examiner*—Agnes B. Rooke
(74) *Attorney, Agent, or Firm*—Jones Day

(57) ABSTRACT

The present invention relates to a method for separating albumin conjugate from unconjugated albumin in a solution comprising albumin conjugate and unconjugated albumin by loading the solution onto a hydrophobic support equilibrated in aqueous buffer having a high salt content; applying to the support a gradient of decreasing salt concentration; and collecting the eluted albumin conjugate.

28 Claims, 76 Drawing Sheets

U.S. PATENT DOCUMENTS

| | | |
|---|---|---|
| 6,602,981 B2 | 7/2003 | Ezrin et al. |
| 6,610,825 B2 | 8/2003 | Ezrin et al. |
| 6,660,716 B1 | 12/2003 | Yakuba-Madus et al. |
| 6,703,359 B1 | 3/2004 | Young et al. |
| 6,706,689 B2 | 3/2004 | Coolidge et al. |
| 6,706,892 B1 | 3/2004 | Ezrin et al. |
| 6,723,530 B1 | 4/2004 | Drucker |
| 6,767,887 B1 | 7/2004 | Hoffmann et al. |
| 6,821,949 B2 | 11/2004 | Colrain et al. |
| 6,849,714 B1 | 2/2005 | Bridon et al. |
| 6,858,576 B1 | 2/2005 | Young et al. |
| 6,861,236 B2 | 3/2005 | Moll et al. |
| 6,872,700 B1 | 3/2005 | Young et al. |
| 6,887,470 B1 | 5/2005 | Bridon et al. |
| 6,887,849 B2 | 5/2005 | Bridon et al. |
| 6,894,024 B2 | 5/2005 | Coolidge et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,989,366 B2 | 1/2006 | Beeley et al. |
| 6,998,387 B1 | 2/2006 | Goke et al. |
| 7,090,851 B1 | 8/2006 | Bridon et al. |
| 7,105,508 B1 | 9/2006 | Kling et al. |
| 7,112,567 B2 | 9/2006 | Bridon et al. |
| 7,144,854 B1 | 12/2006 | Bridon et al. |
| 7,166,695 B2 | 1/2007 | Krantz et al. |
| 2001/0018421 A1 | 8/2001 | Ezrin et al. |
| 2001/0047084 A1 | 11/2001 | Knudsen et al. |
| 2002/0009441 A1 | 1/2002 | Pouletty et al. |
| 2002/0018751 A1 | 2/2002 | Bridon et al. |
| 2002/0039999 A1 | 4/2002 | Ezrin et al. |
| 2002/0049153 A1 | 4/2002 | Bridon et al. |
| 2003/0073630 A1* | 4/2003 | Bridon et al. ................. 514/12 |
| 2003/0108567 A1 | 6/2003 | Bridon et al. |
| 2003/0108568 A1 | 6/2003 | Bridon et al. |
| 2003/0170250 A1 | 9/2003 | Ezrin et al. |
| 2003/0232754 A1 | 12/2003 | Holst et al. |
| 2004/0053819 A1 | 3/2004 | Dodd et al. |
| 2004/0127398 A1 | 7/2004 | Bridon et al. |
| 2004/0138100 A1 | 7/2004 | Bridon et al. |
| 2004/0156859 A1 | 8/2004 | Ezrin et al. |
| 2004/0248782 A1 | 12/2004 | Bridon et al. |
| 2004/0266673 A1 | 12/2004 | Bakis et al. |
| 2005/0037974 A1 | 2/2005 | Krantz et al. |
| 2005/0065075 A1 | 3/2005 | Erickson et al. |
| 2005/0070475 A1 | 3/2005 | Bridon et al. |
| 2005/0176641 A1 | 8/2005 | Bakis et al. |
| 2005/0176643 A1 | 8/2005 | Bridon et al. |
| 2005/0187159 A1 | 8/2005 | Bridon et al. |
| 2005/0267293 A1 | 12/2005 | Bousquet-Gagnon et al. |
| 2006/0009377 A1 | 1/2006 | Bridon et al. |
| 2006/0058235 A1 | 3/2006 | Bridon et al. |
| 2006/0063699 A1 | 3/2006 | Larsen |
| 2006/0069029 A1 | 3/2006 | Kolterman et al. |
| 2006/0135426 A1 | 6/2006 | Bridon et al. |
| 2006/0135428 A1 | 6/2006 | Bridon et al. |
| 2006/0217304 A1 | 9/2006 | Bridon et al. |
| 2006/0233707 A1 | 10/2006 | Kratz |
| 2006/0252916 A1 | 11/2006 | DiMarchi et al. |

FOREIGN PATENT DOCUMENTS

| | | |
|---|---|---|
| EP | 0969016 | 1/2000 |
| WO | WO 93/25579 | 12/1993 |
| WO | WO-95/10302 | 4/1995 |
| WO | WO 96/06626 | 3/1996 |
| WO | WO-97/25074 | 7/1997 |
| WO | WO-97/29372 | 8/1997 |
| WO | WO-98/00171 | 1/1998 |
| WO | WO 98/11126 | 3/1998 |
| WO | WO-99/24074 | 5/1999 |
| WO | WO-99/24075 | 5/1999 |
| WO | WO-99/24076 | 5/1999 |
| WO | WO-99/24462 | 5/1999 |
| WO | WO-99/48536 | 9/1999 |
| WO | WO 99/048536 | 9/1999 |
| WO | WO-00/69900 | 11/2000 |
| WO | WO 00/069902 | 11/2000 |
| WO | WO 00/070665 | 11/2000 |
| WO | WO 00/076550 | 12/2000 |
| WO | WO 03/097693 | 11/2003 |

OTHER PUBLICATIONS

U.S. Appl. No. 09/623,543, filed Sep. 5, 2000, Beliveau et al.
U.S. Appl. No. 09/657,336, filed Sep. 7, 2000, Boudjellab et al.
U.S. Appl. No. 09/657,431, filed Sep. 7, 2000, Beliveau et al.
U.S. Appl. No. 11/040,810, filed Jan. 21, 2005, Bakis et al.
U.S. Appl. No. 11/066,697, filed Feb. 25, 2005, Bridon et al.
U.S. Appl. No. 11/067,556, filed Feb. 25, 2005, Bidon et al.
Dias-Cabral, A.C. et al. (2003) "Effect of salts and temperature on the adsorption of bovine serum albumin on polypropylene glycol-Sepharose under linear and overloaded chromatographic conditions," Journal of Chromatography, 1018: 137-153.
Holmes, Darren L. et al. (2000) "Site Specific 1:1 Opoid:Albumin conjugate with in Vitro Activity and Long in Vivo Duration," Bioconjugate Chemistry, 11(4): 439-444.
Jette, Lucie et al. (2005) "Human Growth Hormone-Release Factor (hGRF)1-29- Albumin Bioconjugates Activate the GRF Receptor on the Anterior Pituitary in Rats: Indentification of CJC-1295 as a Long-Lasting GRF Analog," Endocrinilogy, 146(7): 3052-3058.
Leger, Roger et al. (2003) "Synthesis and in Vitro Analysis of Atrial Natriuretic Peptide-Albumin Conjugates," Bioorganic & Medicinal Chemistry Letters 13: 3571-3575.
Leger, Roger et al. (2004) "Identification of CJC-1131-albumin bioconjugate as a stable and bioactive GLP-1(7-36) analog," Bioorganic & Medicinal Chemistry Letters, 14: 4395-4398.
Mariani, Massimo et al. (Sep. 1998) "A Competitive Enzyme-Linked Immunosorbent Assay for Measuring the Levels of Serum Antibody to Haemophilus influenzae Type b," Clinical and Diagnostic Laboratory Immunology, 5(5): 667-674.
Thibaudeau, Karen et al. (2005) "Synthesis and Evaluation of Insulin—Human Serum Albumin Conjugates," Bioconjugate Chem., 16: 1000-1008.
U.S. Appl. No. 09/623,533, filed Sep. 5, 2000, Bridon et al.
U.S. Appl. No. 09/623,543, filed Sep. 5, 2000, Bridon et al.
Akil et al., "Endogenous Opioids: Biology and Function," Ann. Rev. Neurosci., 7:223-255 (1984).
Barragan et al., "Interactions of exendin-(9-39) with the Effects of Glucagon-like Peptide-1-(7-36) Amide and of Exendin-4 on Arterial Blood Pressure and Heart Rate in Rats," Regulatory Peptides, 67:63-68 (1996).
Bell et al., "Hamster Preproglucagon Contains the Sequence of Glucagon and Two Related Peptides," Nature, 302:716-718 (1983).
Benhar et al., "Pseudomonas Exotoxin A Mutants," J. Biol. Chem., 269(18):13398-13404 (1994).
Bergmann et al., "Cationized Serum Albumin Enhances Response of Cultured Fetal Rat Long Bones to Parathyroid Hormone," Endocrinology, 116(5):1729-1733 (1985).
Bhargava et al., "Immobilization of Active Urokinase on Albumin Microspheres: Use of a Chemical Dehydrant and Process Monitoring," Pharmaceutical Research, 9(6):776-781 (1992).
Breton et al., "Prolonged Half-Life in the Circulation of a Chemical Conjugate Between a Pro-Urokinase Derivative and Human Serum Albumin," Eur. J. Biochem., 231(3):563-569 (1995).
Calara et al., "A Randomized, Open-Label, Crossover Study Examining the Effect of Injection Site on Bioavailability of Exentide (Synthetic Exendin-4)," Clin. Ther., 27(2):210-214 (2005).
Davis et al., "Reduction of immunogenicity and Extension of Circulating Half-Life of Peptides Proteins," Peptide and Protein Drug Delivery, Lee, V. H. L., ed., Marcel Dekker, Inc., NY, NY; 831-864 (1991).

Delgado et al., "The Uses and Properties of PEG-Linked Proteins," Critical Reviews in Therapeutic Drug Carrier Systems, 9(3,4):249-304 (1992).

Drucker, "Perspectives in Diabetes," Diabetes, 47(2):159-169 (Feb. 1998).

Edwards et al., "Glucagon-like Peptide 1 Has a Physiological Role in the Control of Postprandial Glucose in Humans," Diabetes, 48:86-93 (1999).

Edwards et al., "Exendin-4 Reduces Fasting and Postprandial Glucose and Decreases Energy Intake in Healthy Voluneers," Am. J. Physiol. Endocrinol. Metab., 281:E155-E161 (2001).

Eng et al., "Prolonged Effect of Exendin-4 on Hyperglycemia of db/db Mice," J. Biol. Chem., 267(11):7402-7405 (1992).

Eng, "Isolation and Characterization of Exendin-4, an Exendin-3 Analogue, from *Heloderma suspecum* Venom," Diabetes, 45:152A (abstract 554) (1996).

Foa et al., "Glucagon and Other Products of the Proglucagon Gene: Physiology and Possible Role in the Pathogenesis of Disease," Giornale Italiano Di Diabetologia, 11:(Supplemental)1-42 (1991).

Francis et al., "PEGylation of Cytokines and other Therapeutic Proteins and Peptides: The Importance of Biological Optimisation of Coupling Techniques," International Journal of Hematology, 68:1-18 (1998).

Gombotz et al., "Biodegradable Polymers for Protein and Peptide Drug Delivery," Bioconjug. Chem., 6:332-351 (1995).

Goodson et al., "Site-Directed Pegylation of Recombinant Interleukin-2 at Its Glycosylation Site," Bio/Technology, 8:343-346 (1990).

Goosen, "Optimization of Microencapsulation Parameters: Semipermeable Microcapsules as a Bioartificial Pancreas," Biotechnology and Bioengineering, XXVII:146-150 (1985).

Heinrich et al., "Pre-proglucagon Messenger Ribonucleic Acid: Nucleotide and Encoded Amino Acid Sequences of the Rat Pancreatic Complementary Deoxyribonucleic Acid," Endocrinology, 115:2176-2181 (1984).

Hirai et al., "A New Mast Cell Degranulating Peptide "mastoparan" in the Venom of *Vespula lewisii*," Chem. Pharm. Bull., 27(8):1942-1944 (1979).

Hupe-Sodmann et al., "Endoproteolysis of Glucagon-like Peptide (GLP)-1(7-36) amide by Ectopeptidases in RINm5F Cells," Peptides, 18(5):625-632 (1997).

Ishikawa et al., "Enzyme-Labeling with Maleimides and Its Application to the Immunoassay of Peptide Hormones," Enzyme-Labeled Immunoassay of Hormones and Drugs, Walter deGruyter & Co., Berlin, New York, pp. 43-57 (Oct. 7, 1978).

Isoai et al., "A Potent Anti-Metastatic Activity of Tumor Invasion-Inhibiting Factor-2 and Albumin Conjugate," Biochem. Biophys. Res. Commun., 192(1):7-14 (1993).

Kapas et al., "Cloning and Expression of cDNA Encoding a Rat Adrenomedullin Receptor," J. Biol. Chem., 270(43):25344-25347 (1995).

Knusli et al., "Polyethylene Glycol (PEG) Modification of Granulocyte Macrophage Colony Stimulating Factor (GM-CSF) Enhances Neutrophil Priming Activity but not Colony Stimulating Activity," British Journal of Haematology, 82:654-663 (1992).

Kolodny et al., "A Conjugation of Synthetic Peptides to Proteins: Quantitation from S-Carboxymethylcysteine Released Upn Acid Hydrolysis," Analytical Biochemistry, 187:136-140 (1990).

Lopez et al., "Mammalian Pancreatic Preproglucagon Contains Three Glucagon-related Peptides," Proc. Natl. Acad. Sci. USA, 80:5485-5489 (1983).

Mao et al., "Superoxide Dismutase: Improving Its Pharmacological Properties by Conjugation with Human Serum Albumin," Biomat. Art. Cells, Art. Org., 17(3):229-244 (1989).

Marburg et al., "Introduction of the Maleimide Function onto Resin-Bound Peptides: A Simple, High Yield Process Useful for Discriminating among Several Lysines," Bioconjug. Chem., 7:612-616 (1996).

Meurer et al., "Properties of Native and In Vitro Glycosylated Forms of the Glucagon-like Peptide-1 Receptor Antagonist Exendin (9-39),"Metabolism, 48(6):716-724 (1999).

Mumby et al., "Antisera of Designed Specificity for Subunits of Guanine Nucleotide-binding Regulatory Proteins," Proc. Natl. Acad. Sci., 83:265-269 (1986).

Oren et al., "Mode of Action of Linear Amphipathic α-Helical Antimicrobial Peptides," Biopolymers (Peptide Science), 47:451-463 (1998).

Paige et al., "Prolonged Circulation of Recombinant Human Granulocyte-Colony Stimulating Factor by Covalent Linkage to Albumin Through a Heterobifunctional Polyethylene Glycol," Pharm. Res., 12(12): 1883-1888 (1995).

Patrias et al., "Trimethylaminuria (Fish-Malodor Syndrome) and the Flavin Monooxygenases," Biotech Report, 106-107 (1994/1995).

Poznansky, "Enzyme-Protein Conjugates: New Possibilities for Enzyme Therapy," Pharmac. Ther., 21:53-76 (1983).

Poznansky et al., "Growth Hormone-Albumin Conjugates Reduced Renal Toxicity and Altered Plasma Clearance," FEBS Letters, 239(1):18-22 (1988).

Qu et al., "A Role for Melanin-Concentrating Hormone in the Central Regulation of Feeding Behaviour," Nature, 380:243-247 (1996).

Raufman, "Bioactive Peptides from Lizard Venoms," Regulatory Peptides, 61:1-18 (1996).

Reubi et al., "Specific High Affinity Binding Sites for Somatostatin-28 on Pancreatic β-Cells: Differences with Brain Somatostatin Receptors," Endocrinology, 110(3):1049-1051 (1982).

Ringsdorf, "Structure and Properties of Pharmacologically Active Polymers," J. Polymer Sci. Symposium No. 51, pp. 135-153 (1975).

Ritzel et al., "A Synthetic Glucagon-like Peptide-1 Analog with Improved Plasma Stability," Journal of Endocrinology, 159:93-102 (1998).

Robberecht et al., "Immunoreactive Helodermin-like Peptides in Rat: A New Class of Mammalian Neuropeptides Related to Secretin and VIP," Biochem. Biophys. Res. Commun., 130(1):333-342 (1985).

Ruiz-Grande et al., "Lipolytic Action of Glucagon-like Peptides in Isolated Rat Adipocytes," Peptides, 13(1)13-16 (1992).

Santiago, "Incidence of IDDM and Frequency of the DQβ1 and DQα1," Diabetes, Abstract book, 56th Annual Meeting and Scientific Sessions, 847 (Jun. 8-11, 1996).

Schirra et al., "Exendin(9-39)amide is an Antagonist of Glucagon-like Peptide-1(7-36)amide in Humans," J. Clin. Invest., 101(7):1421-1430 (1998).

Selkoe, "Physiological Production of the β-Amyloid Protein and the Mechanism of Alzheimer's Disease," TINS, 16(10):403-409 (1993).

Siegel et al., "Biological Activity of GLP-1 Analogues with N-Terminal Modifications," Regulatory Peptides, 79(23):93-102 (1999).

Smith et al., "Atrial Natriuretic Factor During Fetal and Postnatal Life: A Review," J. Dev. Physiol., 12:55-62 (1989).

Stehle et al., "The Loading Rate Determines Tumor Targeting Properties of Methotrexate-Albumin Conjugates in Rats," Anti-Cancer Drugs, 8:677-685 (1997).

Syed et al., "Potent Antithrombin Activity and Delayed Clearance from the Circulation Characterize Recombinant Hirudin Genetically Fused to Albumin," Blood, 89(9):3243-3252 (1997).

Thim et al., "Molecules in Focus: CART, a New Anorectic Peptide," Int. J. Biochem. Cell. Biol., 30:1281-1284 (1998).

Turton et al., "A Role for Glucagon-like-Peptide-1 in the Central Regulation of Feeding," Nature, 379:69-72 (1996).

Vilaseca et al., "Proteins Conjugates of Defined Structure: Synthesis and Use of a New Carrier Molecule," Bioconjug. Chem., 4:515-520 (1993).

Yeh et al., "Design of Yeast-Secreted Albumin Derivatives for Human Therapy: Biological and Antiviral Properties of a Serum Albumin-CD4 Genetic Conjugate," Proc. Natl. Acad. Sci. USA, 89:1904-1908 (1992).

Young et al., "Glucose-Lowering and Insulin-Sensitizing Actions of Exendin-4," Diabetes, 48:1026-1034 (1999).

Zalipsky, "Functionalized Poly(ethylene glycol) for Preparation of Biologically Relevent Conjugates," Bioconjug. Chem., 6:150-165 (1995).

Zegers et al., "An Improved Conjugation Method for Controlled Covalent Coupling of Synthetic Peptides to Proteins Using Glutaraldehyde in a Dialysis Method," Journal of Immunological Methods, 130:195-200 (1990).

* cited by examiner

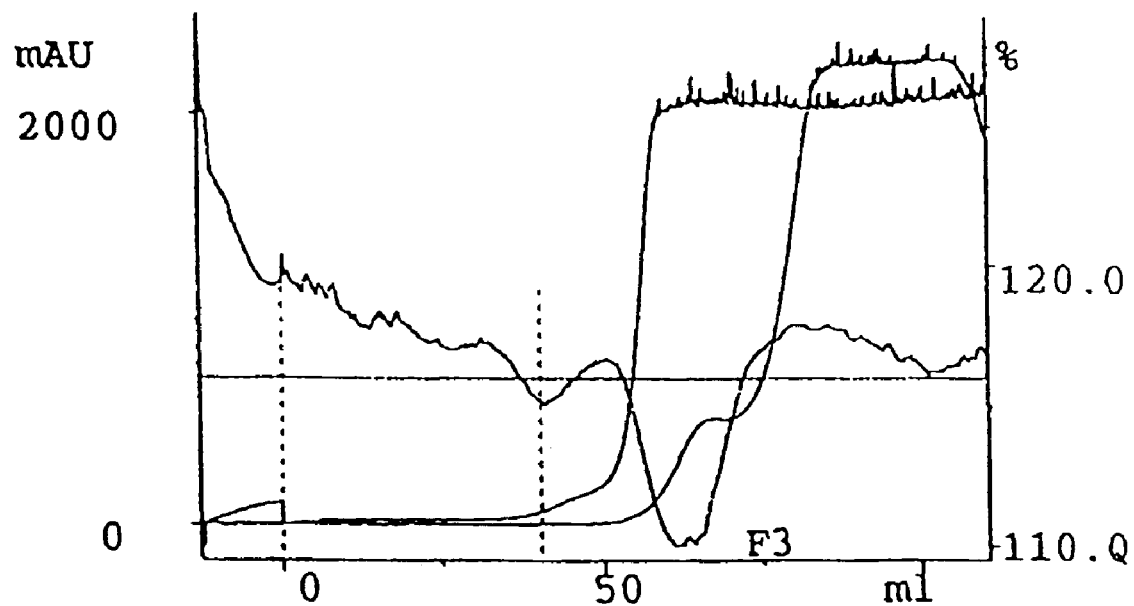
Figure 69-A
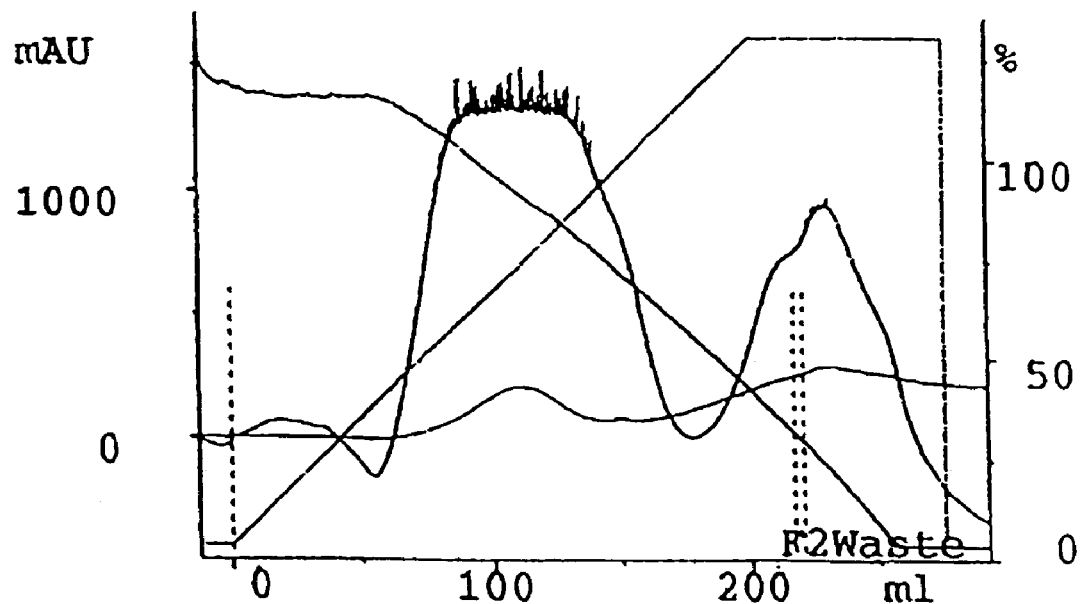
Figure 69-B

METHOD FOR PURIFICATION OF ALBUMIN CONJUGATES

RELATED APPLICATION

This application claims priority to U.S. provisional patent application Ser. No. 60/565,228 filed Apr. 23, 2004, which is expressly incorporated by reference in its entirety.

BACKGROUND OF THE INVENTION (a) Field of the Invention

This invention relates to a method of purification for isolating albumin conjugates from a solution comprising both albumin conjugates and unconjugated albumin.

(b) Description of Prior Art

WO 95/10302 and WO 99/24074 describe the formation of conjugates of albumin wherein the molecule of interest has a reactive functionality coupled thereto that is adapted to covalently bond to albumin, thus forming a conjugate. These conjugates can be formed in vivo, but they can be formed in vitro as well. The formation of the conjugate in vitro involves the addition of a molecule coupled to a reactive functionality to a solution of albumin. The primary end products from this reaction are unconjugated albumin, the albumin conjugate and the unreacted molecule coupled to the reactive functionality.

It would be highly desirable to be provided with a method for purifying albumin conjugate from a solution comprising albumin conjugate and unconjugated albumin.

SUMMARY OF THE INVENTION

In accordance with the present invention there is provided a method for separating albumin conjugate from unconjugated albumin in a solution comprising albumin conjugate and unconjugated albumin, the method comprising:
a) loading the solution onto a hydrophobic solid support equilibrated in aqueous buffer having a high salt content;
b) applying to the support a gradient of decreasing salt content; and
c) collecting eluted albumin conjugate.

In a preferred embodiment of the present invention, the albumin conjugate consists of a molecule having a Michael acceptor covalently coupled thereto which bonds to albumin, and more preferably the bond is between the Michael acceptor and cysteine 34 of albumin.

In a more preferred embodiment of the present invention, the Michael acceptor is a maleimide group, and more preferably, the maleimide group is maleimid-propionic acid (MPA). The Michael acceptor is optionally coupled to the molecule via a linker. The linker is preferably selected in the group consisting of hydroxyethyl motifs such as (2-amino) ethoxy acetic acid (AEA), ethylenediamine (EDA), 2-[2-(2-amino)ethoxy)]ethoxy acetic acid (AEEA), amino ethoxy ethyl amino succinic acid (AEEAS); one or more alkyl chains (C1-C10) motifs such as glycine, 3-aminopropionic acid (APA), 8-aminooctanoic acid (AOA), octanoic acid (OA), 4-aminobenzoic acid (APhA). Preferred linkers are OA, ADE, AEA, AEEA and AEEAS. A combination of two linkers can also be used such as, for examples, AEEA-EDA, AEEA-AEEA, AEEAS-AEEAS, and AEA-AEEA.

In a preferred embodiment of the present invention, the albumin is selected from the group consisting of serum albumin, recombinant albumin and albumin from a genomic source.

In a preferred embodiment of the present invention, the albumin is selected from the group consisting of human albumin, rat albumin, mouse albumin, swine albumin, bovine albumin, dog albumin and rabbit albumin, more preferable human serum albumin.

In a preferred embodiment, albumin is modified with at least one selected from the group consisting of fatty acids, metal ions, small molecules having high affinity to albumin, and sugars, such as, but not limited to, glucose, lactose and mannose.

In a preferred embodiment of the present invention, the molecule is selected from the group consisting of a peptide, DNA, RNA, small organic molecule and a combination thereof. The peptide has preferentially a molecular weight of at least 57 daltons. The peptide is intended to include, but not being limited to, GLP-1, GLP-2, ANP, K5, dynorphin, GRF, insulin, natriuretic peptides, T-20, T-1249, C-34 and PYY. The small molecule is intended to include, but not being limited to, vinorelbine, gemcitabine and paclitaxel. In a more preferred embodiment of the present invention, when the molecule is a DNA, RNA or a small organic molecule, it is covalently attached to the albumin through an acid sensitive covalent bond or a peptide sequence susceptible to proteolytic cleavage, thereby allowing the separation of the molecule from albumin and the entry of the molecule into a cell.

In a preferred embodiment of the present invention, the hydrophobic solid support is a column containing a hydrophobic resin such as, but not limited to, octyl sepharose, phenyl sepharose and butyl sepharose and more preferably butyl sepharose.

In another embodiment of the present invention, the hydrophobic solid support comprising a hydrophobic ligand such as Cibacron Blue F3G-A, ether or isopropyl groups in association with a support such as polystyrene/divinyl benzene matrix.

Substances are separated on the basis of their varying strengths of hydrophobic interactions with hydrophobic ligands immobilized to an uncharged matrix. This technique is usually performed with moderately high concentrations of salts ($\approx$1M) in the start buffer (salt promoted adsorption). Elution is achieved by a linear or stepwise decrease in salt concentration.

The type of ligand, the degree of substitution, the pH and the type and concentration of salt used during the adsorption stage have a profound effect on the overall performance (e.g. selectivity and capacity) of a HIC matrix (Hydrophobic Interaction Chromatography matrix).

The solvent is one of the most important parameters which influence capacity and selectivity in HIC (Hydrophobic Interaction Chromatography). In general, the adsorption process is more selective than the desorption process. It is therefore important to optimize the start buffer with respect to pH, type of solvent, type of salt and concentration of salt. The addition of various "salting-out" salts to the sample promotes ligand-protein interactions in HIC. As the concentration of salt is increased, the amount of bound protein increases up to the precipitation point for the protein. Each type of salt differs in its ability to promote hydrophobic interactions. The influence of different salts on hydrophobic interaction follows the well-known Hofmeisters series found below:

Hofmeisters Series

Salting-Out Effect

Anions:

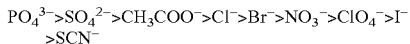

Chaotropic Effect

Cations:

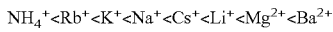

Increasing the salting-out effect strengthens the hydrophobic interactions, whereas increasing the chaotropic effect weakens them. Therefore, ammonium sulfate exhibits a stronger salting-out effect than sodium chloride. The most commonly used salts for HIC are ammonium sulfate (($NH_4)_2 SO_4$), sodium sulfate (($Na)_2SO_4$)), magnesium sulfate ($MgSO_4$), sodium chloride (NaCl), potassium chloride (KCl), and ammonium acetate ($CH_3COONH_4$).

Protein binding to HIC adsorbents is promoted by moderate to high concentrations of "salting-out" salts, most of which also have a stabilizing influence on protein structure due to their preferential exclusion from native globular proteins, i.e. the interaction between the salt and the protein surface is thermodynamically unfavorable. The salt concentration should be high enough (e.g. 500-1000 mM) to promote ligand-protein interactions yet below that which causes precipitation of the protein in the sample. In the case of albumin, the salt concentration should be kept below 3M (moles per liter). The principle mechanism of salting-out consists of the salt-induced increase of the surface tension of water (Melander and Horvath, 1977). Thus, a compact structure becomes energetically more favorable because it corresponds to smaller protein-solution interfacial area.

Interestingly, we found that under the same conditions (i.e. buffer composed of $SO_4^{2-}$, $PO_4^{2-}$ or $CH_3COO^-$ with any counter ion), these salts exhibit their salting-out effect upon essentially all conjugated albumin described herein in a manner different to non-conjugated albumin (i.e. mercaptalbumin and albumin capped with cysteine), thus enabling a consistent chromatographic separation between conjugated albumin versus non-conjugated albumin. That is, we observe that lower concentrations of salt are required to promote interactions between ligand and conjugated albumin than between ligand and non-conjugated albumin. This chromatographic separation is essentially independent of (a) the sequence of albumin (e.g. human, mouse, rat, etc.) (b) the source of albumin (i.e. plasma derived or recombinant) (c) the molecular weight of the conjugated molecule, (d) the position of the Michael acceptor (or maleimide group) within the structure of the molecule, (e) the peptide sequence or chemical structure of the molecule, and (f) the three-dimensional structure of the conjugated molecule, e.g. linear versus loop structure.

In a preferred embodiment of the present invention, the salt of the aqueous buffer has a sufficient salting out effect. For providing a sufficient salting out effect, the salt is preferably, but not limited to, phosphate, sulfate and acetate. More preferably, the salt is phosphate or sulfate. The selection of the cation of the buffer is less critical and therefore, such cation can be selected, without limitation, from the group consisting of $NH_4^+$, $Rb^+$, $K^+$, $Na^+$, $Cs^+$, $Li^+$, $Mg^{2+}$ and $Ba^{2+}$.

The aqueous buffer is preferably ammonium phosphate, ammonium sulfate and magnesium phosphate, and more preferably ammonium sulfate.

In a preferred embodiment of the present invention, the buffer pH is between 3.0 and 9.0; more preferably between 6.0 and 8.0, and even more preferably, the pH is 7.0.

In a preferred embodiment of the present invention, the buffer and the hydrophobic solid support are at room temperature (about 25° C.) or at 4° C. or in between.

Table 1 shows an example of the effect of varying salts for purification of preformed HSA: first GLP-1 analogue conjugate from a solution of HSA using butyl-sepharose resin (structure of the first GLP-1 analogue is described in Example 1 below).

TABLE 1

| Salt type | Starting salt concentration of 750 mM | Starting salt concentration of 1,750 mM |
|---|---|---|
| Ammonium phosphate | Yes | yes |
| Ammonium sulfate | Yes | yes |
| Ammonium chloride | No | no |
| Ammonium iodide | No | no |
| Ammonium thiocyanate | No | no |
| Magnesium sulfate | No | yes |
| Magnesium phosphate* | — | — |
| Barium sulfate* | — | — |

*means that the salt is not soluble at concentrations of 1750 mM or 750 mM in 20 mM sodium phosphate (pH 7), 5 mM caprylate
Yes means that successful resolution is achieved between the HSA: first GLP-1 analogue conjugate and the non-conjugated HSA
No means that no separation is achieved between the HSA: first GLP-1 analogue conjugate and the non-conjugated HSA The term "peptide" is intended to mean an amino acid sequence having a molecular weight of at least 57 daltons. The peptidic sequence can be circular (loop structure) such as ANP, may contain more than one amino acid chain such as insulin or may be linear such as K5, dynorphin A, C-34 and GLP-1.

All references herein are hereby incorporated by reference.

BRIEF DESCRIPTION OF THE DRAWINGS

FIGS. 69A-B illustrates the purification of the conjugate HSA: third ANP analogue CJC 1681 (SEQ ID NO:51) by a preferred embodiment of the method of the present invention;

DETAILED DESCRIPTION OF A PREFERRED EMBODIMENT OF THE INVENTION

Figure 1:
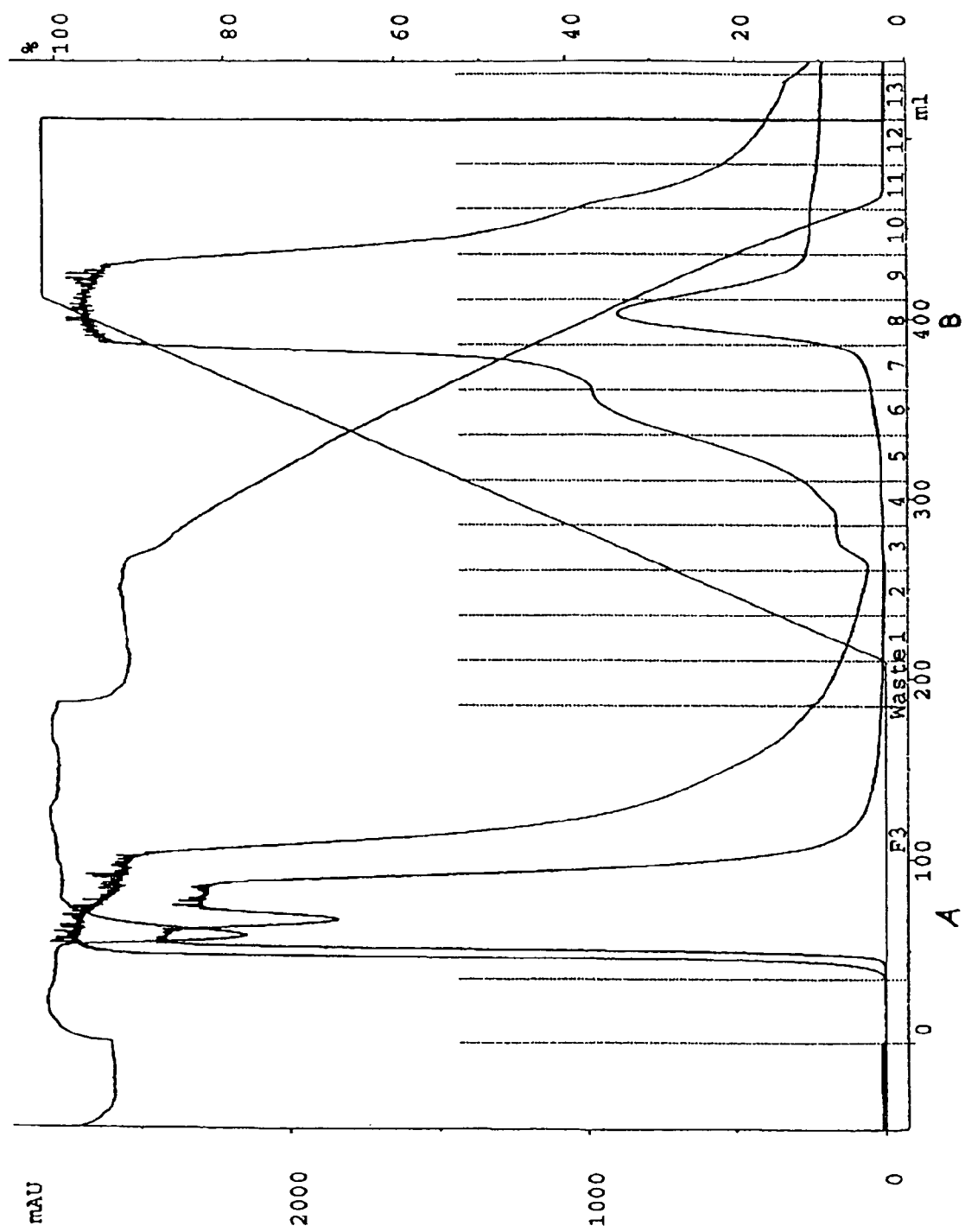
FIG. 1 illustrates the purification of the conjugate HSA: first GLP-1 analogue (SEQ ID NO:1) by a preferred embodiment of the method of the present invention.

In accordance with the present invention, there is provided a method for purifying albumin conjugates from a solution comprising albumin conjugates and unconjugated albumin.

Methods

Preparation of Control (Non-Conjugated) Human Serum Albumin (HSA) and Preformed Albumin Conjugates Each compound with the Michael acceptor was solubilized in nanopure water (or in DMSO if the compound was difficult to solubilize) at a concentration of 10 mM, then diluted to 1 mM into a solution of HSA (25%, 250 mg/ml, Cortex-Biochem, San Leandro, Calif.). The samples were then incubated at 37° C. for 30 min. Prior to their purification, each conjugate solution was diluted to 5% 50 mg/ml HSA in 20 mM sodium phosphate buffer (pH 7) composed of 5 mM sodium octanoate. The initial concentration of salt used in the elution gradient can be added to the buffer for diluting the mixed solution. Preferably, the initial concentration of salt is from about 750 to about 1700 mM $(NH_4)_2SO_4$.

Procedure for Purification According to a Preferred Embodiment

Using an ÄKTA purifier (Amersham Biosciences, Uppsala, Sweden), each conjugate was loaded at a flow rate of 2.5 ml/min onto a 50 ml column of butyl sepharose 4 fast flow resin (Amershan Biosciences, Uppsala, Sweden) equilibrated in 20 mM sodium phosphate buffer (pH 7) composed of 5 mM sodium octanoate and 750 mM to 1.7 M $(NH_4)_2SO_4$. Under these conditions, HSA conjugates having a molecular weight addition of more than 2 kDa relative to non-conjugated HSA adsorbed onto the hydrophobic resin whereas essentially all non-conjugated HSA eluted within the void volume of the column. For molecular weight additions of less than 2 kDa, a higher initial salt content may be used followed by a stepwise gradient of decreasing salt. Each conjugate was further purified from any free unconjugated compound by applying a continuous or non-continuous decreasing gradient of salt (750 to 0 mM $(NH_4)_2SO_4$) over 4 column volumes. In a preferred embodiment, each purified conjugate was then desalted and concentrated by diafiltration, for instance by using Amicon® ultra centrifugal (30 kDa) filter devices (Millipore Corporation, Bedford, Mass.). Finally, for prolonged storage, each conjugate solution is preferably immersed into liquid nitrogen, and lyophilized using a Labconco freeze dry system (FreeZone®4.5), and stored at −20° C.

Examples of LC/EMS Analysis

Following purification, 1 μl of each conjugate sample is preferably injected onto LC/EMS system. The HSA: first GLP-1 analogue (SEQ ID NO:1) conjugate was confirmed by detection of a species of highest abundance with a total mass of 70 160 Da which corresponds to the mass of mercaptalbumin (66 448 Da) where cysteine 34 is in the free thiol form, plus the mass of only one molecule of the first GLP-1 analogue (3 719.9 Da). The structure of the first GLP-1 analogue (SEQ ID NO:1) is described in Example 1 below. This is illustrated in Table 2.

TABLE 2

| Component | Molecular Weight | Absolute Abundance | Relative Abundance |
| --- | --- | --- | --- |
| A | 70160.58 | 321970 | 100.00 |
| B | 65862.95 | 70008 | 21.74 |
| C | 64545.45 | 62888 | 19.53 |
| D | 70320.04 | 41167 | 12.79 |
| E | 61287.67 | 16842 | 5.23 |
| F | 60623.81 | 16522 | 5.13 |
| G | 58090.04 | 12473 | 3.87 |

The HSA: first GRF analogue (SEQ ID NO:2) conjugate was confirmed by detection of a species of highest abundance with a total mass of 70 086 Da which corresponds to the mass of mercaptalbumin (66 448 Da) where cysteine 34 is in the free thiol form, plus the mass of only one molecule of the first GRF analogue (3648.2 Da). The structure of the first GRF analogue (SEQ ID NO:2) is described in Example 2 below. This is illustrated in Table 3.

TABLE 3

| Component | Molecular Weight | Absolute Abundance | Relative Abundance |
| --- | --- | --- | --- |
| A | 70086.06 | 279413 | 100.00 |
| B | 63214.84 | 53333 | 19.09 |
| C | 62148.17 | 38582 | 13.81 |
| D | 70247.98 | 34870 | 12.48 |
| E | 56795.96 | 10523 | 3.77 |
| F | 62695.49 | 9813 | 3.51 |

The following examples illustrate several compounds having a maleimide group as Michael acceptor that have been conjugated to albumin and purified in accordance with the method of the present invention.

The following examples are for the purpose of illustrating the present invention and not of limiting its scope.

In the following examples, the gradient numbers refer to the following gradient details, where CV means a column volume of 50 ml.

Gradient #1: Linear 750-0 mM $(NH_4)_2SO_4$, over 4 CV, flow rate of 2.5 ml/min.

Gradient #2: Step gradient 1.75M-1.2M $(NH_4)_2SO_4$ over 0.5 CV, followed by 1.2M-875 mM $(NH_4)_2SO_4$ over 5 CV, and finally 875 mM-0 mM $(NH_4)_2SO_4$ over 0.5 CV flow rate of 2.5 ml/min.

Gradient #3: Linear 900-0 mM $(NH_4)_2SO_4$ over 4 CV, flow rate of 2.5 ml/min.

Gradient #4: Step gradient 1.5M-1.1M $(NH_4)_2SO_4$ over 0.5 CV, followed by 1.1M-375 mM $(NH_4)_2SO_4$ over 6 CV, and finally 375 mM-0 mM $(NH_4)_2SO_4$ over 0.5 CV, flow rate of 2.5 ml/min.

Gradient #5: Linear 750-0 mM $(NH_4)_2SO_4$ over 2 CV, flow rate of 2.5 ml/min.

Gradient #6: Step gradient 1.75M-0M $(NH_4)_2SO_4$ over 6 CV, flow rate of 2.5 ml/min.

Gradient #7: Linear 750-0 mM $(NH_4)_2SO_4$ over 6 CV, flow rate of 2.5 ml/min.

EXAMPLE 1

Purification of HSA:First GLP-1 Analogue (SEQ ID NO:1) Conjugate

The first GLP-1 analogue is GLP-1 (7-36) dAla$^8$ Lys$^{37}$ (ε-AEEA-MPA)-CONH$_2$ and has the following sequence:

H(dA)EGTFTSDVSSYLEGQAAKEFIAWLVKGRK (AEEA-MPA)-CONH$_2$

The purification of a conjugate made from reacting 1 ml 25% 250 mg/ml HSA (Cortex-Biochem, San Leandro, Calif.) with 1 mM first GLP-1 analogue diluted into 9 ml of buffer made of 20 mM sodium phosphate buffer pH 7.0, 5 mM sodium caprylate and 750 mM $(NH_4)_2SO_4$, was performed on a column of Butyl sepharose using the gradient #1 described above. In FIG. 1 the purified conjugate fraction elutes during the gradient of decreasing $(NH_4)_2SO_4$ concentration as fraction B (F8-F9), whereas non-conjugated albumin elutes within the void volume of the column (fraction A). The conjugate fraction was concentrated with Ultrafree™ filter 30 kDa and analyzed using LC-EMS.

EXAMPLE 2

Purification of HSA:First GRF Analogue (SEQ ID NO:2) Conjugate

The first GRF analogue is GRF (1-29) dAla$^2$ Gln$^8$ Ala$^{15}$ Leu$^{27}$ Lys$^{30}$ (ε-MPA) CONH$_2$ and has the following sequence:

YaDAIFTQSYRKVLAQLSARKLLQDILSRK(MPA)-CONH$_2$

Figure 2:
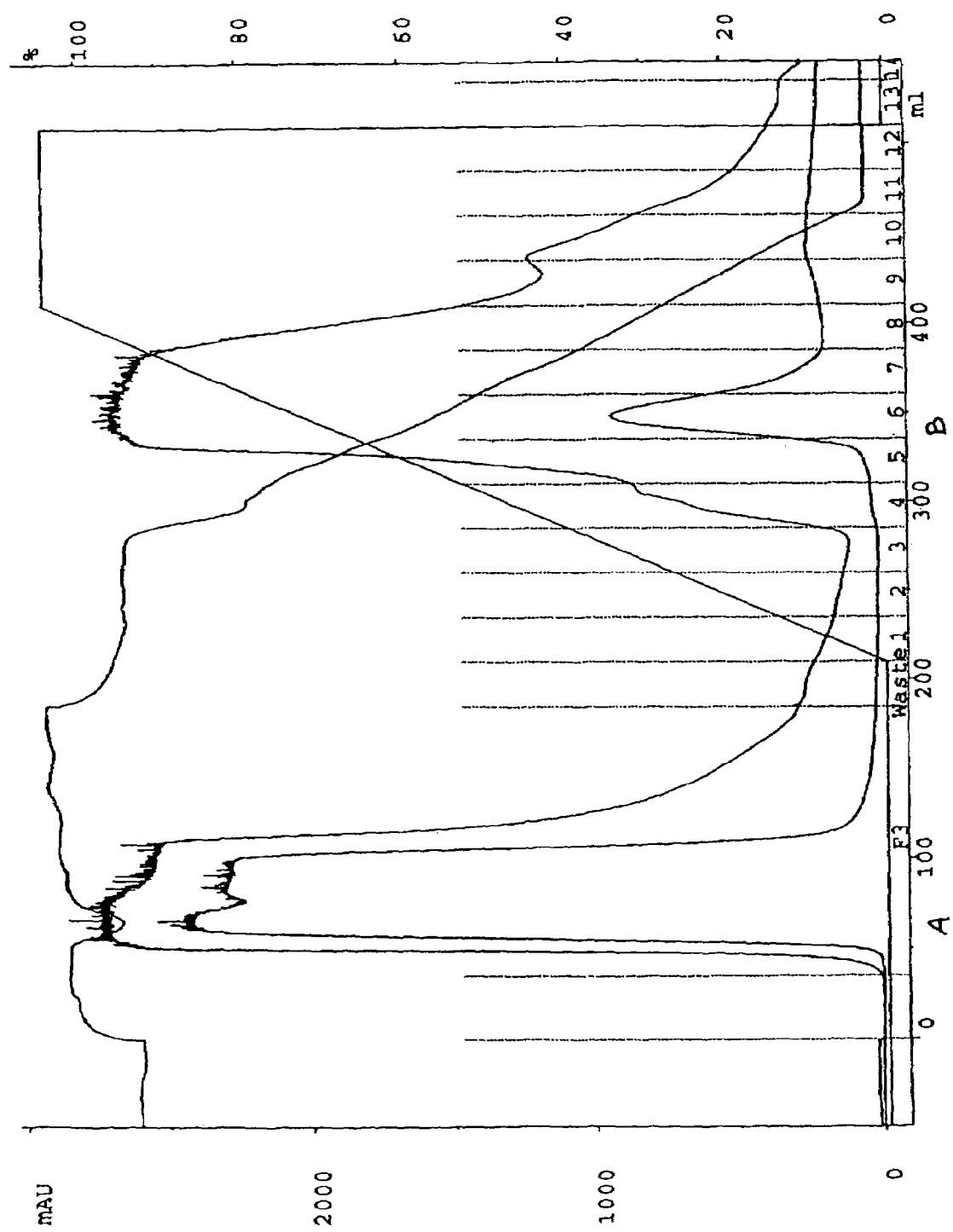
FIG. 2 illustrates the purification of the conjugate HSA: first GRF analogue (SEQ ID NO:2) by a preferred embodiment of the method of the present invention.

The purification of a conjugate made from reacting 1 ml 25% 250 mg/ml HSA (Cortex-Biochem, San Leandro, Calif.) with 1 mM first GRF analogue diluted into 9 ml of 20 mM sodium phosphate buffer (pH 7.0), 5 mM sodium caprylate and 750 mM $(NH_4)_2SO_4$, was performed on a column of Butyl sepharose using the gradient #1 described above. In FIG. 2 the purified conjugate fraction appears in fraction B (F6-F7) whereas non-conjugated albumin elutes within the void volume of the column (fraction A). The conjugate fraction was concentrated with Ultrafree™ filter 30 kDa and analyzed using LC-EMS.

EXAMPLE 3

Purification of Non-Conjugated HSA 1 ml

Figure 3:
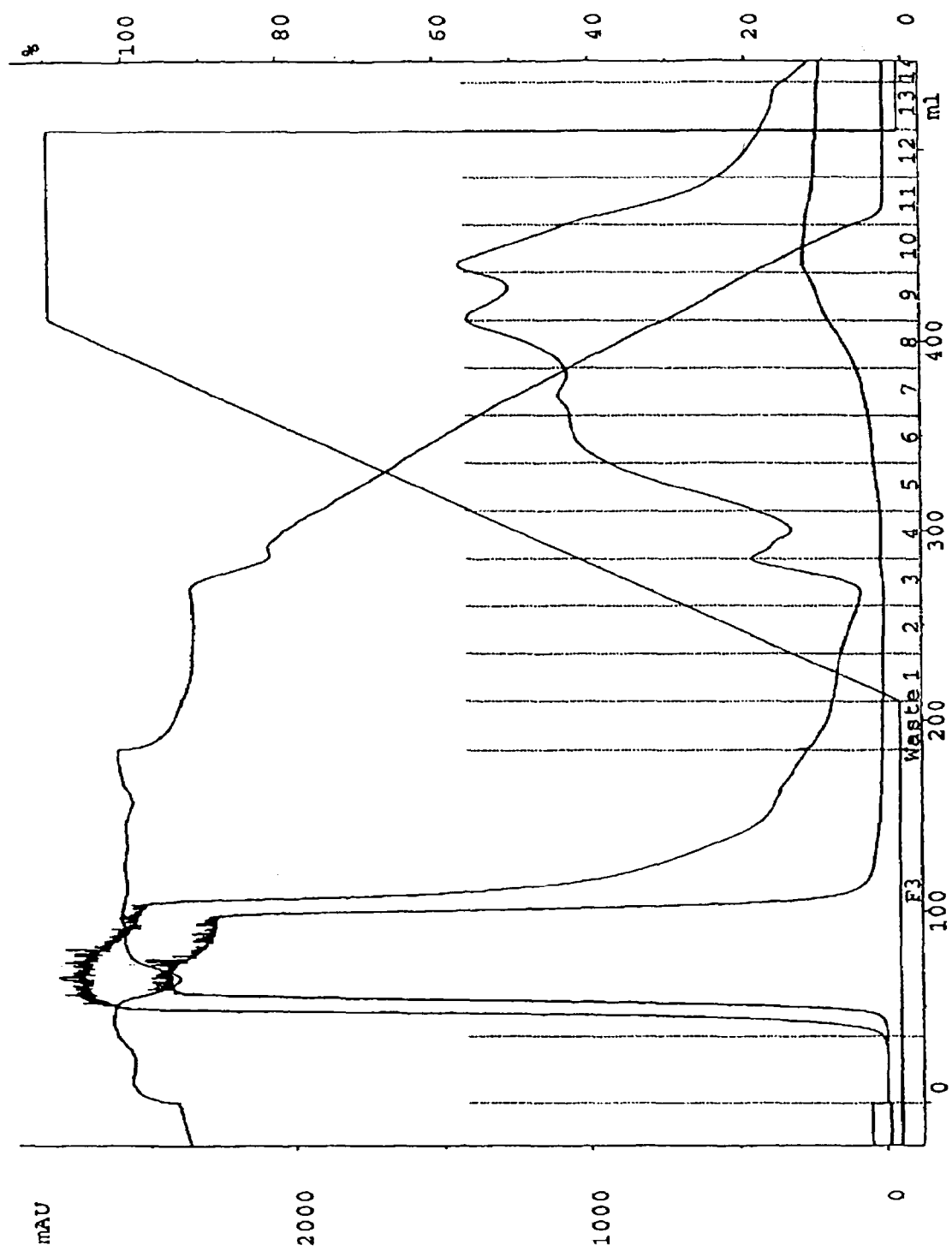
FIG. 3 illustrates the purification of non-conjugated HSA by a preferred embodiment of the method of the present invention.

The purification of 1 ml 25% 250 mg/ml non-conjugated HSA (Cortex-Biochem, San Leandro, Calif.) diluted into 9 ml of buffer (pH 7.0) made of 20 mM sodium phosphate buffer, 5 mM sodium caprylate and 750 mM $(NH_4)_2SO_4$, was performed on a column of Butyl sepharose using the gradient #1 described above. Essentially all albumin molecules elute within the void volume and no protein species is observed at 280 nm during $(NH_4)_2SO_4$ gradient. FIG. 3 illustrates the separation curve obtained.

EXAMPLE 4

Purification of rHSA:First GLP-1 Analogue (SEQ ID NO:1) Conjugate

The first GLP-1 analogue is GLP-1 (7-36) dAla$^8$ Lys$^{37}$ (ε-AEEA-MPA)-CONH$_2$ and his sequence is shown in Example 1.

Figure 4:
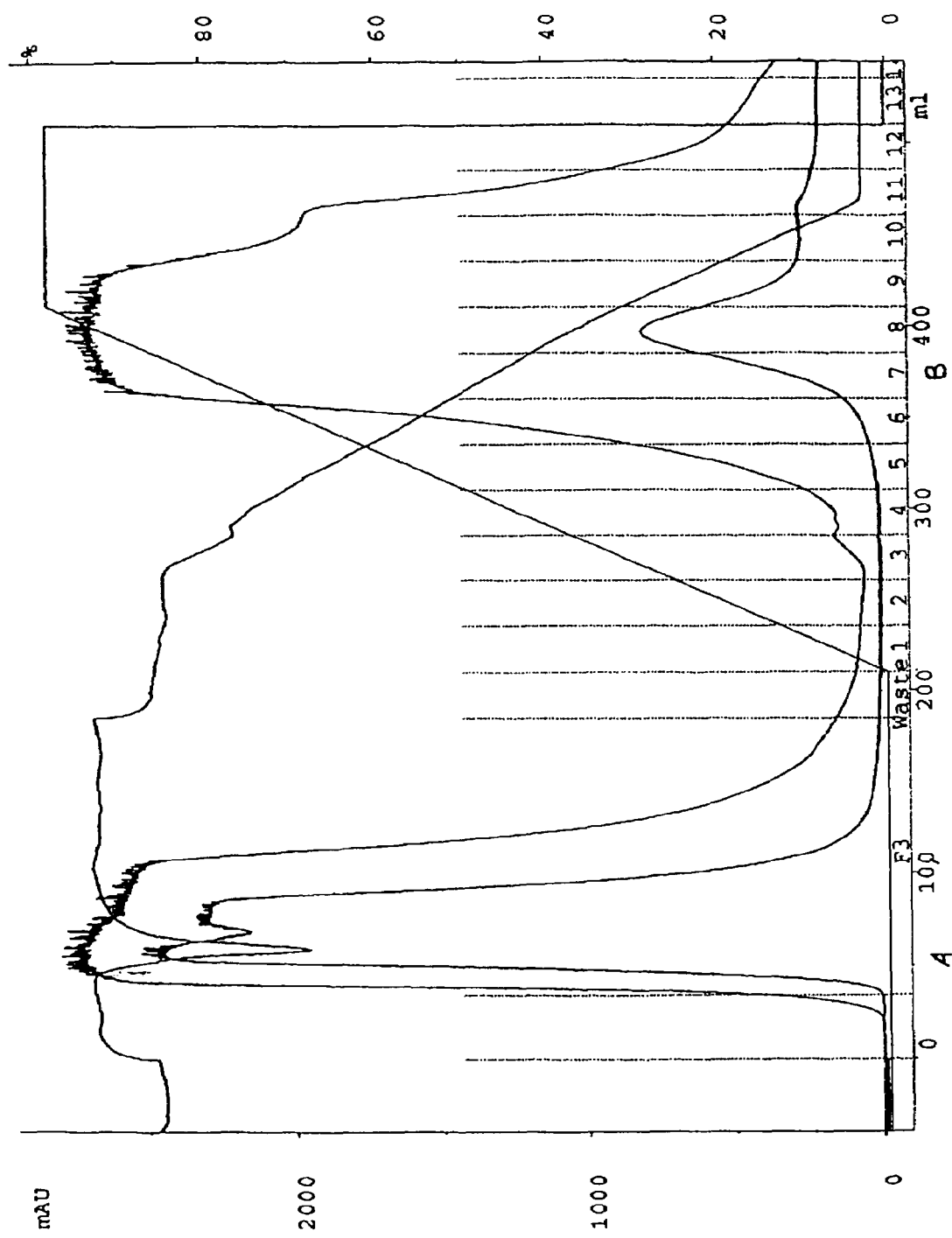
FIG. 4 illustrates the purification of the conjugate rHSA: first GLP-1 analogue (SEQ ID NO:1) by a preferred embodiment of the method of the present invention.

The purification of a conjugate made from reacting 5 ml 5% rHSA (recombinant HSA new century culture grade) with 200 μM first GLP-1 analogue diluted into 5 ml of a buffer made of 20 mM sodium phosphate buffer, 5 mM sodium caprylate and 750 mM (NH$_4$)$_2$SO$_4$ was performed on a column of Butyl sepharose using the gradient #1 described above. In FIG. 4 the purified conjugate fraction appears in fraction B (F7-F8-F9).

EXAMPLE 5

Purification of HSA 10 ml

Figure 5:
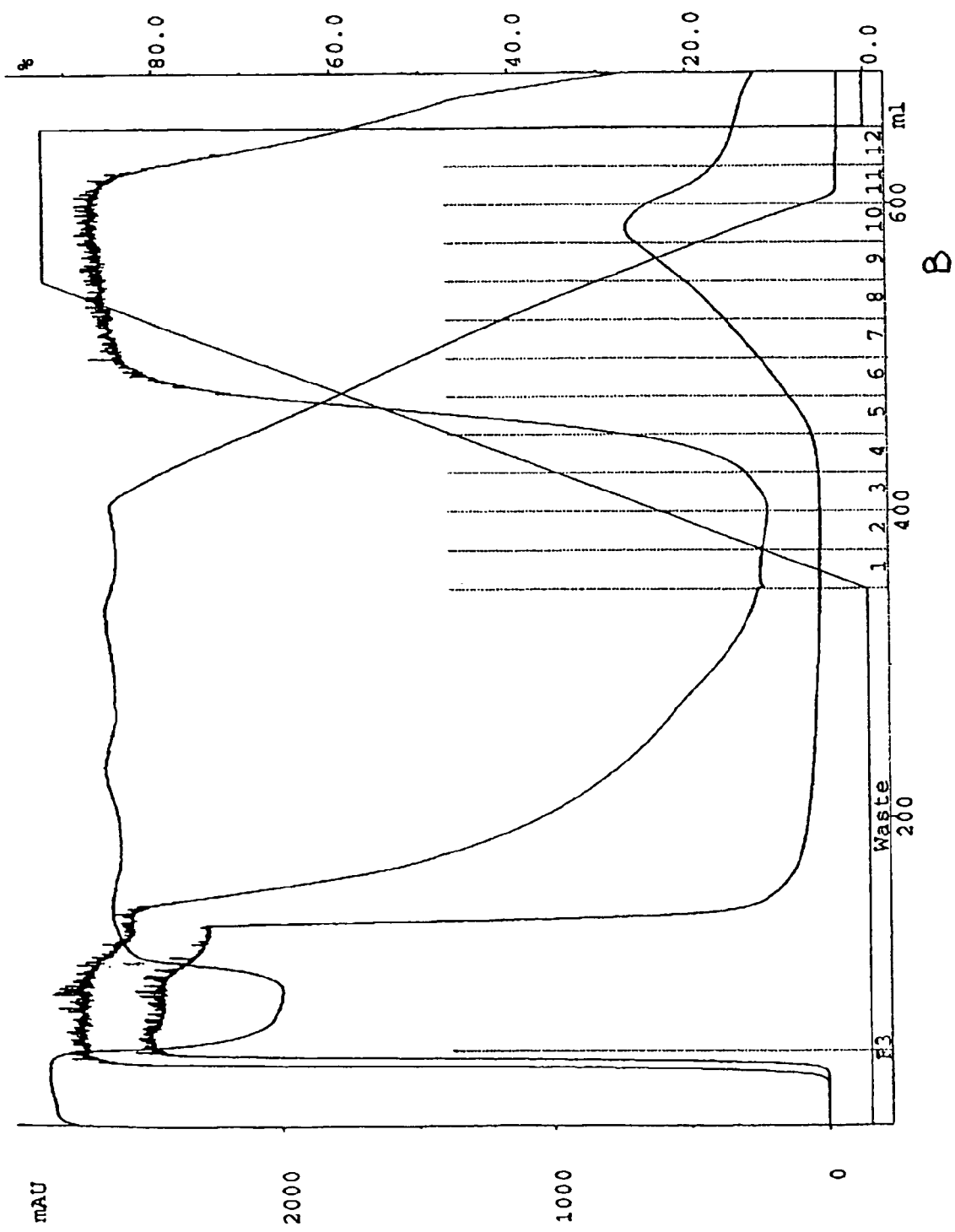
FIG. 5 illustrates the purification of HSA cortex by a preferred embodiment of the method of the present invention.

The purification of 10 ml 25% 250 mg/ml HSA (Cortex-Biochem, San Leandro, Calif.) diluted into 40 ml of a buffer made of 20 mM sodium phosphate buffer (pH 7.0), 5 mM sodium caprylate and 750 mM (NH$_4$)$_2$SO$_4$ was performed on a column of Butyl sepharose using the gradient #1 described above. Essentially all albumin molecules elute within a void volume and no protein species is observed at 280 nm during (NH$_4$)$_2$SO$_4$ gradient. FIG. 5 illustrates the separation curve obtained.

EXAMPLE 6

Purification of HSA:K5 Analogue (SEQ ID NO:3) Conjugate

The K5 analogue is Ac-K5 Lys$^8$ (ε-MPA)-NH$_2$ and has the following sequence:

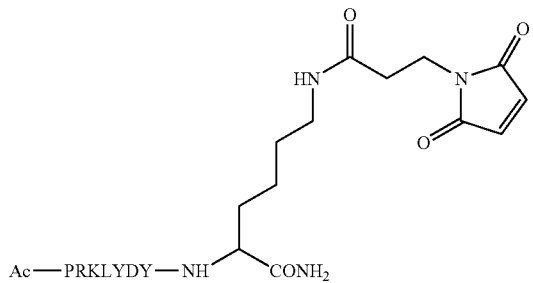

Figure 6:
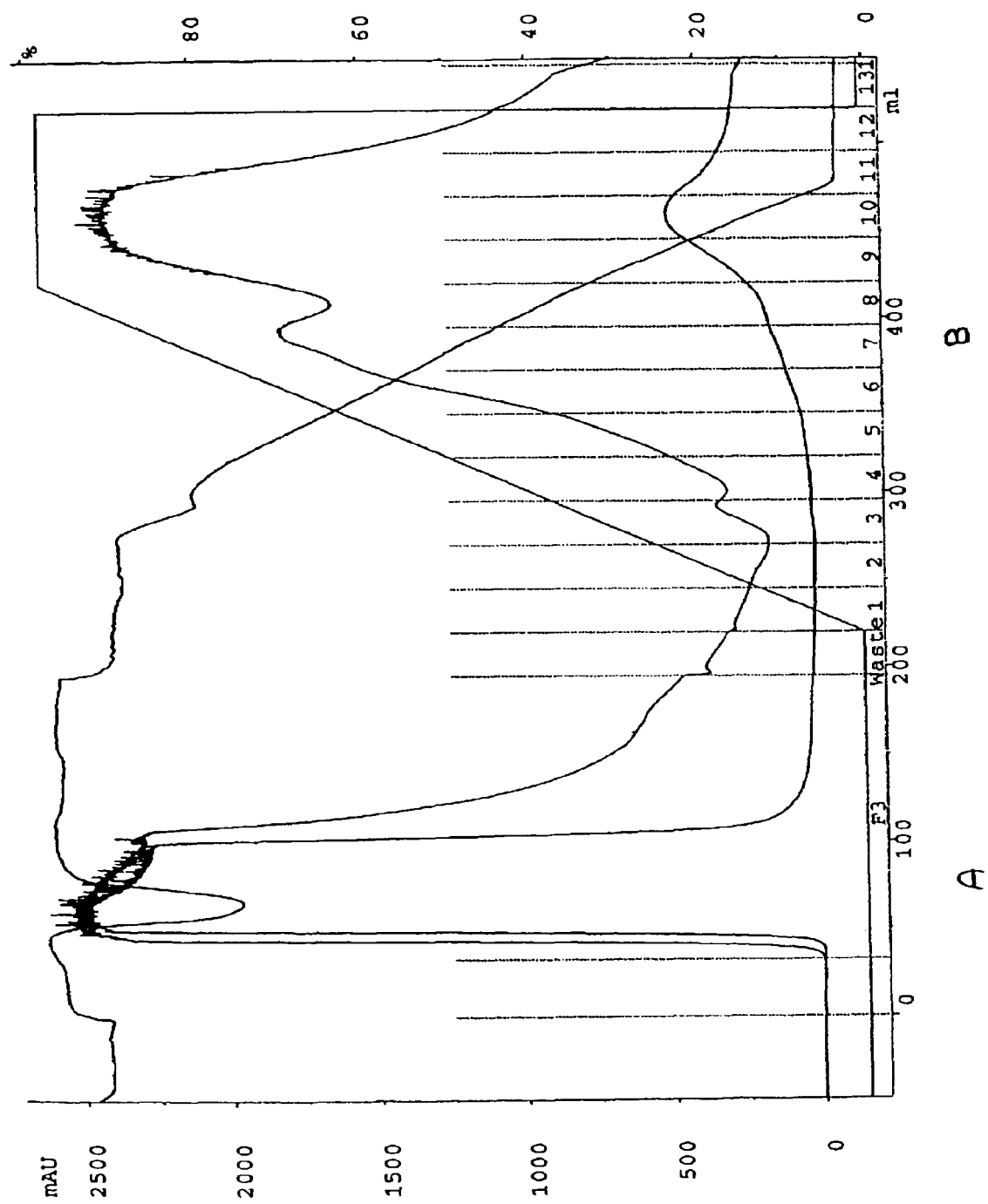
FIG. 6 illustrates the purification of the conjugate HSA: K5 analogue (SEQ ID NO:3) by a preferred embodiment of the method of the present invention.

The purification of a conjugate made from reacting 4 ml 25% 250 mg/ml HSA (Cortex-Biochem, San Leandro, Calif.) with 1 mM K5 analogue diluted into 16 ml of 20 mM sodium phosphate buffer (pH 7.0), 5 mM sodium caprylate and 750 mM (NH$_4$)$_2$SO$_4$ was performed on a column of Butyl sepharose using the gradient #1 described above. In FIG. 6 the purified conjugate fraction appears in fraction A with albumin and in fraction B (F6-F7-F8).

EXAMPLE 7

Purification of HSA:First Insulin Derivative (SEQ ID NO:4) Conjugate

The first insulin derivative is human insulin with MPA on position B1 and is represented in FIG. 1 below.

"Purification of HSA:First Insulin Derivative Conjugate

The first insulin derivative is human insulin with MPA on position B1 of B chain (SEQ ID NO: 4) and native A chain (SEQ ID NO: 35). FIG. 1 below represents the first insulin derivative."

"FIG. 1 also represents the other insulin derivatives that are disclosed in further examples. FIG. 1 provides the information concerning the intra disulfide bridge in A chain and the two inter disulfide bridges between A chain and B chain for all insulin derivatives exemplified."

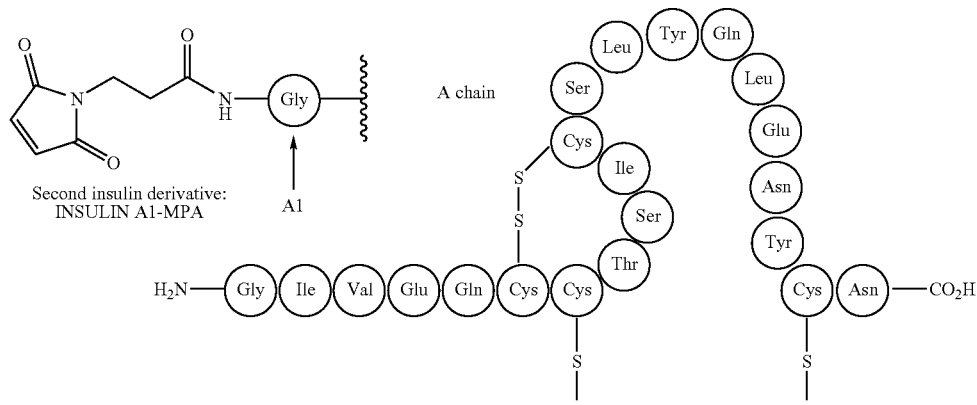

Figure 1

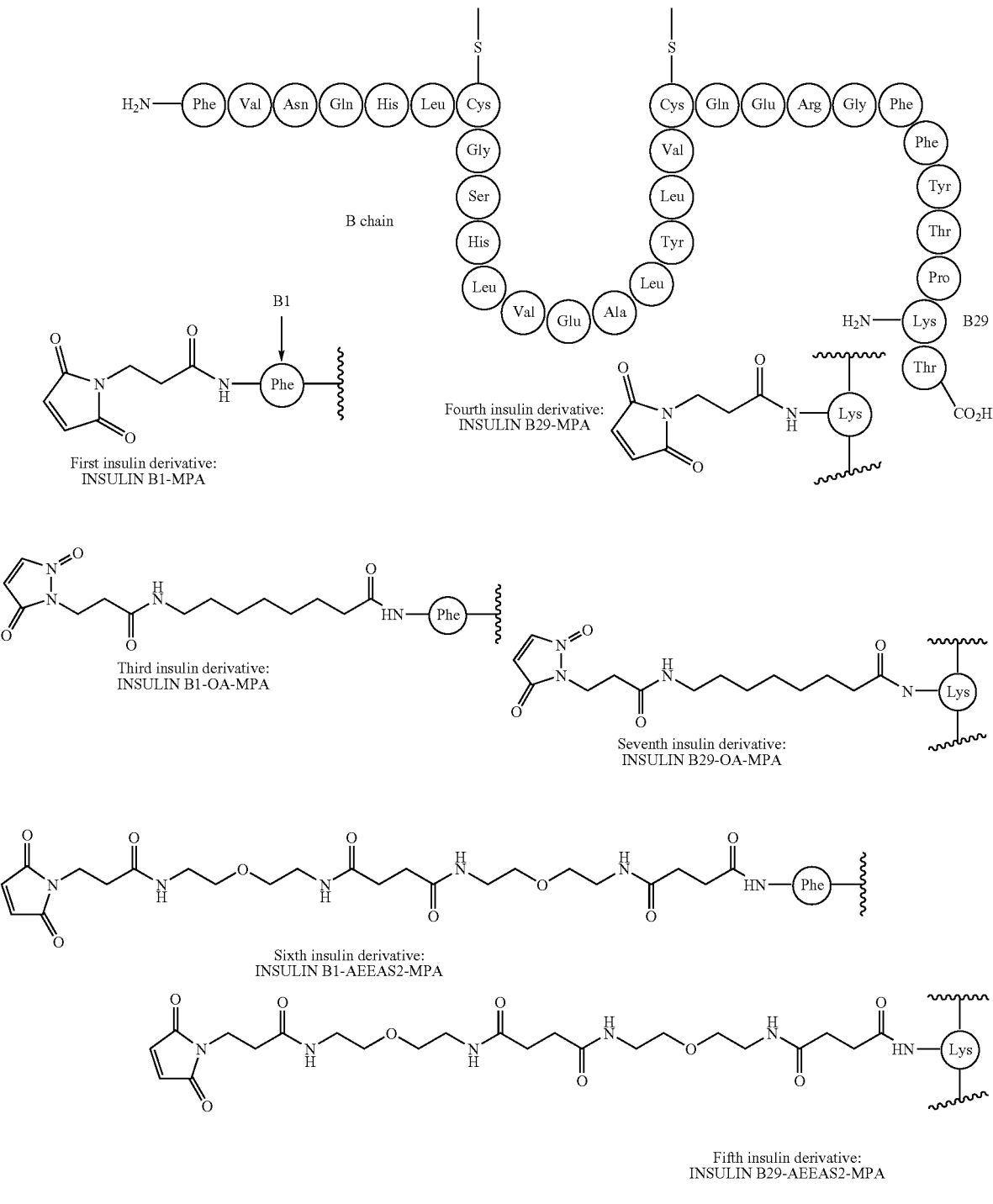

Figure 7:
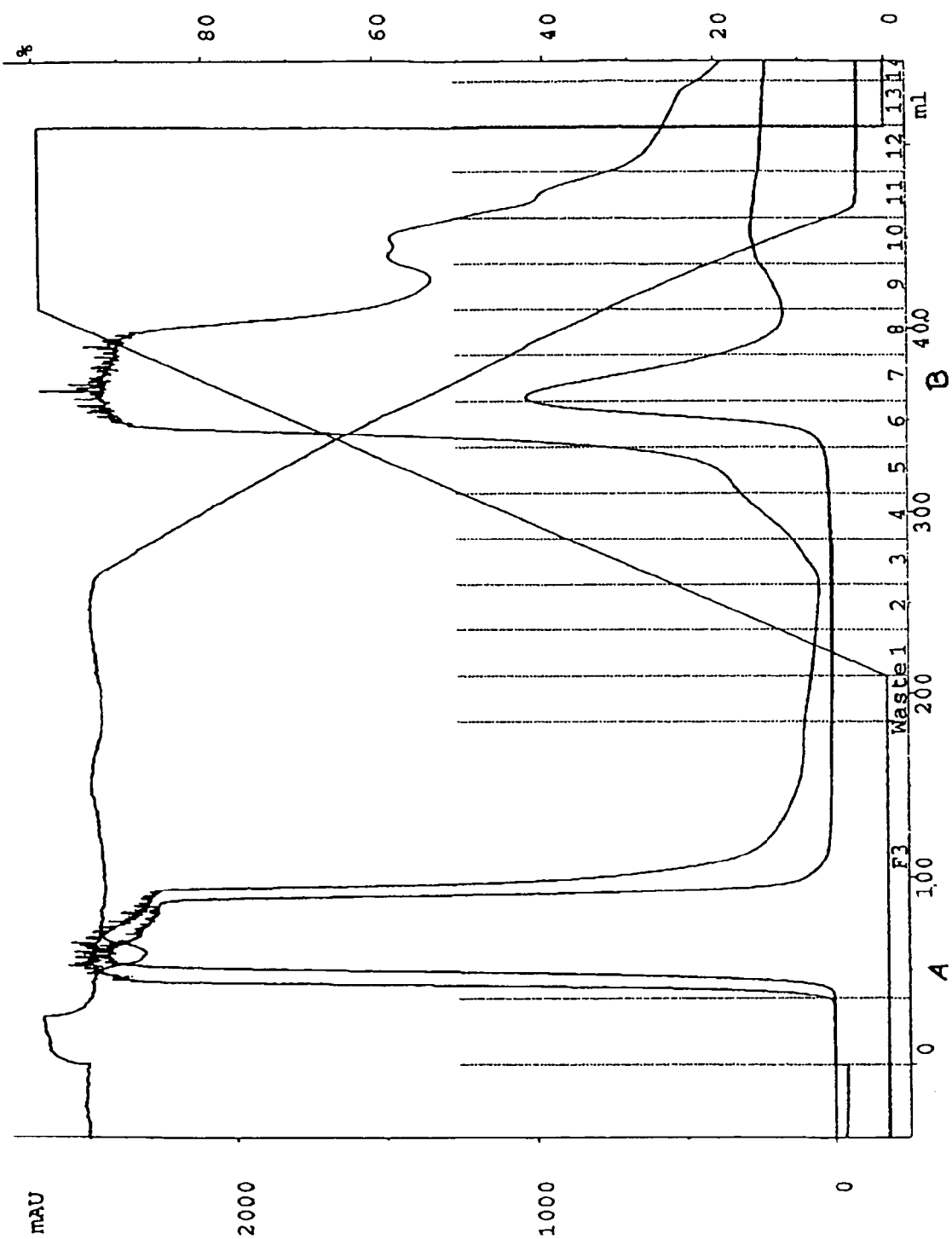
"FIG. 7 illustrates the purification of the conjugate HSA: first insulin derivative having modification on chain B (SEQ ID NO:4) by a preferred embodiment of the method of the present invention;"

The purification of a conjugate made from reacting 1 ml 25% 250 mg/ml HSA (Cortex-Biochem, San Leandro, Calif.) with 1 mM first insulin derivative diluted into 9 ml of 20 mM sodium phosphate buffer (pH 7.0), 5 mM sodium caprylate and 750 mM $(NH_4)_2SO_4$ was performed on a column of Butyl sepharose using the gradient #1 described above. In FIG. 7 the purified conjugate fraction appears in fraction B (F6-F7-F8).

EXAMPLE 8

"Purification of HSA: Second Insulin Derivative Conjugate

The second insulin derivative is human insulin with MPA on position A1 of A chain (SEQ ID NO: 5) and native B chain (SEQ ID NO: 53); and is represented in FIG. 1 shown above in Example 7."

Figure 8:
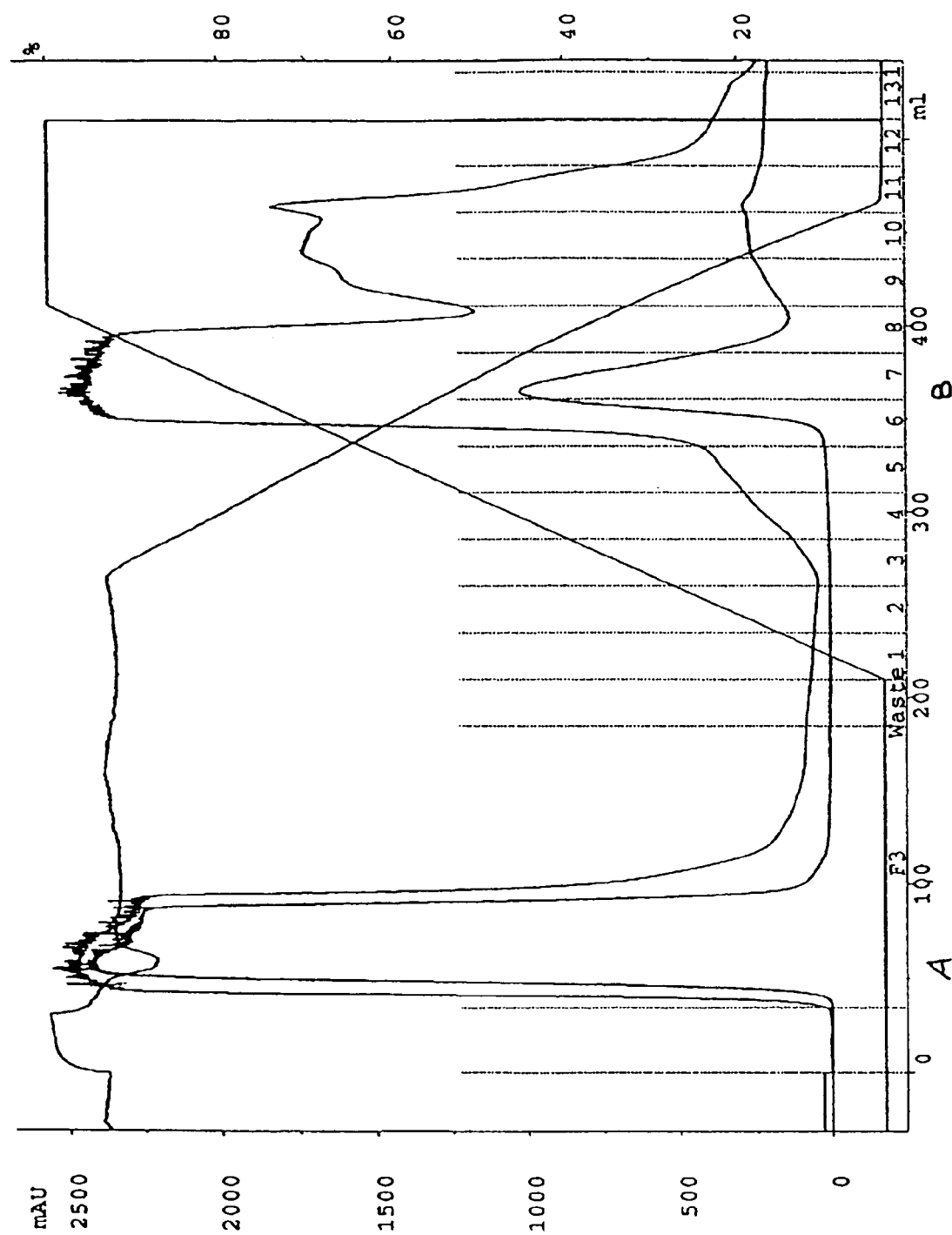
"FIG. 8 illustrates the purification of the conjugate HSA: second insulin derivative having modification on chain A (SEQ ID NO:5) by a preferred embodiment of the method of the present invention;"

The purification of a conjugate made from reacting 1 ml 25% 250 mg/ml HSA (Cortex-Biochem, San Leandro, Calif.) with 1 mM second insulin derivative diluted into 9 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 8 the purified conjugate fraction appears in fraction B (F6-F7-F8).

EXAMPLE 9

Purification of HSA: First C34 Analogue (SEQ ID NO:6) Conjugate

The first C34 analogue is MPA-AEEA-C34-$CONH_2$ and has the following sequence:

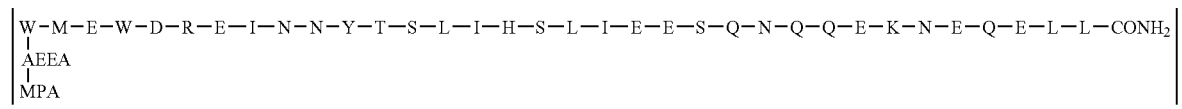

Figure 9:
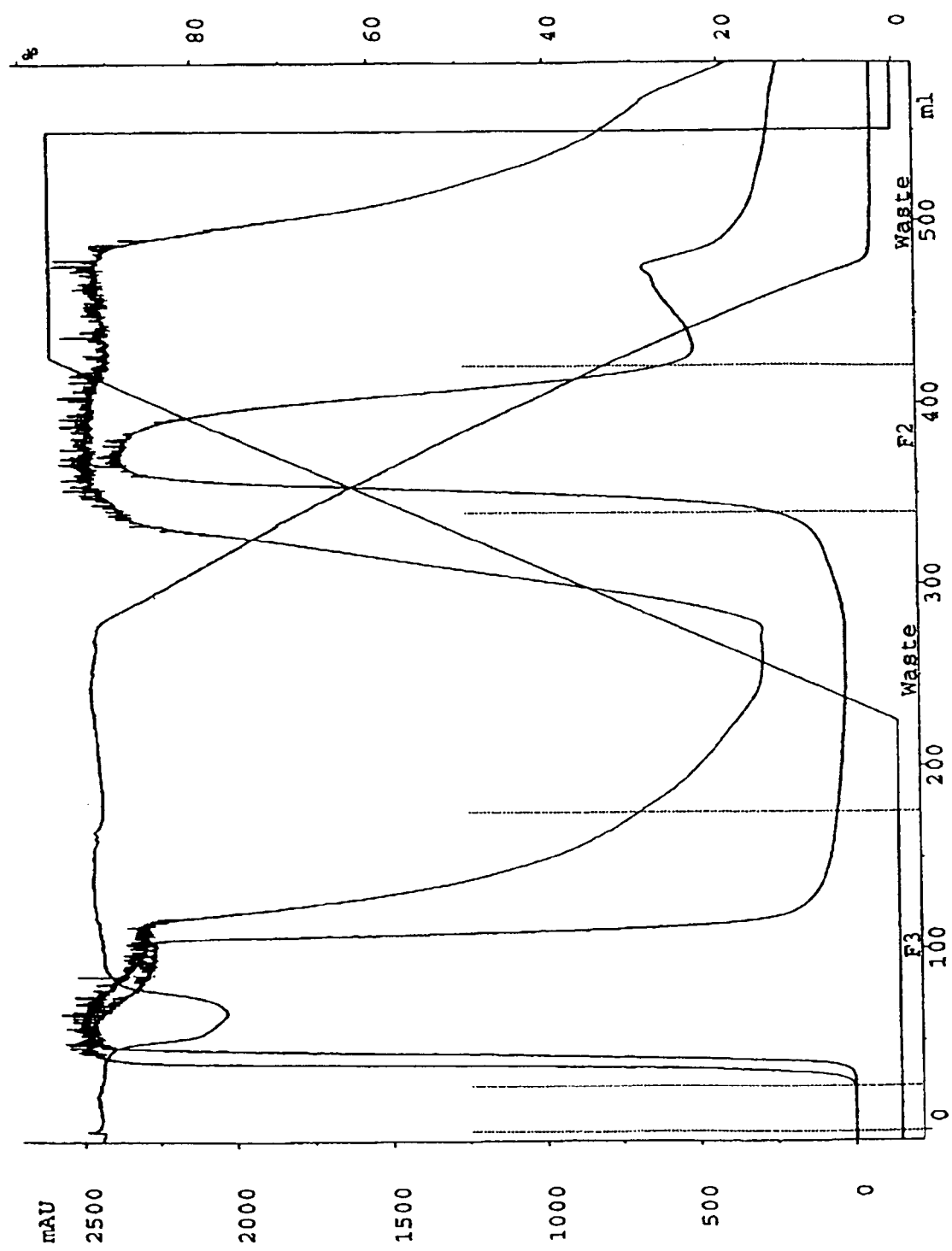
FIG. 9 illustrates the purification of the conjugate HSA: first C34 analogue (SEQ ID NO:6) by a preferred embodiment of the method of the present invention.

The purification of a conjugate made from reacting 5 ml 25% 250 mg/ml HSA (Cortex-Biochem, San Leandro, Calif.) with 1 mM first C34 analogue diluted into 20 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 9 the purified conjugate fraction appears in fraction F2.

EXAMPLE 10

Purification of HSA:Second C34 Analogue (SEQ ID NO:7) Conjugate

The second C34 analogue is C34 (1-34) $Lys^{35}$ ($\epsilon$-AEEA-MPA)-$CONH_2$ and has the following structure:

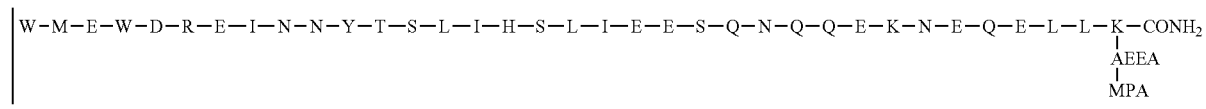

Figure 10:
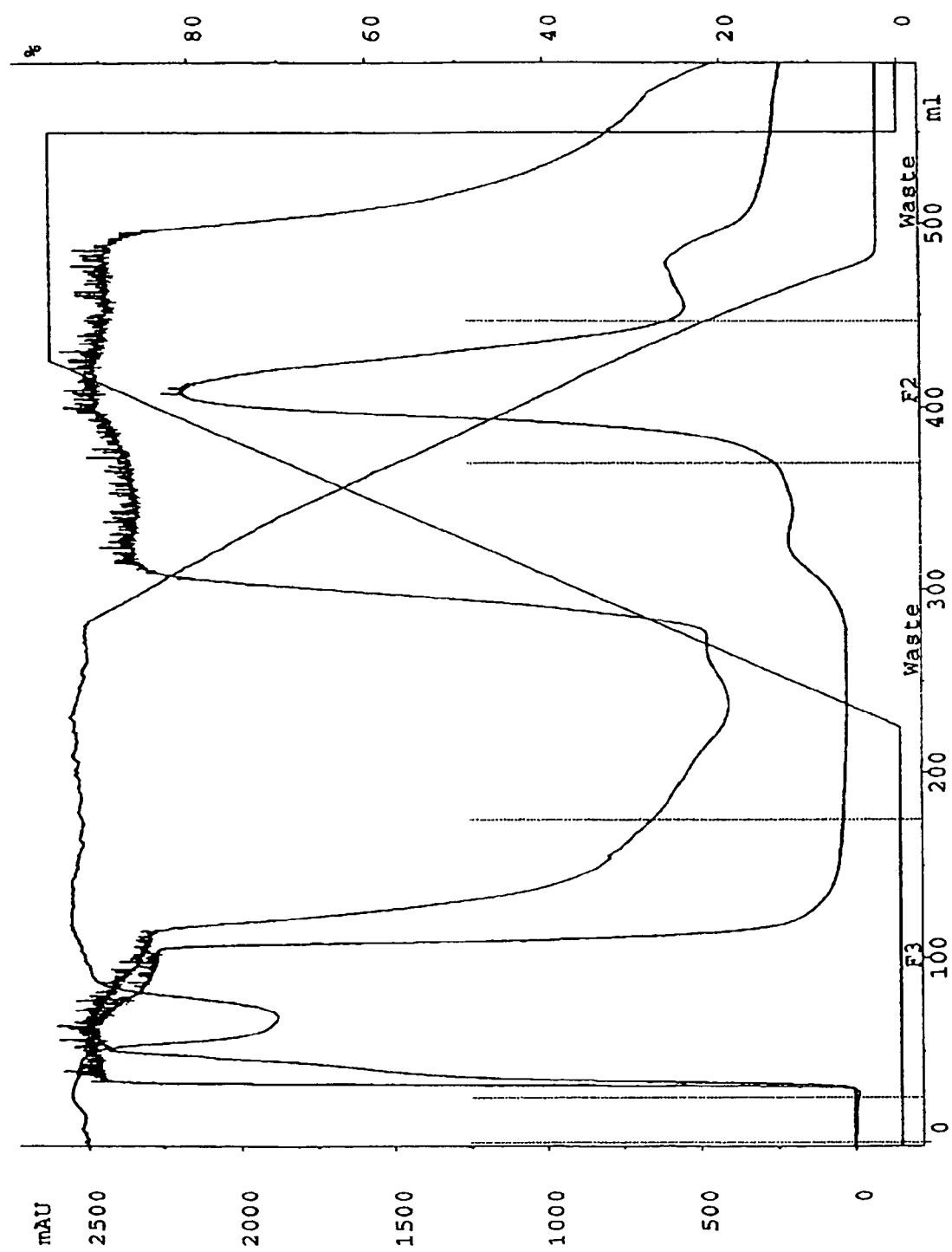
FIG. 10 illustrates the purification of the conjugate HSA: second C34 analogue (SEQ ID NO:7) by a preferred embodiment of the method of the present invention.

The purification of a conjugate made from reacting 5 ml 25% 250 mg/ml HSA (Cortex-Biochem, San Leandro, Calif.) with 1 mM second C34 analogue diluted into 20 ml of 20 mM sodium phosphate buffer, 5 mM sodium caprylate and 750 mM $(NH_4)_2SO_4$ was performed on a column of Butyl sepharose using gradient #1 described above. In FIG. 10 the purified conjugate fraction appears in fraction F2.

EXAMPLE 11

Purification of HSA:Third C34 Analogue (SEQ ID NO:8) Conjugate

The third C34 analogue is C34 (1-34) $Lys^{13}$ ($\epsilon$-AEEA-MPA)-$CONH_2$ and has the following structure:

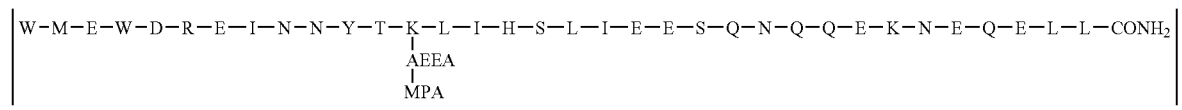

Figure 11:
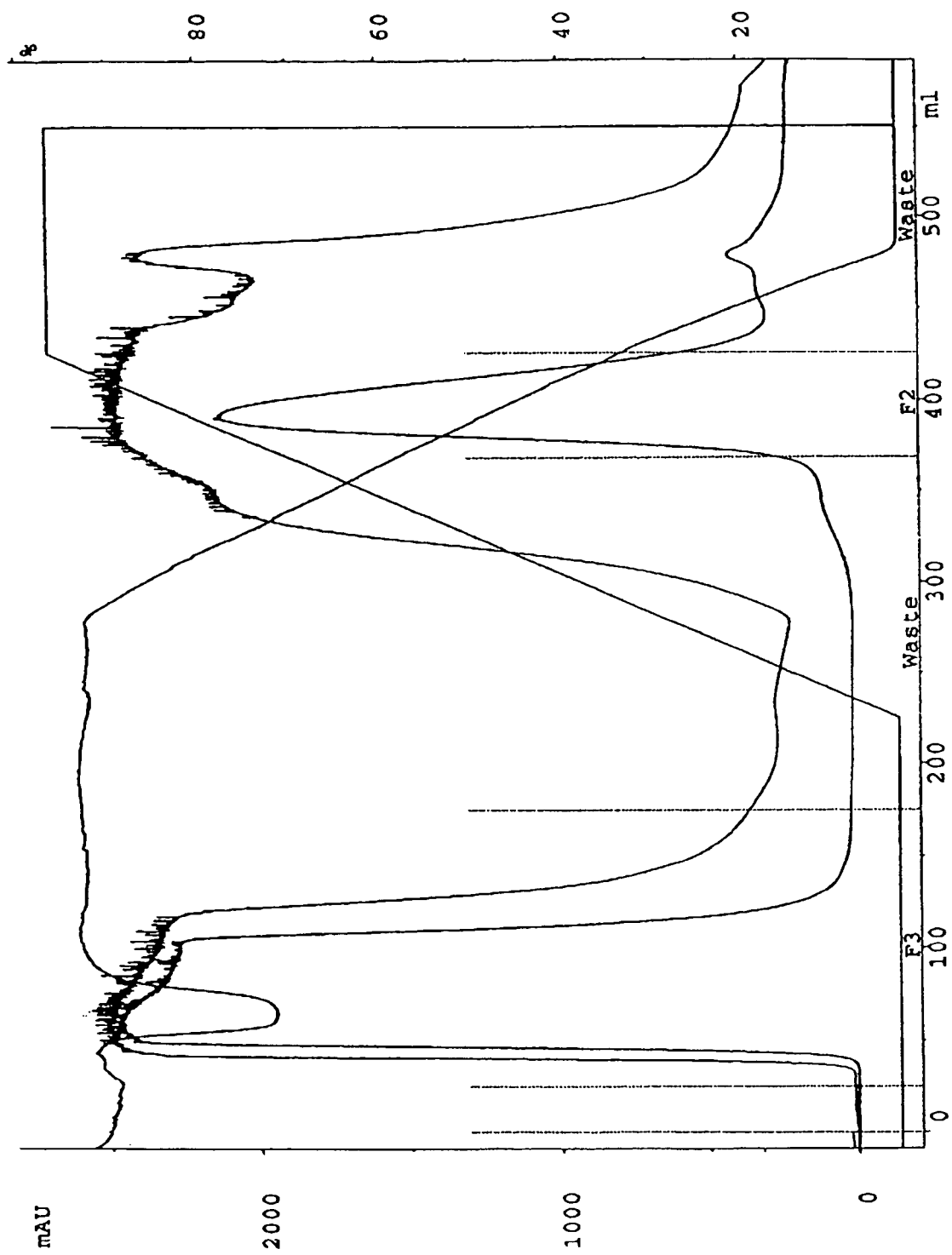
FIG. 11 illustrates the purification of the conjugate HSA: third C34 analogue (SEQ ID NO:8) by a preferred embodiment of the method of the present invention.

The purification of a conjugate made from reacting 5 ml 25% 250 mg/ml HSA (Cortex-Biochem, San Leandro, Calif.) with 1 mM third C34 analogue diluted into 20 ml of 20 mM sodium phosphate buffer (pH 7.0), 5 mM sodium caprylate and 750 mM $(NH_4)_2SO_4$, was performed on a column of Butyl sepharose using gradient #1 described above. In FIG. 11 the purified conjugate fraction appears in fraction F2.

EXAMPLE 12

Purification of l-Cysteine

Figure 12:
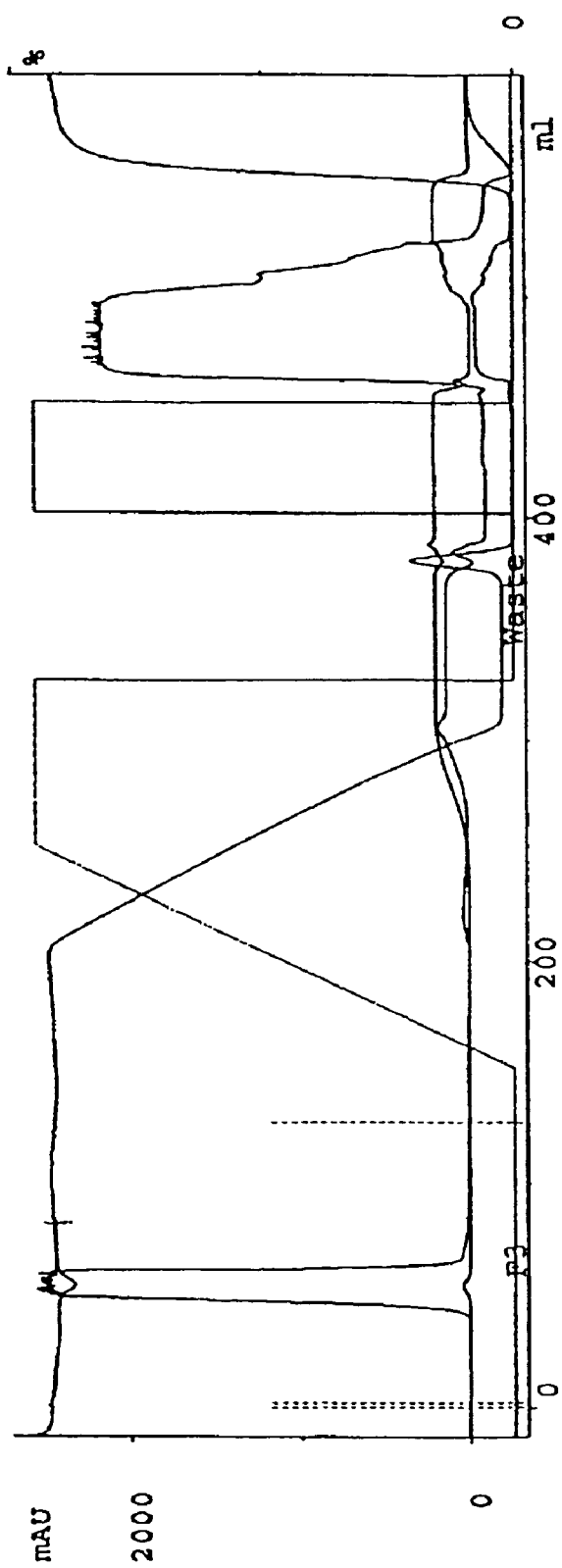
FIG. 12 illustrates the purification of L-cysteine by a preferred embodiment of the method of the present invention.

The purification of 121 mg of l-cysteine in 2 ml of a buffer made of 20 mM sodium phosphate, 5 mM sodium caprylate and 750 mM $(NH_4)_2SO_4$, was performed on a column of Butyl sepharose using the gradient #5 described above. FIG. 12 illustrates the separation curve obtained, where L-cysteine elutes within the void volume of the column (F3).

EXAMPLE 13

Purification of L-Cysteine: First GLP-1 Analogue (SEQ ID NO:1) Conjugate

The first GLP-1 analogue is GLP-1 (7-36) $dAla^8$ $Lys^{37}$ ($\epsilon$-AEEA-MPA)-$CONH_2$ and his sequence is shown above in Example 1.

Figure 13:
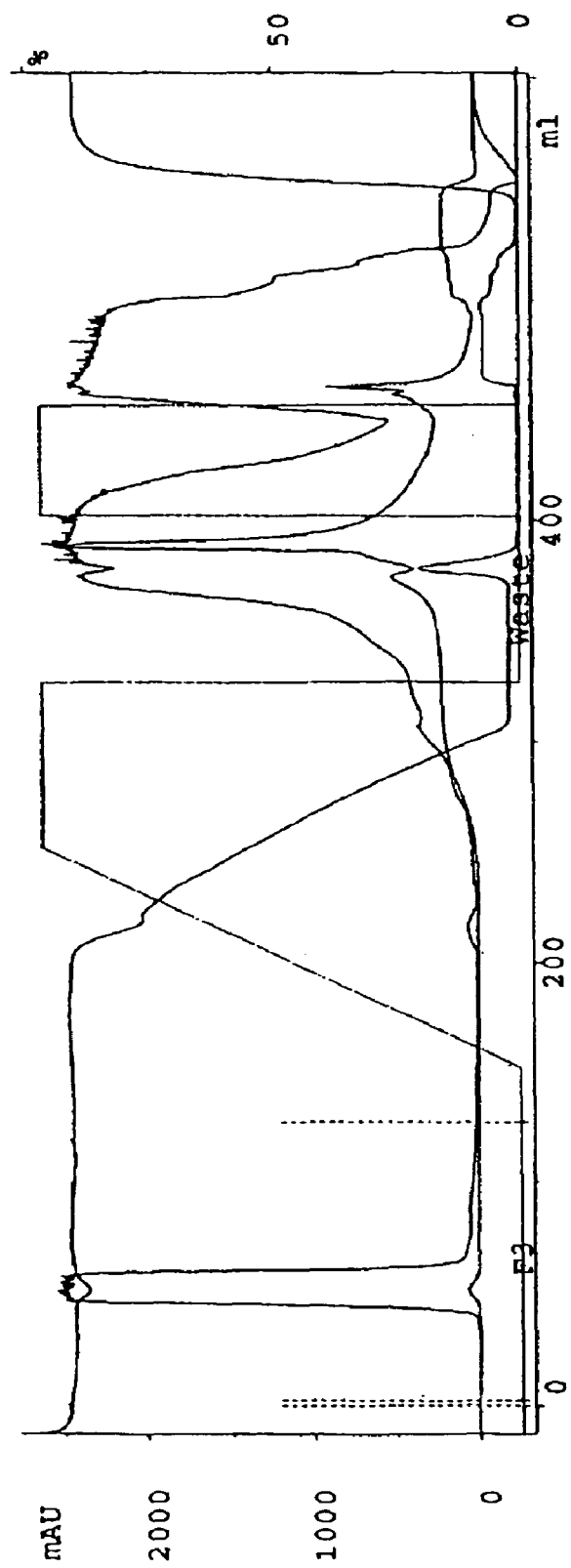
FIG. 13 illustrates the purification of L-cysteine: first GLP-1 analogue (SEQ ID NO:1) by a preferred embodiment of the method of the present invention.

The purification of a conjugate made from reacting 121 mg L-cysteine with 36.36 mg first GLP-1 analogue diluted into 2 ml of 20 mM sodium phosphate buffer (pH 7.0), 5 mM sodium caprylate and 750 mM $(NH_4)_2SO_4$ was performed on a column of Butyl sepharose using gradient #5 described above. FIG. 13 illustrates the separation curve obtained where the excess L-cysteine elutes in F3 (column void volume) and the L-Cysteine:first GLP-1 analogue conjugate elutes in 0 mM $(NH_4)_2SO_4$.

EXAMPLE 14

Purification of HSA:Second GLP-1 Analogue (SEQ ID NO:9) Conjugate

The second GLP-1 analogue is GLP-1 (7-36) $Lys^{37}$ ($\epsilon$-MPA)-$NH_2$ and has the following sequence:

HAEGTFTSDVSSYLEGQAAKEFIAWLVKGRK(ε-MPA)

Figure 14:
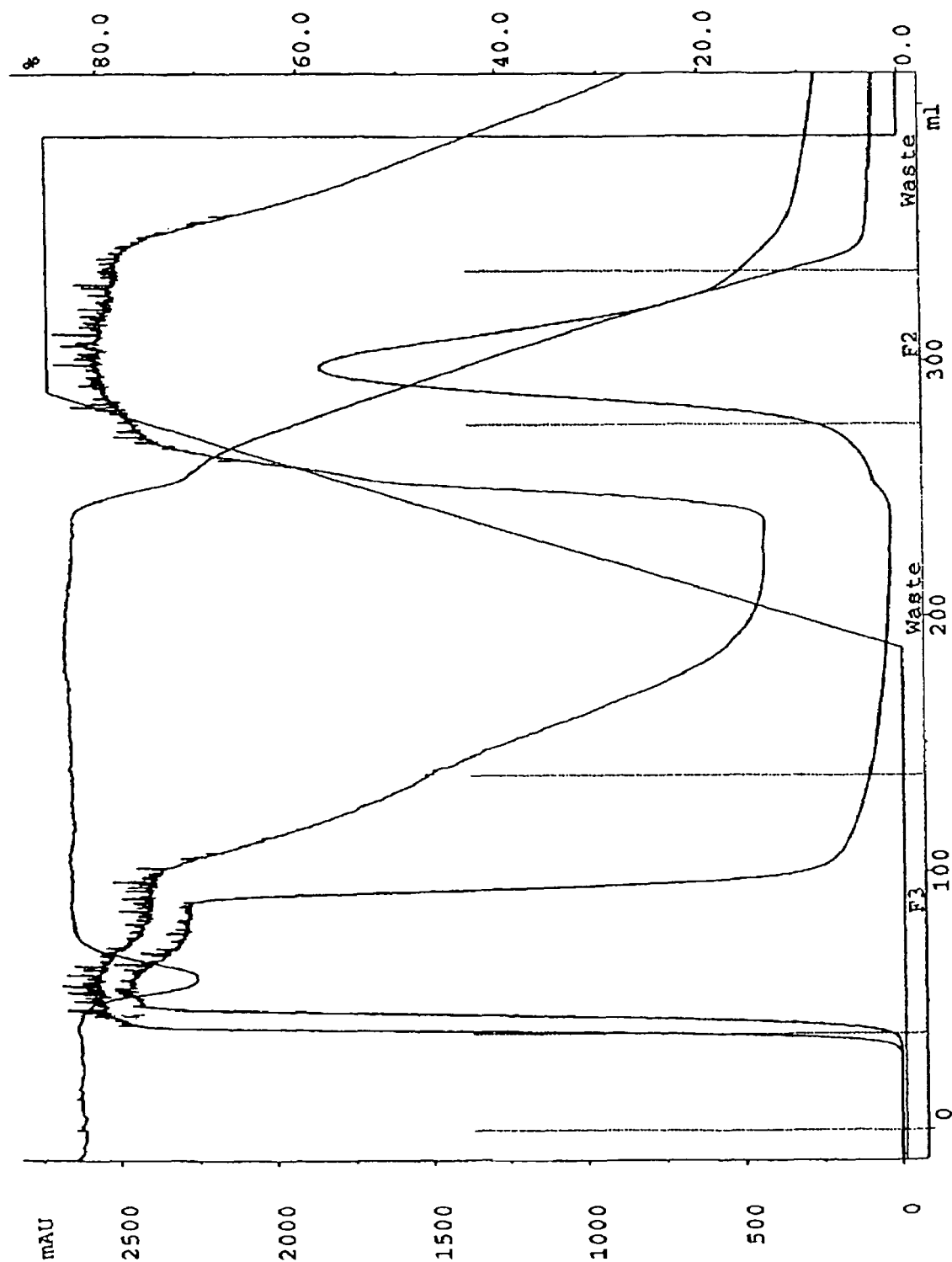
FIG. 14 illustrates the purification of the conjugate HSA: second GLP-1 analogue (SEQ ID NO:9) by a preferred embodiment of the method of the present invention.

The purification of a conjugate made from reacting 2.5 ml 25% 250 mg/ml HSA (Cortex-Biochem, San Leandro, Calif.) with 1 mM second GLP-1 analogue diluted into 10 ml of 20 mM sodium phosphate buffer (pH 7.0), 5 mM sodium caprylate and 750 mM $(NH_4)_2SO_4$ was performed on a column of Butyl sepharose using gradient #5 described above. In FIG. 14 the purified conjugate fraction appears in fraction F2.

EXAMPLE 15

Purification of HSA:Third GLP-1 Analogue (SEQ ID NO:10) Conjugate

Figure 15:
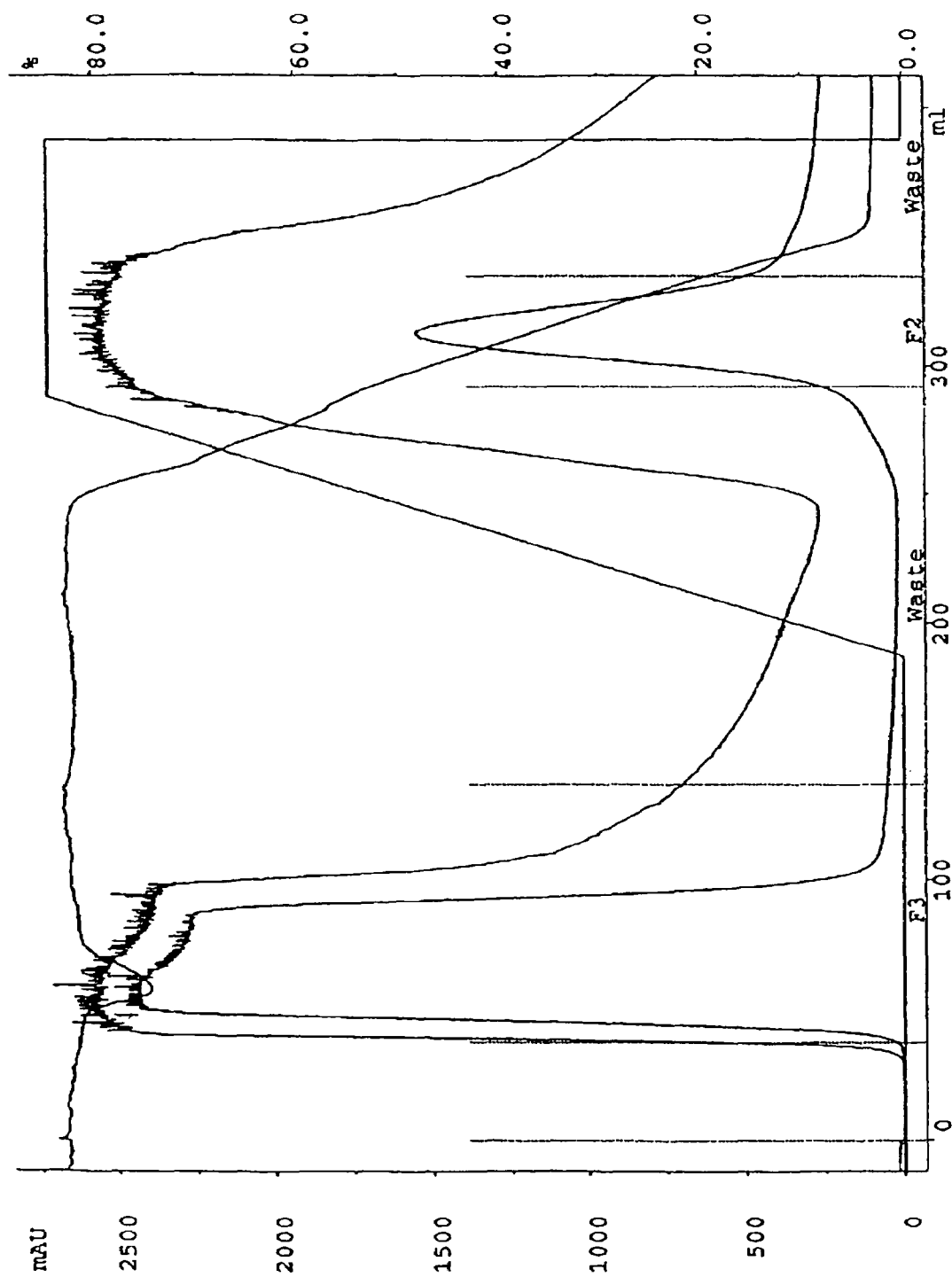
FIG. 15 illustrates the purification of the conjugate HSA: third GLP-1 analogue (SEQ ID NO:10) by a preferred embodiment of the method of the present invention.

The third GLP-1 analogue is GLP-1 (7-36) dAla$^8$ Lys$^{37}$ (ε-MPA)-NH$_2$ and has the following sequence:
H(dA)EGTFTSDVSSYLEGQAAKEFIAWLVKGRK(MPA)-CONH$_2$ The purification of a conjugate made from reacting 2.5 ml 25% 250 mg/ml HSA (Cortex-Biochem, San Leandro, Calif.) with 1 mM third GLP-1 analogue diluted into 10 ml of 20 mM sodium phosphate buffer (pH 7.0), 5 mM sodium caprylate and 750 mM $(NH_4)_2SO_4$ was performed on a column of Butyl sepharose using gradient #5 described above. In FIG. 15 the purified conjugate fraction appears in fraction F2.

EXAMPLE 16

Purification of HSA:Fourth GLP-1 Analogue (SEQ ID NO:11) Conjugate

Figure 16:
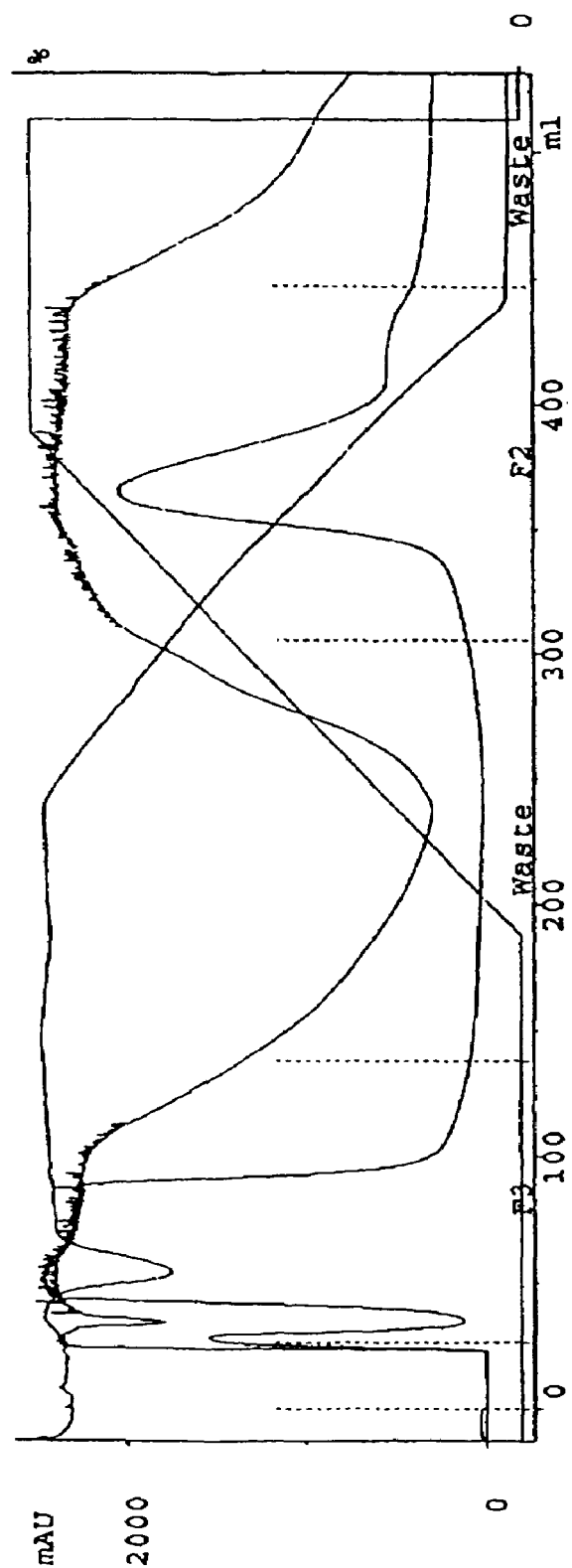
FIG. 16 illustrates the purification of the conjugate HSA: fourth GLP-1 analogue (SEQ ID NO:11) by a preferred embodiment of the method of the present invention.

The fourth GLP-1 analogue is GLP-1 (7-36) Lys$^{26}$ (ε-AEEA-AEEA-MPA) and has the following sequence:
HAEGTFTSDVSSYLEGQAAK(ε-AEEA-AEEA-MPA)EFIAWLVKGR The purification of a conjugate made from reacting 2.5 ml 25% 250 mg/ml HSA (Cortex-Biochem, San Leandro, Calif.) with 1 mM fourth GLP-1 analogue diluted into 10 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 16 the purified conjugate fraction appears in fraction F2.

EXAMPLE 17

Purification of HSA:Fifth GLP-1 Analogue (SEQ ID NO:12) Conjugate

Figure 17:
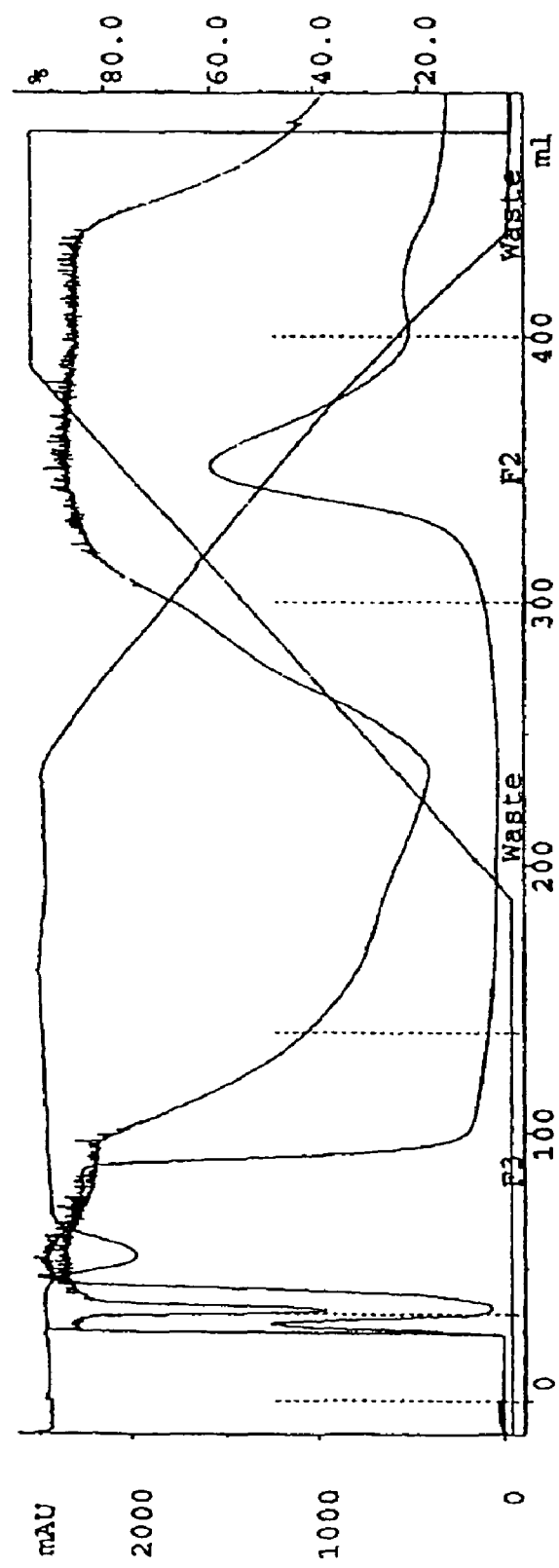
FIG. 17 illustrates the purification of the conjugate HSA: fifth GLP-1 analogue (SEQ ID NO:12) by a preferred embodiment of the method of the present invention.

The fifth GLP-1 analogue is GLP-1 (7-36) Lys$^{34}$ (ε-AEEA-AEEA-MPA) and has the following sequence:
HAEGTFTSDVSSYLEGQAAKEFIAWLVK(ε-AEEA-AEEA-MPA)GR The purification of a conjugate made from reacting 2.5 ml 25% 250 mg/ml HSA (Cortex-Biochem, San Leandro, Calif.) with 1 mM fifth GLP-1 analogue diluted into 10 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 17 the purified conjugate fraction appears in fraction F2.

EXAMPLE 18

Purification of HSA: First Exendin-4 Analogue (SEQ ID NO:13) Conjugate

Figure 18:
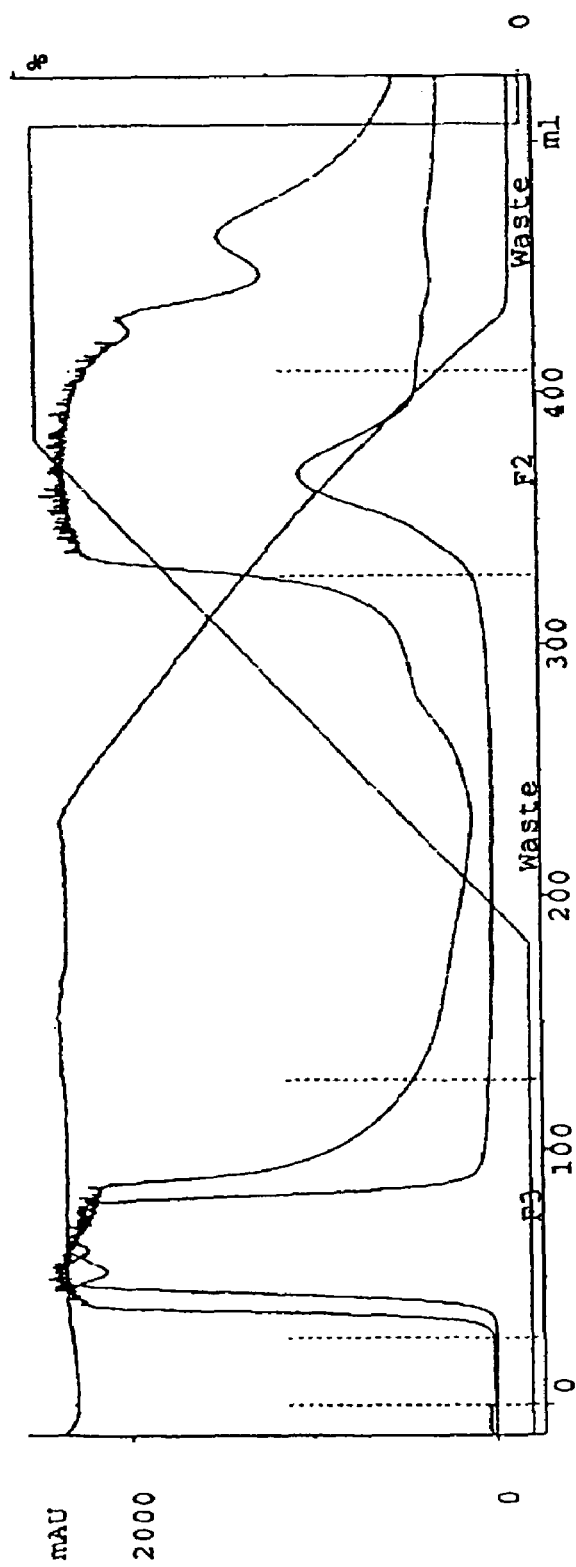
FIG. 18 illustrates the purification of the conjugate HSA: first Exendin-4 analogue (SEQ ID NO:13) by a preferred embodiment of the method of the present invention.

The first exendin-4 analogue is Exendin-4-(1-39) Lys$^{40}$ (ε-MPA)-NH$_2$ and has the following sequence:
HGEGTFTSDLSKQMEEEAVR-LFIEWLKNGGPSSGAPPPSK(ε-MPA)-CONH$_2$ The purification of a conjugate made from reacting 1 ml 25% 250 mg/ml HSA (Cortex-Biochem, San Leandro, Calif.) with 1 mM first Exendin-4 analogue diluted into 9 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 18 the purified conjugate fraction appears in fraction F2.

EXAMPLE 19

Purification of HSA:Second Exendin-4 Analogue (SEQ ID NO:14) Conjugate

Figure 19:
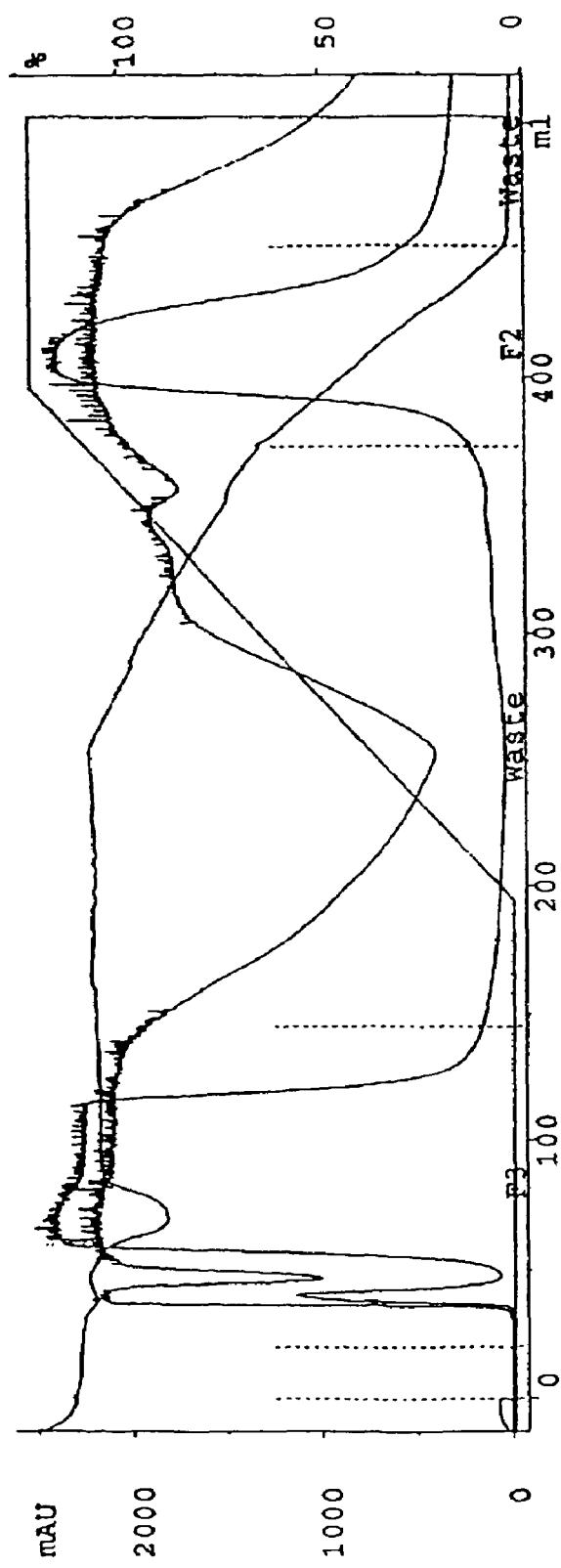
FIG. 19 illustrates the purification of the conjugate HSA: second Exendin-4 analogue (SEQ ID NO:14) by a preferred embodiment of the method of the present invention.

The second Exendin-4 analogue is Exendin-4 (9-39) Lys$^{40}$ (ε-AEEA-MPA)-CONH$_2$ and has the following sequence:
DLSKQMEEEAVRLFIEWLKNGGPSSGAPPPSK(AEEA-MPA)-CONH$_2$ The purification of a conjugate made from reacting 3.5 ml 25% HSA cortex with 1 mM second Exendin-4 analogue diluted into 21.5 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 19 the purified conjugate fraction appears in fraction F2.

EXAMPLE 20

Purification of HSA: MPA

Figure 20:
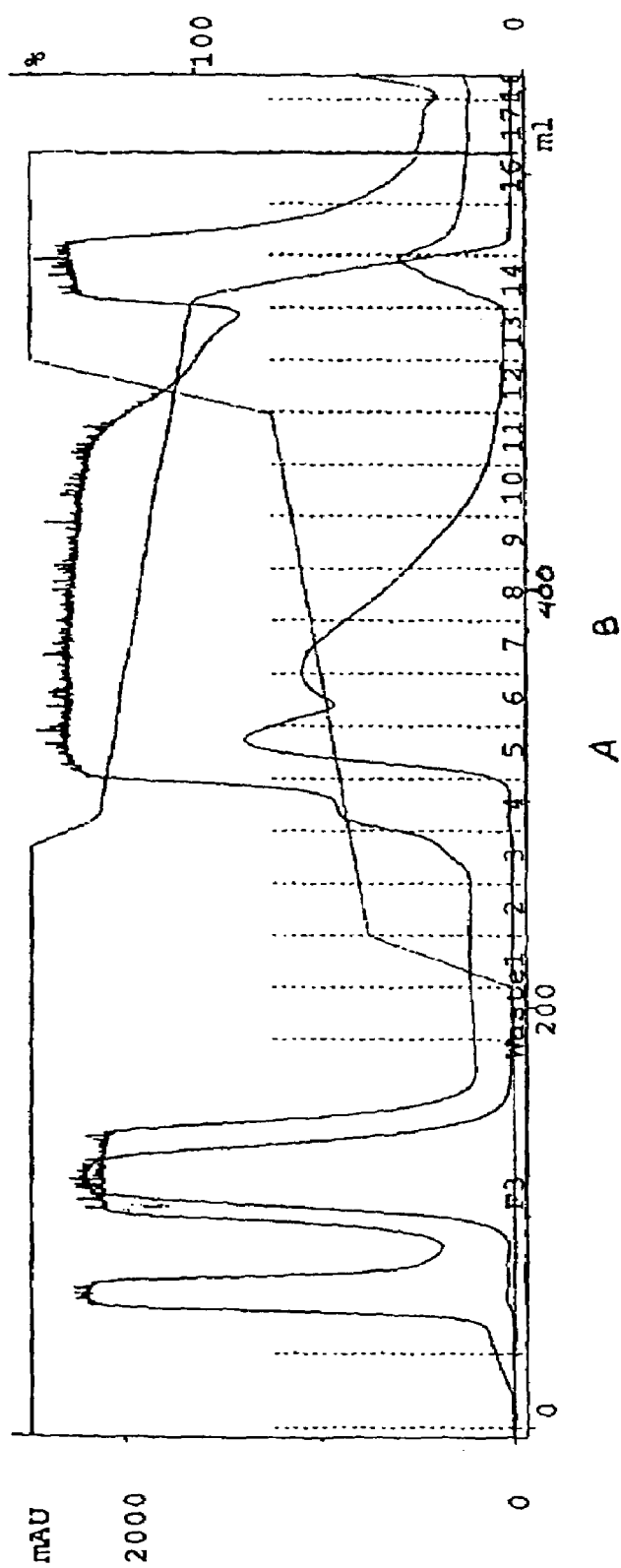
FIG. 20 illustrates the purification of HSA: MPA by a preferred embodiment of the method of the present invention.

The purification of a conjugate made from reacting 1 ml 25% 250 mg/ml HSA (Cortex-Biochem, San Leandro, Calif.) with 2 mM MPA diluted into 9 ml of 20 mM sodium phosphate buffer (pH 7.0), 5 mM sodium caprylate and 1750 mM $(NH_4)_2SO_4$ was performed on a column of Butyl sepharose using gradient #2 described above. In FIG. 20 the fraction of mercaptalbumin is in fraction A (F5) and capped albumin is in fraction B (F7-F8). The conjugate fraction was concentrated with Amicon™ filter 30 kDa.

EXAMPLE 21

Purification of HSA

Figure 21:
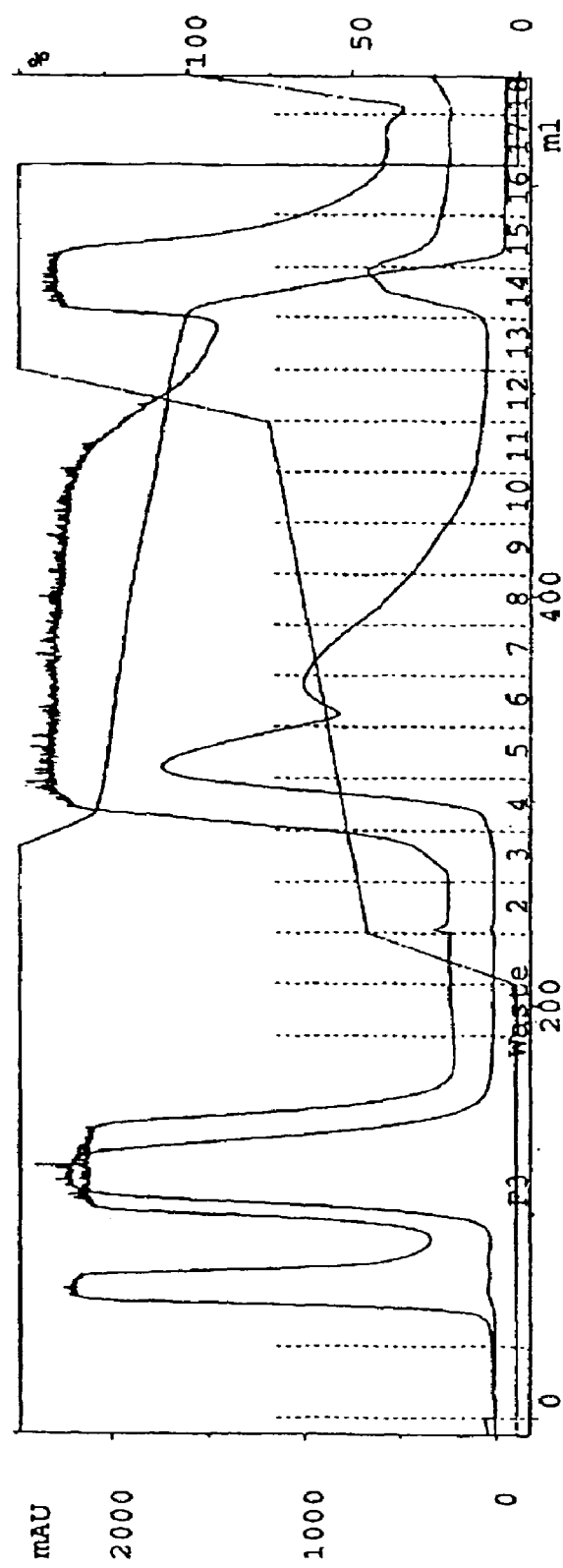
FIG. 21 illustrates the purification of HSA by a preferred embodiment of the method of the present invention.

The purification of 1 ml 25% 250 mg/ml HSA (Cortex-Biochem, San Leandro, Calif.) diluted into 9 ml of 20 mM sodium phosphate buffer (pH 7.0), 5 mM sodium caprylate and 1750 mM $(NH_4)_2SO_4$ was performed on a column of Butyl sepharose using the gradient #2 described above. When using gradient #2, unlike gradients #1 and #5, both conjugated albumin and non-conjugated albumin adsorbs onto the hydrophobic resin during sample loading. FIG. 21 illustrates the separation curve obtained where F4 and F5 are enriched in mercaptalbumin and F6, F7 and F8 are enriched in capped albumin.

EXAMPLE 22

Purification of HSA:Second C34 Analogue (SEQ ID NO:3) Conjugate

The second C34 analogue is C34 (1-34) Lys$^{35}$ ($\epsilon$-AEEA-MPA)-CONH$_2$ and his structure is shown in Example 10.

Figure 22:
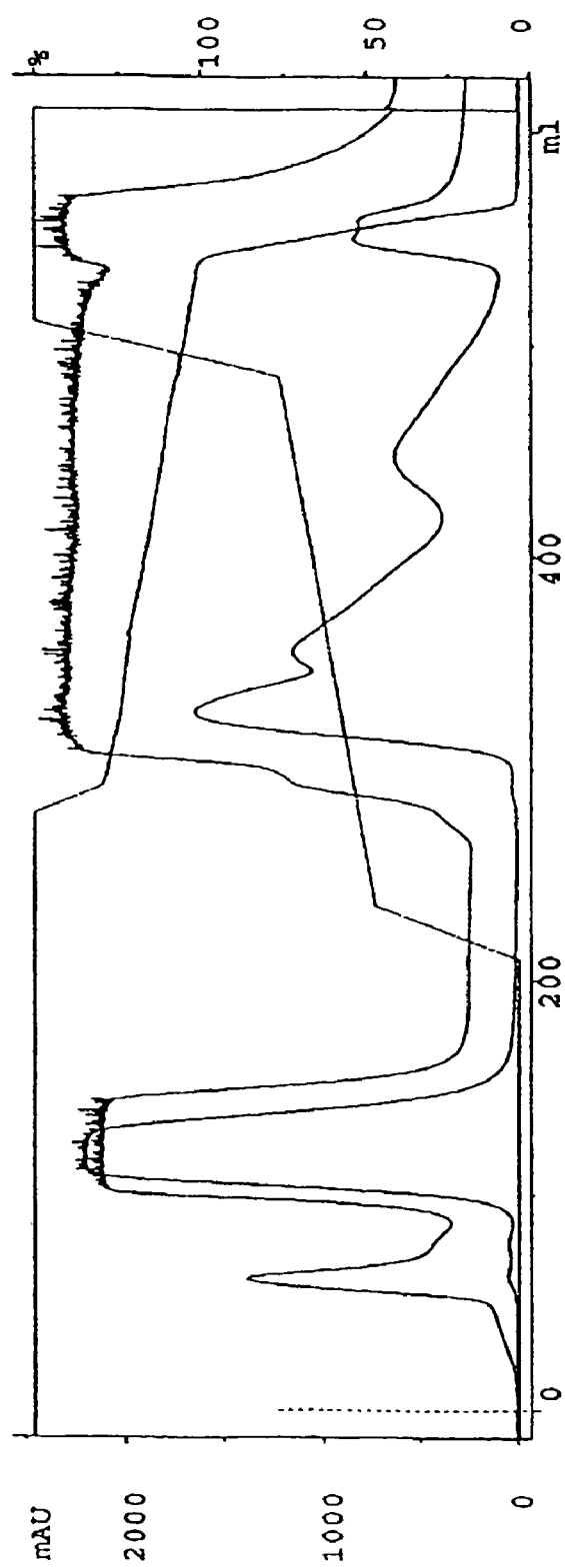
FIG. 22 illustrates the purification of the conjugate HSA: second C34 analogue (SEQ ID NO:3) by a preferred embodiment of the method of the present invention.

The purification of a conjugate made from reacting 1 ml 25% 250 mg/ml HSA (Cortex-Biochem, San Leandro, Calif.) with 1 mM second C34 analogue diluted into 9 ml of a buffer made of 20 mM sodium phosphate buffer (pH 7.0), 5 mM sodium caprylate and 1750 mM (NH$_4$)$_2$SO$_4$ was performed on a column of Butyl sepharose using gradient #2 described above. In FIG. 22 mercaptalbumin appears in fraction A (F5) and capped albumin and the purified conjugated is in fraction B (F7-F8).

EXAMPLE 23

Purification of HSA:First Dynorphin A Analogue (SEQ ID NO:15) Conjugate

The first Dynorphin A analogue is Dyn A (1-13) (MPA)-NH$_2$ and has the following sequence: YGGFLRRIRPKLK (MPA)-CONH$_2$.

Figure 23:
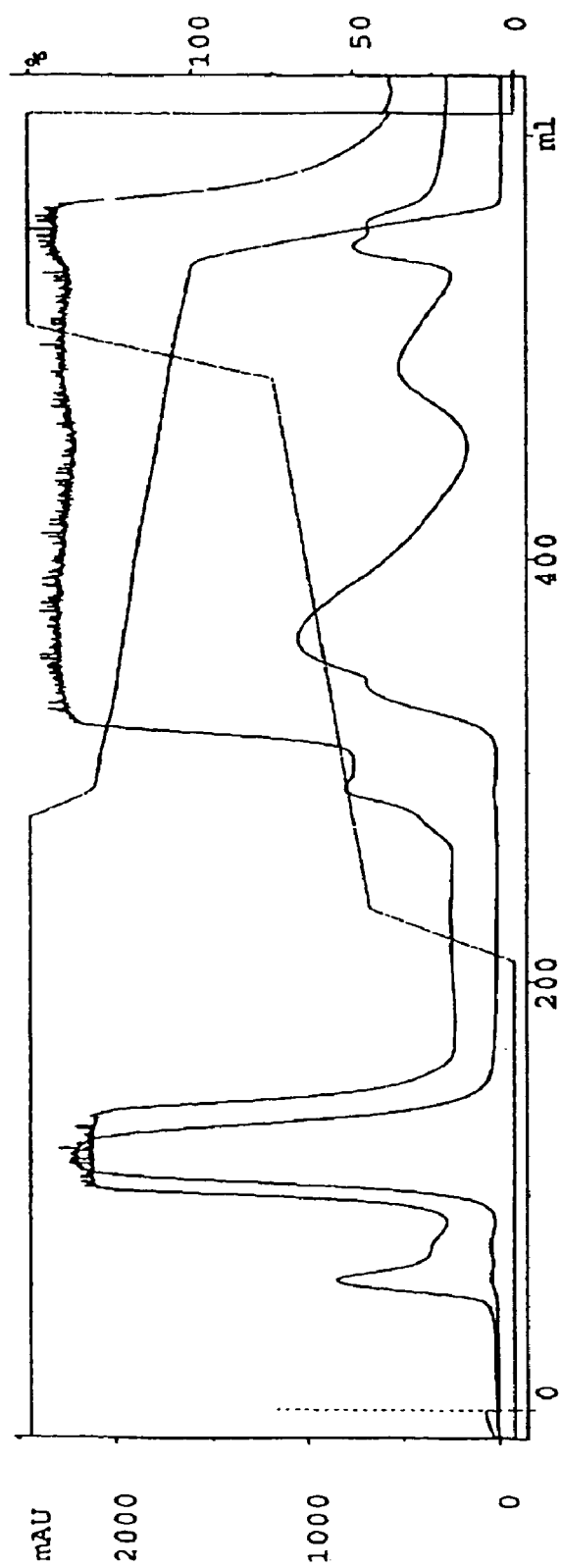
FIG. 23 illustrates the purification of the conjugate HSA: first Dynorphin A analogue (SEQ ID NO:15) by a preferred embodiment of the method of the present invention.

The purification of a conjugate made from reacting 1 ml 25% 250 mg/ml HSA (Cortex-Biochem, San Leandro, Calif.) with 1 mM first Dynorphin A analogue diluted into 9 ml of 20 mM sodium phosphate buffer (pH 7.0), 5 mM sodium caprylate and 1750 mM (NH$_4$)$_2$SO$_4$ was performed on a column of Butyl sepharose using gradient #2 described above. In FIG. 23 the purified conjugate fraction appears in fraction A (F11-F12)

EXAMPLE 24

Purification of HSA:First ANP Analogue (SEQ ID NO:16) Conjugate

The first ANP analogue is MPA-AEEA-ANP (99-126)—CONH$_2$ and has the following structure:

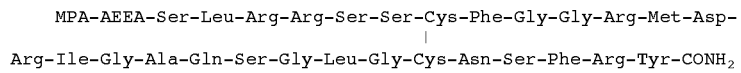

```
MPA-AEEA-Ser-Leu-Arg-Arg-Ser-Ser-Cys-Phe-Gly-Gly-Arg-Met-Asp-
                                 |
Arg-Ile-Gly-Ala-Gln-Ser-Gly-Leu-Gly-Cys-Asn-Ser-Phe-Arg-Tyr-CONH2
```

Figure 24:
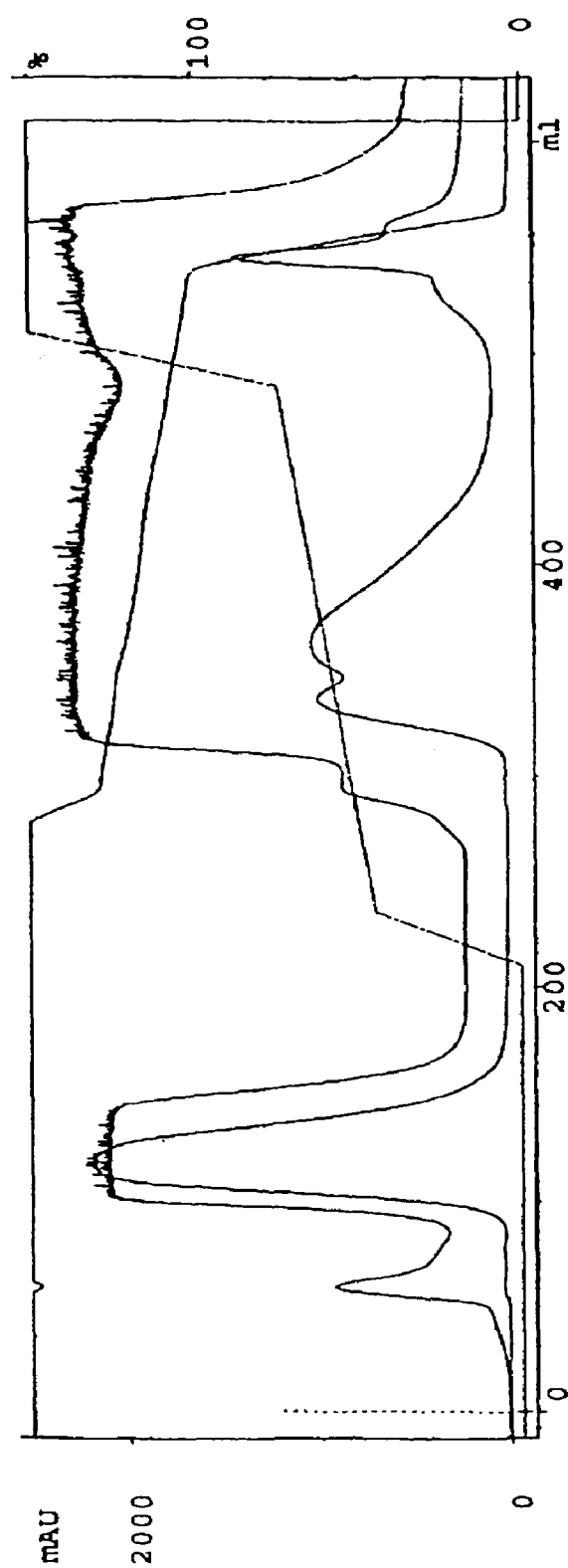
FIG. 24 illustrates the purification of the conjugate HSA: first ANP analogue (SEQ ID NO:16) by a preferred embodiment of the method of the present invention.

The purification of a conjugate made from reacting 1 ml 25% 250 mg/ml HSA (Cortex-Biochem, San Leandro, Calif.) with 1 mM first ANP analogue diluted into 9 ml of 20 mM sodium phosphate buffer (pH 7.0), 5 mM sodium caprylate and 1750 mM (NH$_4$)$_2$SO$_4$ was performed on a column of Butyl sepharose using gradient #2 described above. In FIG. 24 the purified conjugate fraction appears in fraction A (F14).

EXAMPLE 25

Purification of HSA:Second Dynorphin A Analogue (SEQ ID NO:17) Conjugate

Figure 25:
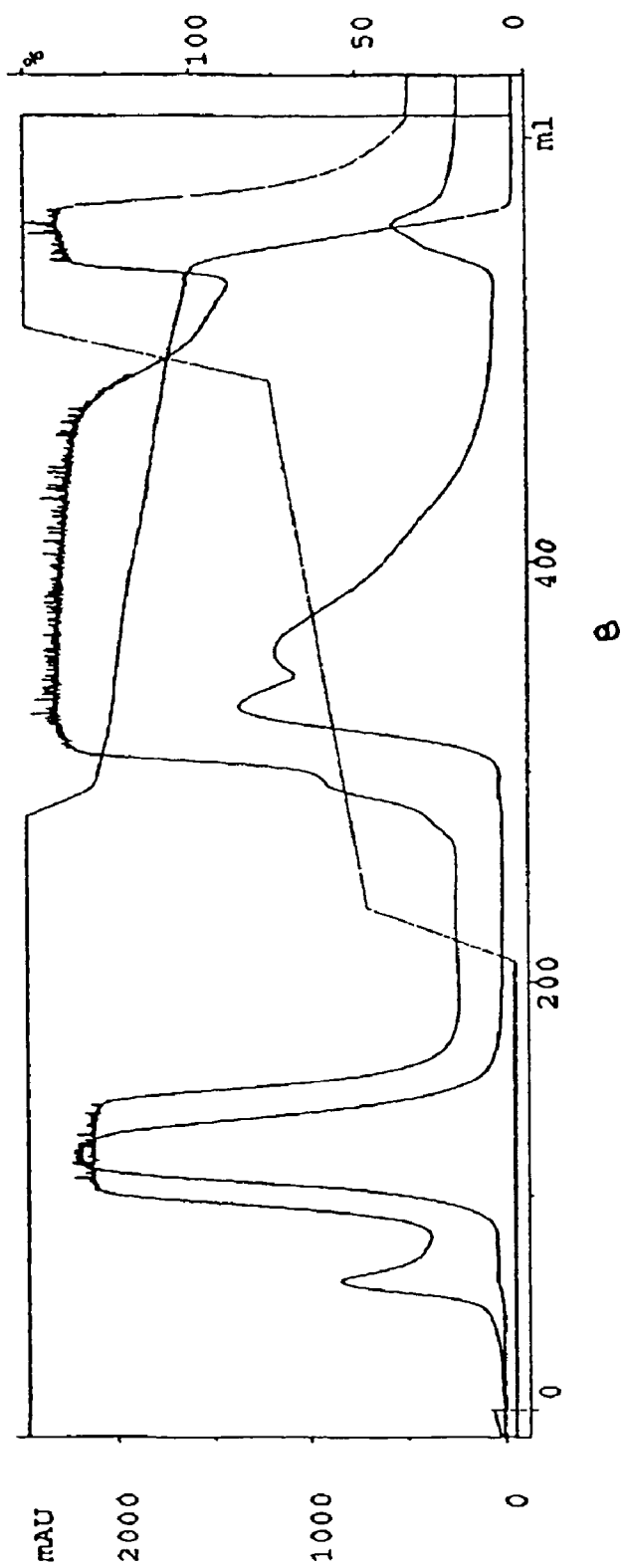
FIG. 25 illustrates the purification of the conjugate HSA: second Dynorphin A analogue (SEQ ID NO:17) by a preferred embodiment of the method of the present invention.

The second Dynorphin A analogue is Dyn A (7-13) Lys$^{13}$ ($\epsilon$-MPA)-CONH$_2$ and has the following sequence: RIRPKLK(MPA)-CONH$_2$ The purification of a conjugate made from reacting 1 ml 25% 250 mg/ml HSA (Cortex-Biochem, San Leandro, Calif.) with 1 mM second Dynorphin A analogue diluted into 9 ml of 20 mM sodium phosphate buffer (pH 7.0), 5 mM sodium caprylate and 1750 mM (NH$_4$)$_2$SO$_4$ was performed on a column of Butyl sepharose using gradient #2 described above. In FIG. 25 the purified conjugate fraction appears in fraction A (F9).

EXAMPLE 26

Purification of HSA: ACE Inhibitor (SEQ ID NO:18) Conjugate

The ACE inhibitor used in this example is acetyl-Phe-His-cyclohexylstatyl-Ile-Lys ($\epsilon$-AEEA-MPA)-CONH$_2$ and has the following sequence:

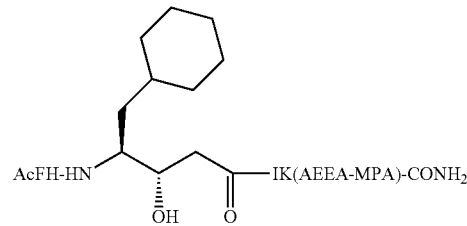

Figure 26:
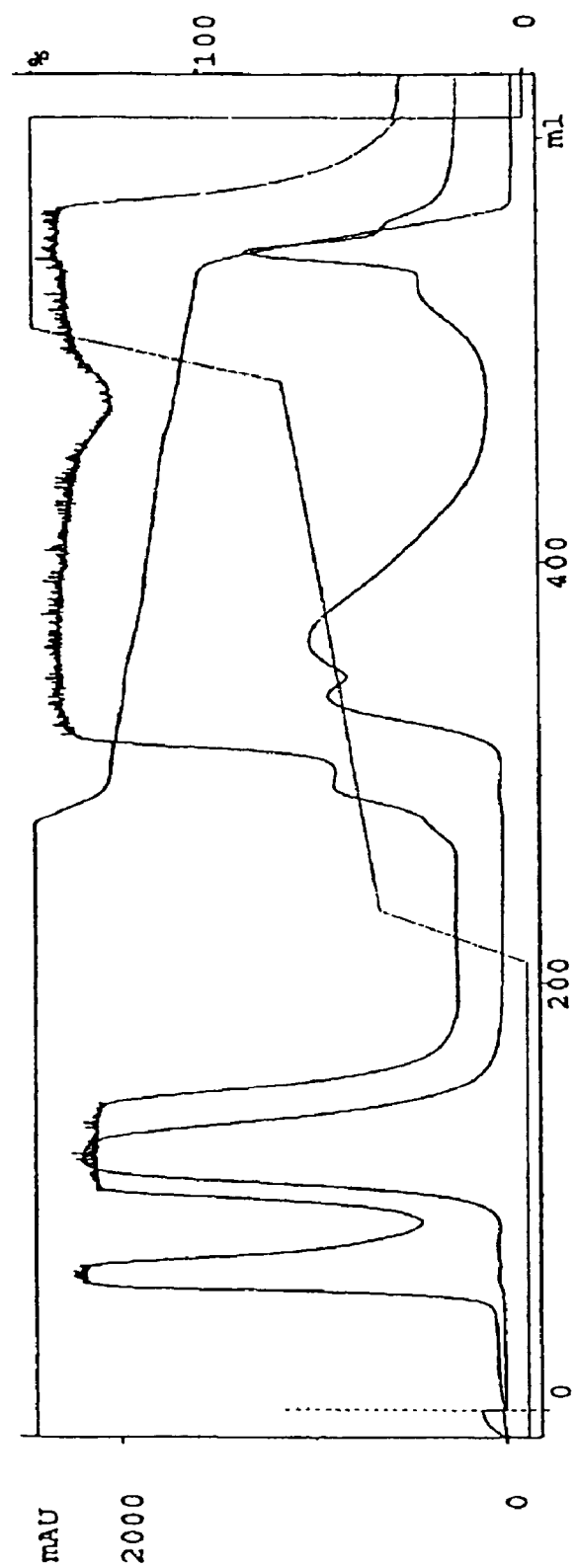
FIG. 26 illustrates the purification of the conjugate HSA: ACE inhibitor (SEQ ID NO:18) by a preferred embodiment of the method of the present invention.

The purification of a conjugate made from reacting 1 ml 25% 250 mg/ml HSA (Cortex-Biochem, San Leandro, Calif.) with 1 mM ACE inhibitor diluted into 9 ml of 20 mM sodium phosphate buffer (pH 7.0), 5 mM sodium caprylate and 1750 mM (NH$_4$)$_2$SO$_4$ was performed on a column of Butyl sepharose using gradient #2 described above. In FIG. 26 the purified conjugate fraction appears in fraction A (F14).

EXAMPLE 27

Purification of HSA: Sixth GLP-1 Analogue (SEQ ID NO:19) Conjugate

The sixth GLP-1 analogue is GLP-1 (7-36) Lys$^{23}$ ($\epsilon$-AEEA-MPA)-CONH$_2$ and has the following sequence:

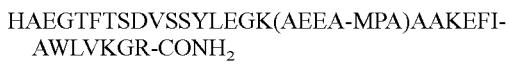

HAEGTFTSDVSSYLEGK(AEEA-MPA)AAKEFI-AWLVKGR-CONH$_2$

Figure 27:
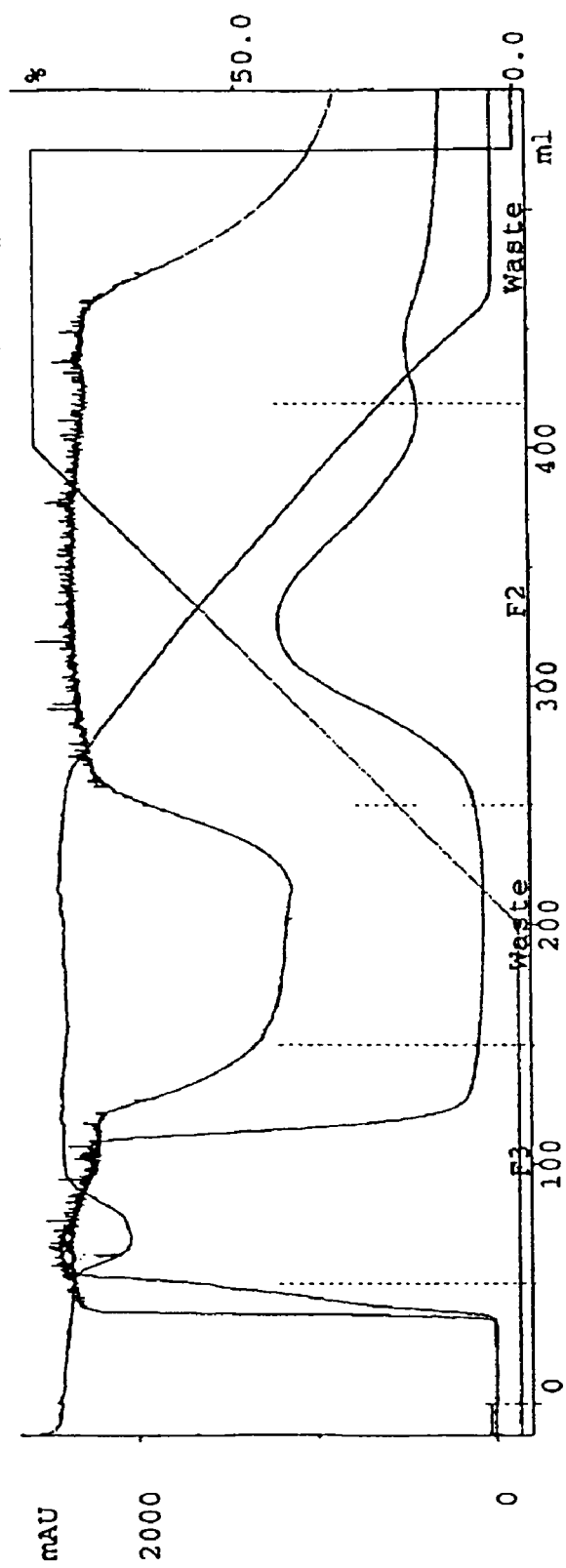
FIG. 27 illustrates the purification of the conjugate HSA: sixth GLP-1 analogue (SEQ ID NO:19) by a preferred embodiment of the method of the present invention.

The purification of a conjugate made from reacting 3 ml 25% 250 mg/ml HSA (Cortex-Biochem, San Leandro, Calif.) with 1 mM sixth GLP-1 analogue diluted into 22 ml of 20 mM sodium phosphate buffer (pH 7.0), 5 mM sodium caprylate and 1750 mM (NH$_4$)$_2$SO$_4$ was performed on a column of Butyl sepharose using gradient #1 described above. In FIG. 27 the purified conjugate fraction appears in fraction F2.

EXAMPLE 28

Purification of HSA: Seventh GLP-1 Analogue (SEQ ID NO:20) Conjugate

The seventh GLP-1 analogue is GLP-1 (7-36) Lys$^{18}$ ($\epsilon$-AEEA-MPA)-CONH$_2$ and has the following sequence:
HAEGTFTSDVSK(AEEA-MPA)YLEGQAAKEFI-AWLVKGR-CONH$_2$

Figure 28:
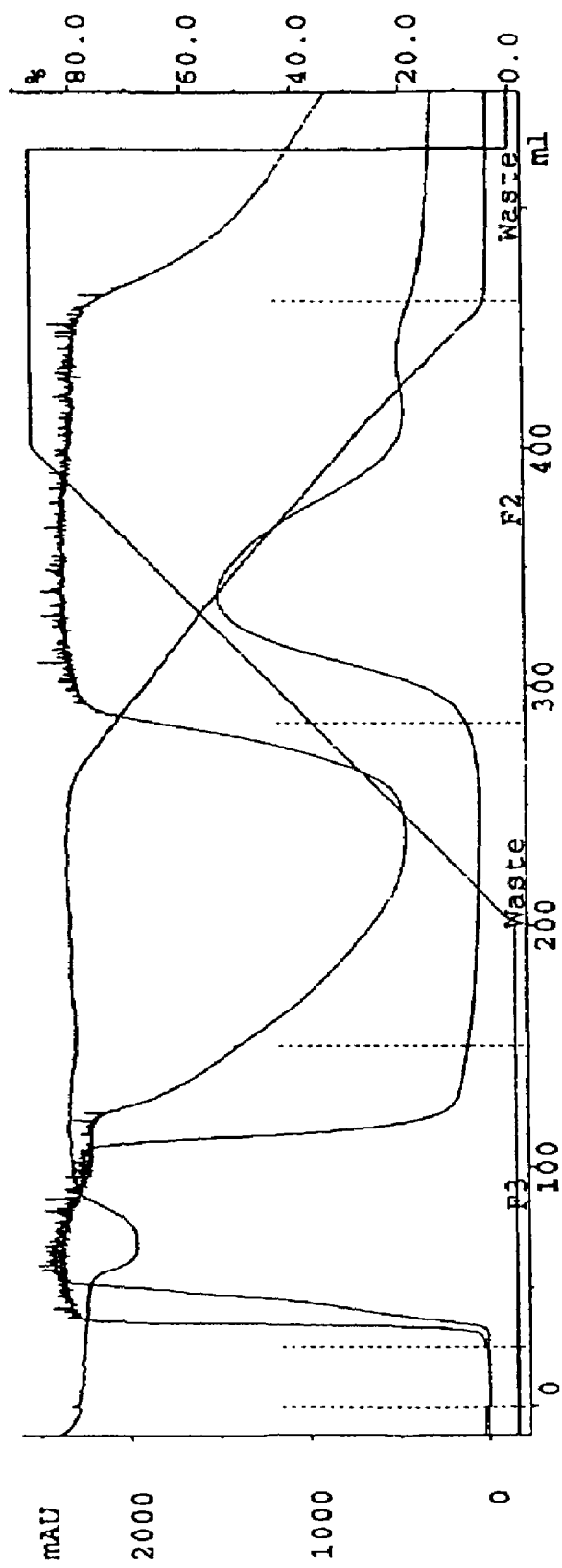
FIG. 28 illustrates the purification of the conjugate HSA: seventh GLP-1 analogue (SEQ ID NO:20) by a preferred embodiment of the method of the present invention.

The purification of a conjugate made from reacting 3 ml 25% 250 mg/ml HSA (Cortex-Biochem, San Leandro, Calif.) with 1 mM seventh GLP-1 analogue diluted into 22 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 28 the purified conjugate fraction appears in fraction F2.

EXAMPLE 29

Purification of HSA: Eighth GLP-1 Analogue (SEQ ID NO:21) Conjugate

Figure 29:
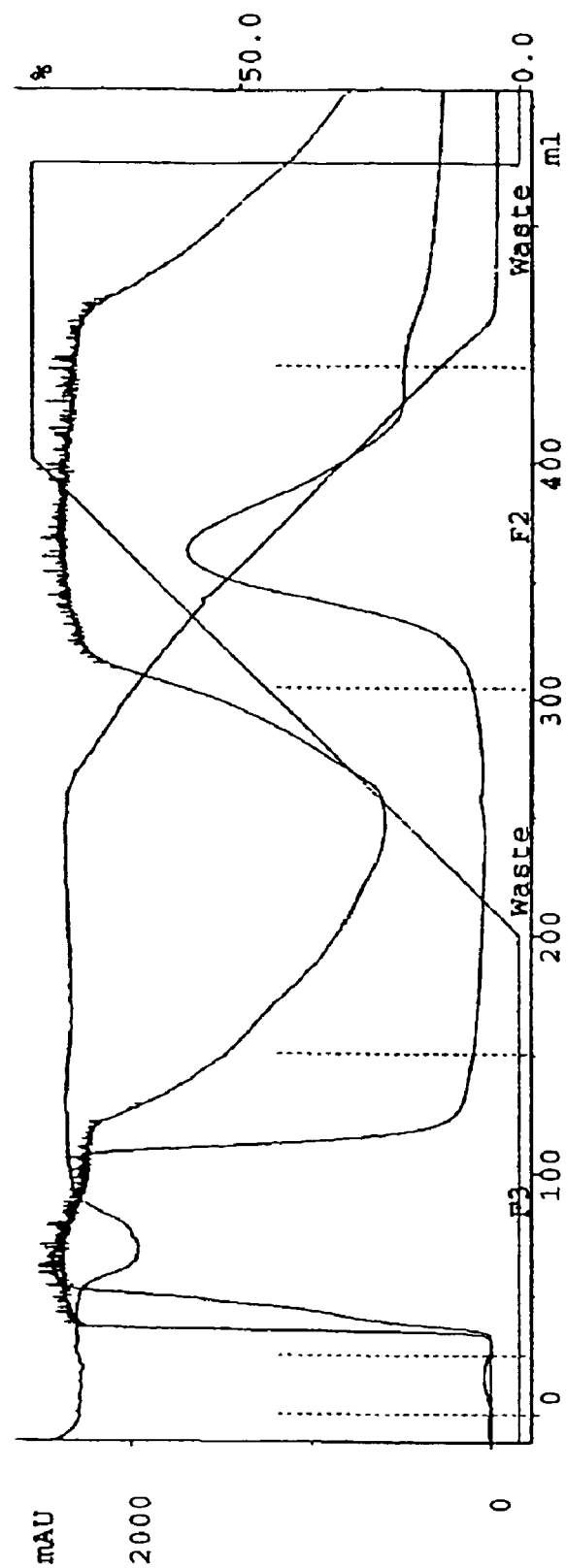
FIG. 29 illustrates the purification of the conjugate HSA: eighth GLP-1 analogue (SEQ ID NO:21) by a preferred embodiment of the method of the present invention.

The eighth GLP-1 analogue is GLP-1 (7-36) $Lys^{26}$ ($\epsilon$-AEEA-MPA)-$CONH_2$ and has the following sequence:
HAEGTFTSDVSSYLEGQAAK(AEEA-MPA)EFI-AWLVKGR-$CONH_2$ The purification of a conjugate made from reacting 2.5 ml 25% 250 mg/ml HSA (Cortex-Biochem, San Leandro, Calif.) with 1 mM eighth GLP-1 analogue diluted into 22.5 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 29 the purified conjugate fraction appears in fraction F2.

EXAMPLE 30

Purification of HSA:Ninth GLP-1 Analogue (SEQ ID NO:22) Conjugate

Figure 30:
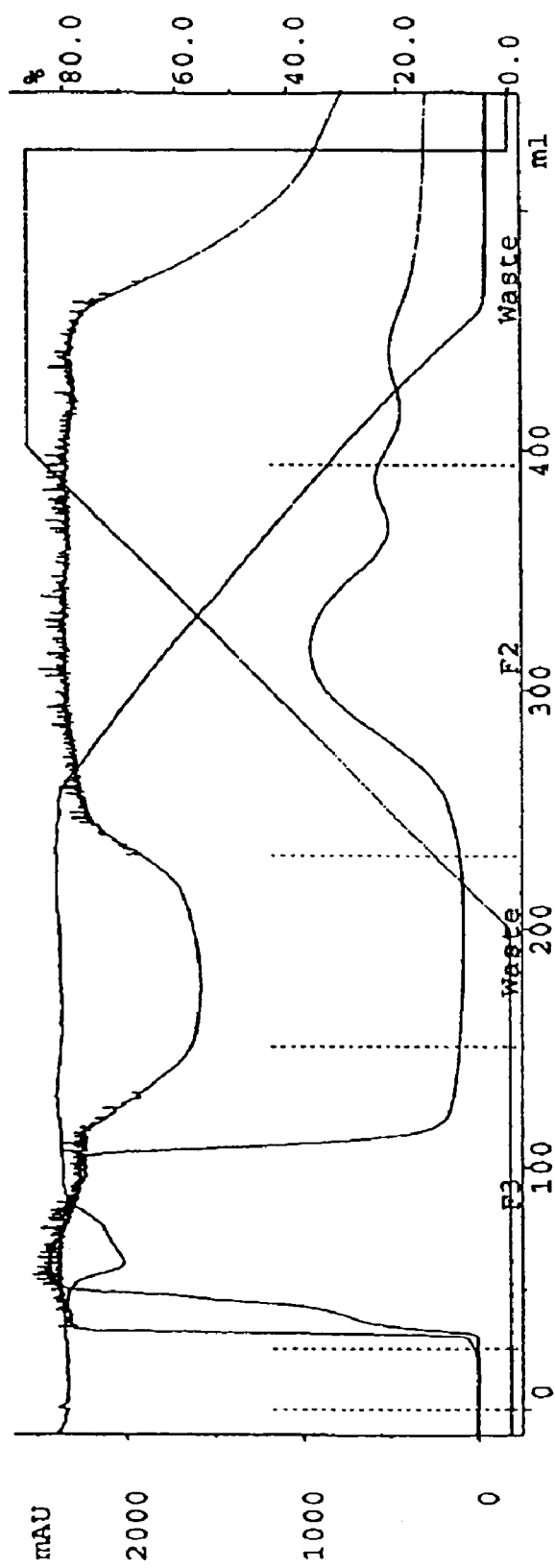
FIG. 30 illustrates the purification of the conjugate HSA: ninth GLP-1 analogue (SEQ ID NO:22) by a preferred embodiment of the method of the present invention.

The ninth GLP-1 analogue is GLP-1 (7-37) $Lys^{27}$ ($\epsilon$-AEEA-MPA)-$CONH_2$ and has the following sequence:
HAEGTFTSDVSSYLEGQAAKK(AEEA-MPA)FI-AWLVKGR-$CONH_2$ The purification of a conjugate made from reacting 3 ml 25% 250 mg/ml HSA (Cortex-Biochem, San Leandro, Calif.) with 1 mM ninth GLP-1 analogue diluted into 22 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 30 the purified conjugate fraction appears in fraction F2.

EXAMPLE 31

Purification of HSA: Tenth GLP-1 Analogue (SEQ ID NO:23) Conjugate

Figure 31:
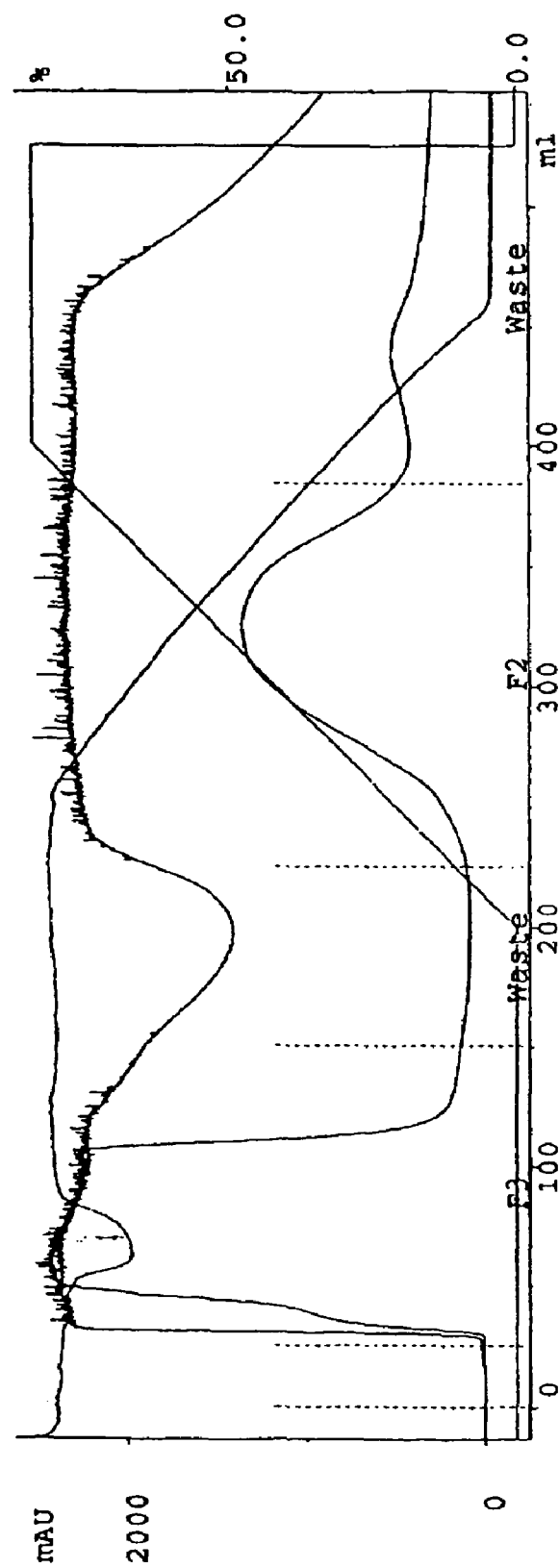
FIG. 31 illustrates the purification of the conjugate HSA: tenth GLP-1 analogue (SEQ ID NO:23) by a preferred embodiment of the method of the present invention.

The tenth GLP-1 analogue is GLP-1 (7-36) $Lys^{37}$ ($\epsilon$-AEEA-AEEA-MPA)-$CONH_2$ and has the following sequence:
HAEGTFTSDVSSYLEGQAAKEFIAWLVKGRK-AEEA-AEEA-MPA-$CONH_2$ The purification of a conjugate made from reacting 2.5 ml 25% 250 mg/ml HSA (Cortex-Biochem, San Leandro, Calif.) with 1 mM tenth GLP-1 analogue diluted into 22.5 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 31 the purified conjugate fraction appears in fraction F2.

EXAMPLE 32

Purification of HSA: Eleventh GLP-1 Analogue (SEQ ID NO:24) Conjugate

Figure 32:
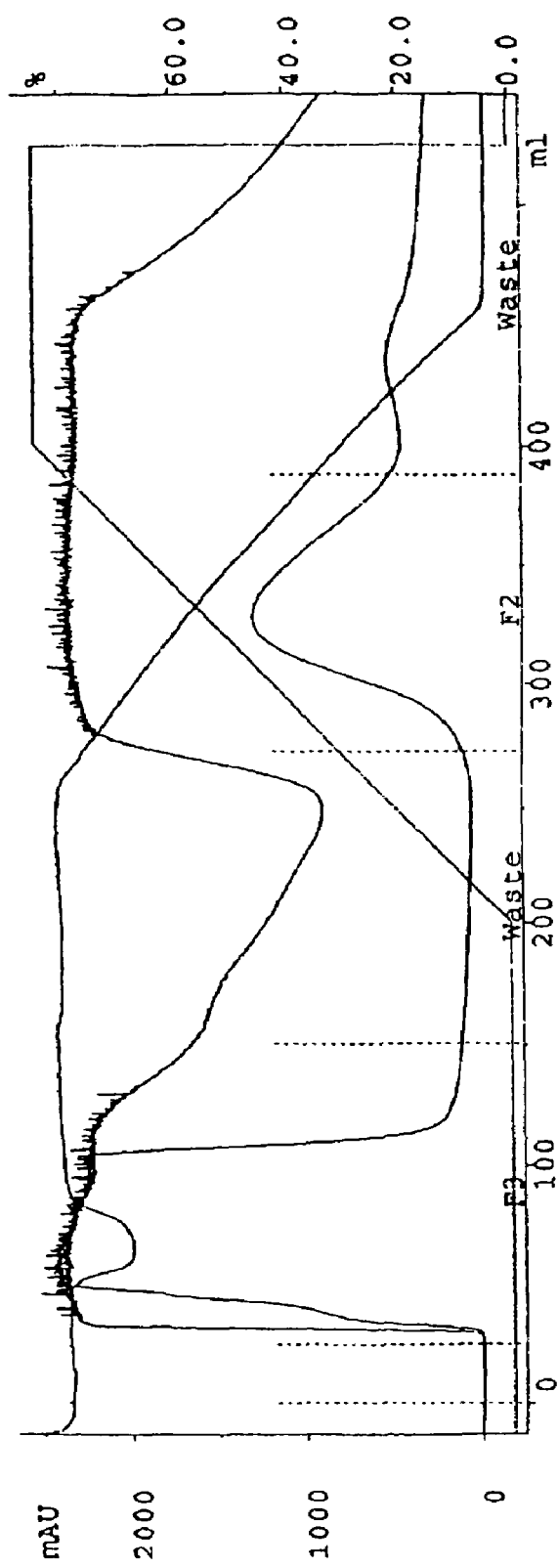
FIG. 32 illustrates the purification of the conjugate HSA: eleventh GLP-1 analogue (SEQ ID NO:24) by a preferred embodiment of the method of the present invention.

The eleventh GLP-1 analogue is GLP-1 (7-36) $Lys^{37}$ ($\epsilon$-AEEA-MPA)-$CONH_2$ and has the following sequence:
HAEGTFTSDVSSYLEGQAAKEFIAWLVKGRK (AEEA-MPA)-$CONH_2$ The purification of a conjugate made from reacting 2.5 ml 25% 250 mg/ml HSA (Cortex-Biochem, San Leandro, Calif.) with 1 mM eleventh GLP-1 analogue diluted into 22.5 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 32 the purified conjugate fraction appears in fraction F2.

EXAMPLE 33

Purification of HSA: Third Exendin-4 Analogue (SEQ ID NO:25) Conjugate

Figure 33:
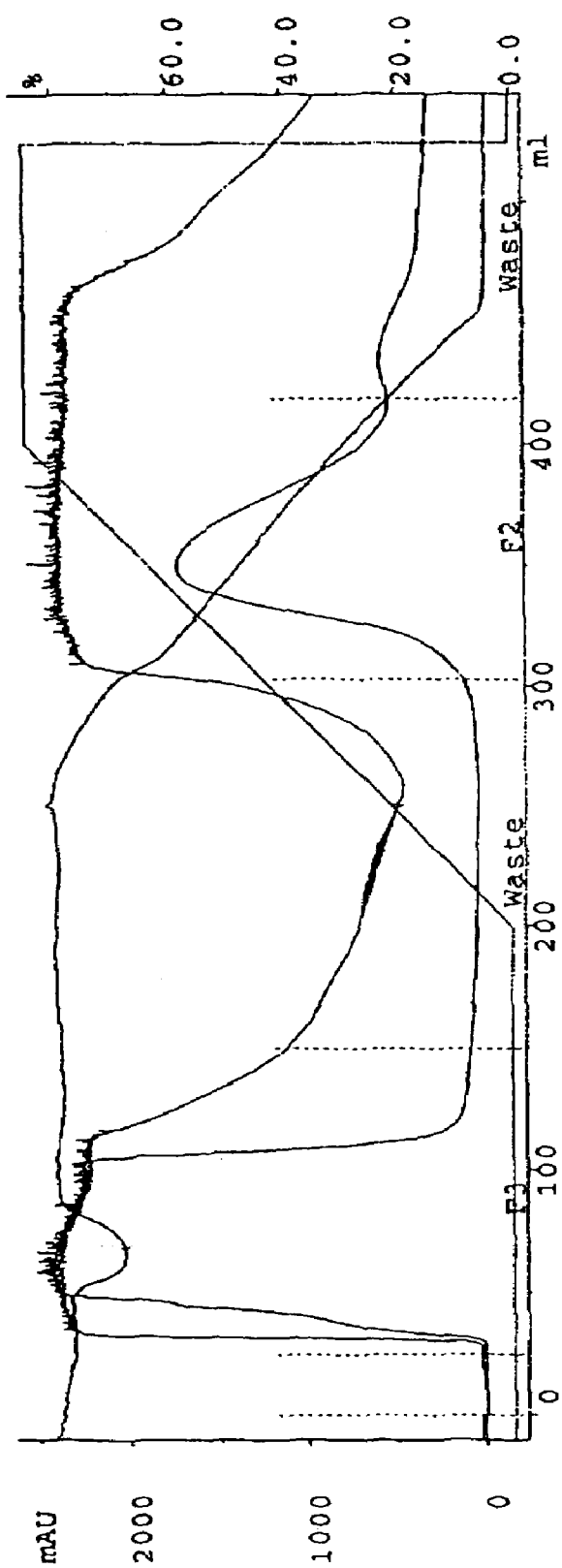
FIG. 33 illustrates the purification of the conjugate HSA: third Exendin-4 analogue (SEQ ID NO:25) by a preferred embodiment of the method of the present invention.

The third Exendin-4 analogue is Exendin-4-(1-39) $Lys^{40}$ ($\epsilon$-AEEA-MPA)-$CONH_2$ and has the following sequence:
HGEGTFTSDLSKQMEEEAVR-LFIEWLKNGGPSSGAPPPSK($\epsilon$-AEEA-MPA)-$CONH_2$ The purification of a conjugate made from reacting 2.5 ml 25% 250 mg/ml HSA (Cortex-Biochem, San Leandro, Calif.) with 1 mM third Exendin-4 analogue diluted into 22.5 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 33 the purified conjugate fraction appears in fraction F2.

EXAMPLE 34

Purification of HSA: Twelfth GLP-1 Analogue (SEQ ID NO:26) Conjugate

Figure 34:
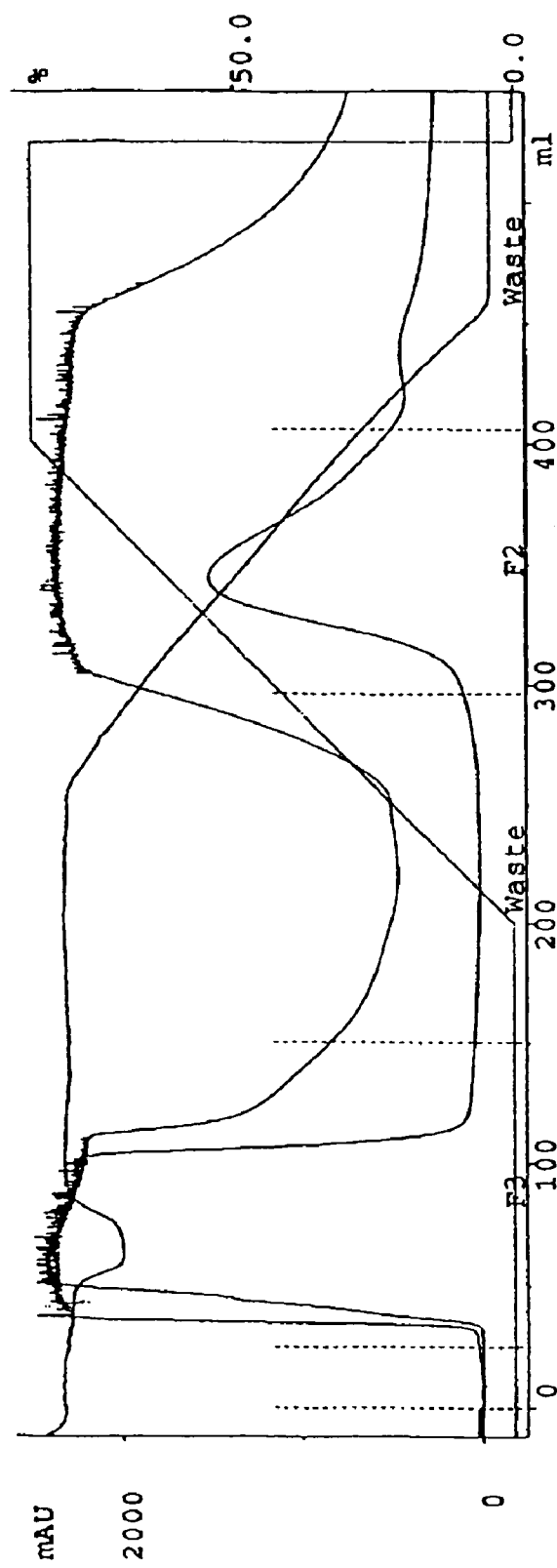
FIG. 34 illustrates the purification of the conjugate HSA: twelfth GLP-1 analogue (SEQ ID NO:26) by a preferred embodiment of the method of the present invention.

The twelfth GLP-1 analogue is GLP-1 (7-36) $Lys^{34}$ ($\epsilon$-AEEA-MPA)-$CONH_2$ and has the following sequence:
HAEGTFTSDVSSYLEGQAAKEFIAWLVK($\epsilon$-AEEA-MPA)GR-$CONH_2$ The purification of a conjugate made from reacting 2.5 ml 25% 250 mg/ml HSA (Cortex-Biochem, San Leandro, Calif.) with 1 mM twelfth GLP-1 analogue diluted into 22.5 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 34 the purified conjugate fraction appears in fraction F2.

EXAMPLE 35

"Purification of HSA: First Insulin Derivative Conjugate

The first insulin derivative is human insulin with MPA on position B1 of B chain (SEQ ID NO: 4) and native A chain (SEQ ID NO: 35); and his structure is detailed in Example 7."

Figure 35:
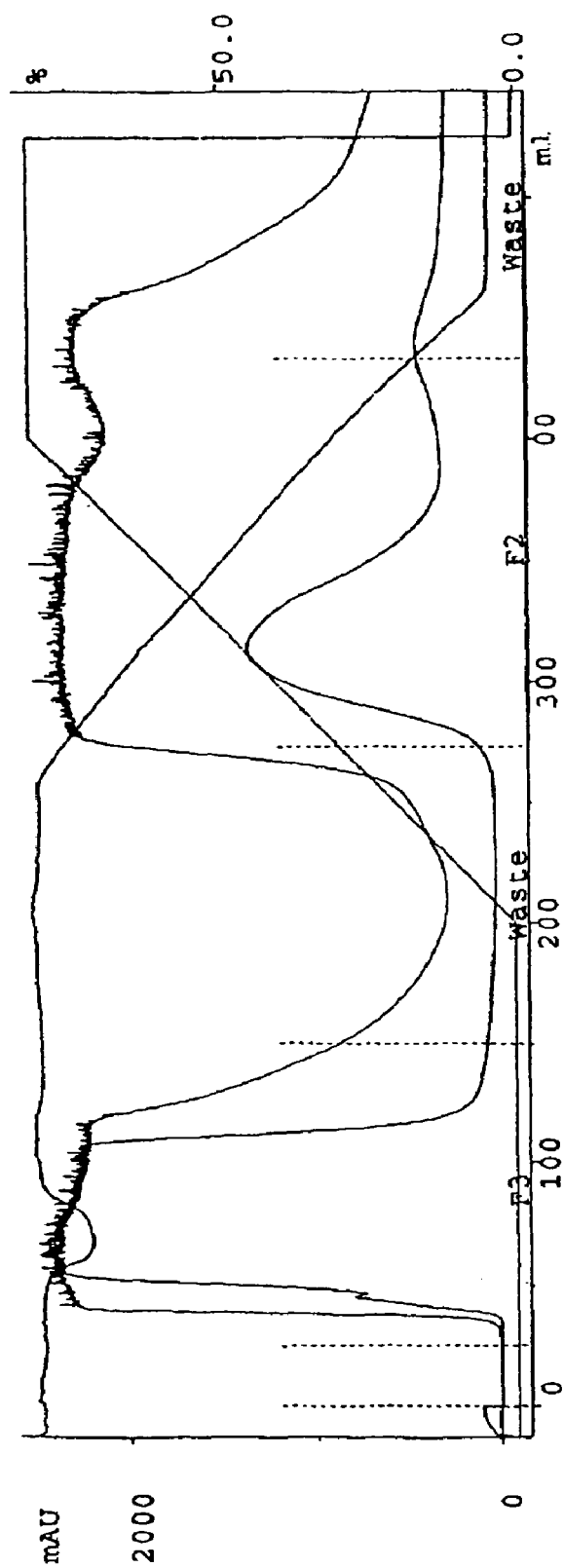
"FIG. 35 illustrates the purification of the conjugate HSA: first insulin derivative having modification on chain B (SEQ ID NO:4) by a preferred embodiment of the method of the present invention;"

The purification of a conjugate made from reacting 2.5 ml 25% 250 mg/ml HSA (Cortex-Biochem, San Leandro, Calif.) with 1 mM first insulin derivative diluted into 22.5 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 35 the purified conjugate fraction appears in fraction F2.

EXAMPLE 36

"Purification of HSA: Third Insulin Derivative Conjugate

The third insulin derivative is human insulin with OA-MPA on position B1 of B chain (SEQ ID NO: 27) and native A chain (SEQ ID NO: 35); and is represented in FIG. 1 shown above in Example 7."

Figure 36:
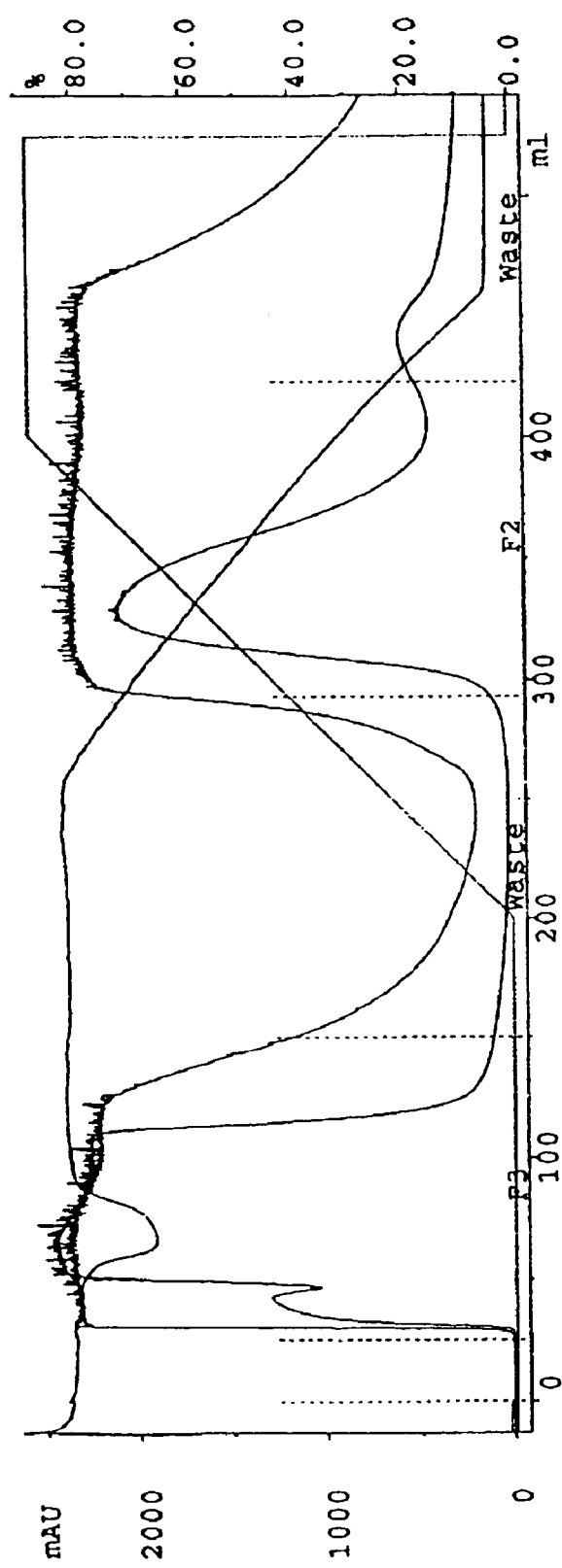
"FIG. 36 illustrates the purification of the conjugate HSA: third insulin derivative having modification on chain B (SEQ ID NO:27) by a preferred embodiment of the method of the present invention;"

The purification of a conjugate made from reacting 4 ml 25% 250 mg/ml HSA (Cortex-Biochem, San Leandro, Calif.) with 1 mM third insulin derivative diluted into 21 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 36 the purified conjugate fraction appears in fraction F2.

EXAMPLE 37

"Purification of HSA: Second Insulin Derivative Conjugate

The second insulin derivative is human insulin with MPA on position A1 of A chain (SEQ ID NO: 5) and native B chain (SEQ ID NO: 53); and is represented in FIG. 1 shown above in Example 7."

Figure 37:
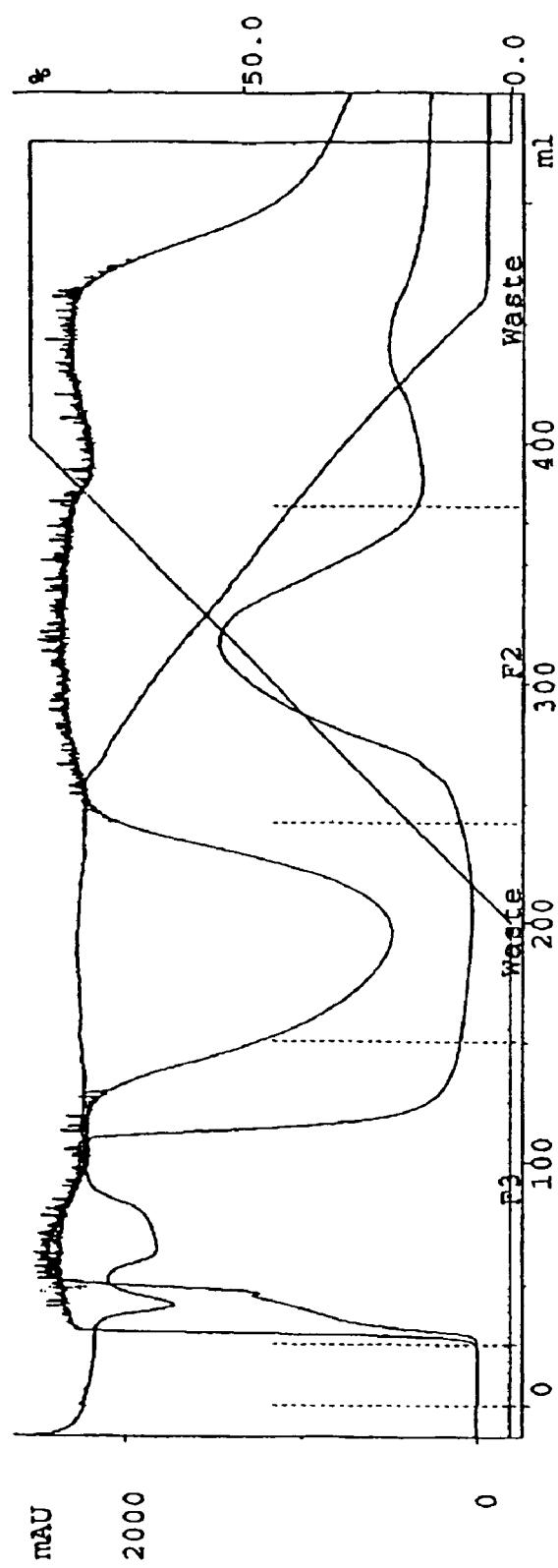
"FIG. 37 illustrates the purification of the conjugate HSA: second insulin derivative having modification on chain B (SEQ ID NO:5) by a preferred embodiment of the method of the present invention;"

The purification of a conjugate made from reacting 3 ml 25% 250 mg/ml HSA (Cortex-Biochem, San Leandro, Calif.) with 1 mM second insulin derivative diluted into 22 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 37 the purified conjugate fraction appears in fraction F2.

EXAMPLE 38

"Purification of HSA: Fourth Insulin Derivative Conjugate

The fourth insulin derivative is human insulin with MPA on position B29 of B chain (SEQ ID NO: 28) and native A chain (SEQ ID NO: 35); and is represented in FIG. 1 shown above in Example 7."

Figure 38:
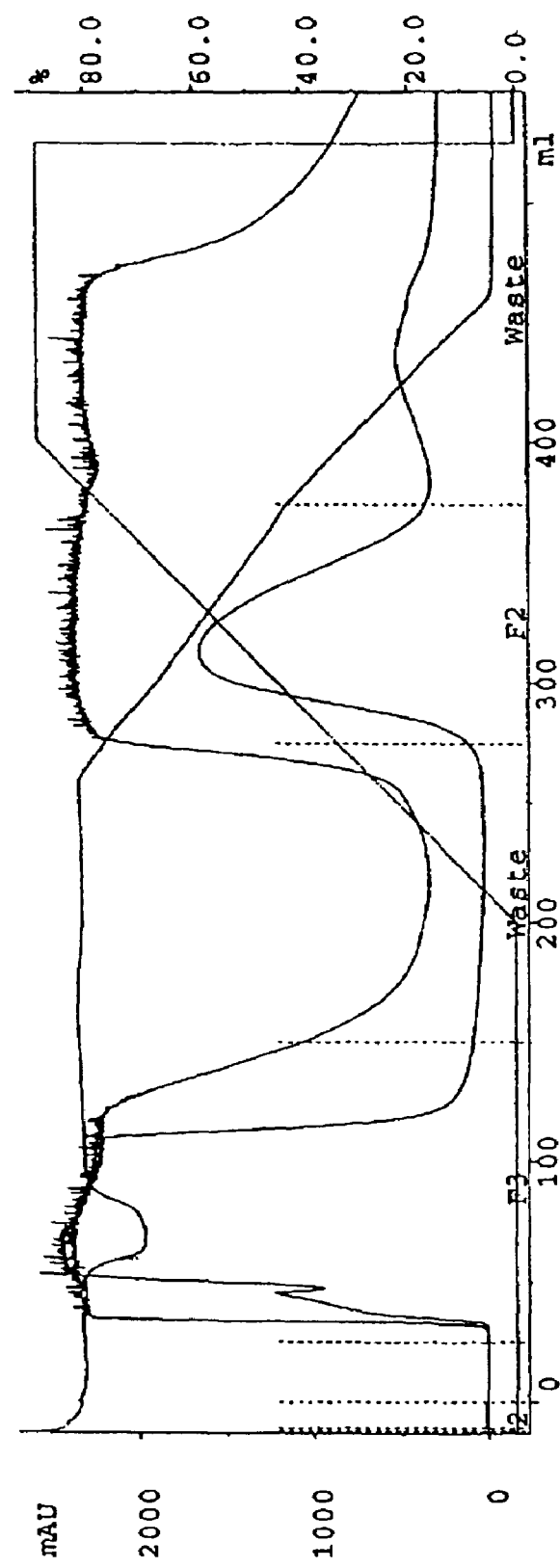
"FIG. 38 illustrates the purification of the conjugate HSA: fourth insulin derivative having modification on chain B (SEQ ID NO:28) by a preferred embodiment of the method of the present invention;"

The purification of a conjugate made from reacting 3 ml 25% 250 mg/ml HSA (Cortex-Biochem, San Leandro, Calif.) with 1 mM fourth insulin derivative diluted into 22 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 38 the purified conjugate fraction appears in fraction F2.

EXAMPLE 39

Purification of HSA: First GRF Analogue (SEQ ID NO:2) Conjugate

The first GRF analogue is GRF (1-29) dAla$^2$ Gln$^8$ Ala$^{15}$ Leu$^{27}$ Lys$^{30}$ ($\epsilon$-MPA) CONH$_2$ and his sequence is shown in Example 2.

Figure 39:
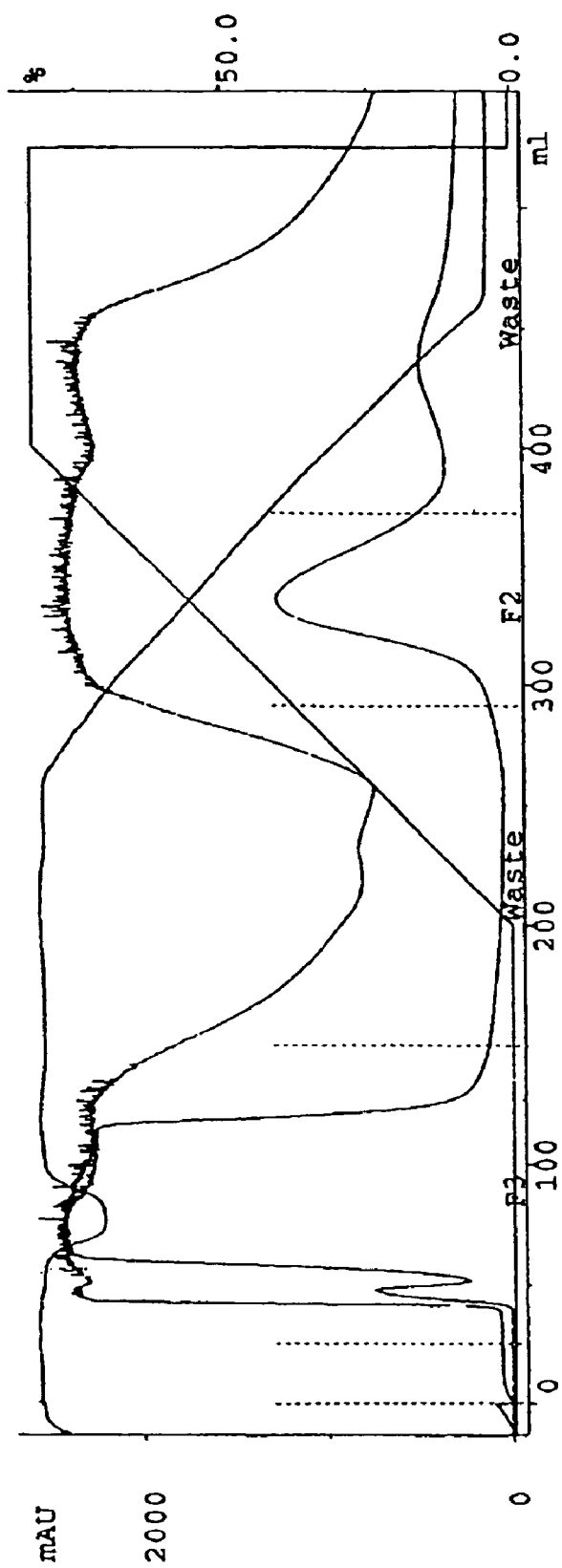
FIG. 39 illustrates the purification of the conjugate HSA: first GRF analogue (SEQ ID NO:2) by a preferred embodiment of the method of the present invention.

The purification of a conjugate made from reacting 3.7 ml 25% 250 mg/ml HSA (Cortex-Biochem, San Leandro, Calif.) with 1 mM first GRF analogue diluted into 22 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 39 the purified conjugate fraction appears in fraction F2.

EXAMPLE 40

Purification of HSA: Second GRF Analogue (SEQ ID NO:29) Conjugate

The second GRF analogue is GRF(1-29) Lys$^{30}$ ($\epsilon$-MPA)-CONH$_2$ and has the following sequence:

YADAIFTNSYRKVLGQLSARKLLQDIMSRK(MPA)-CONH$_{21}$

Figure 40:
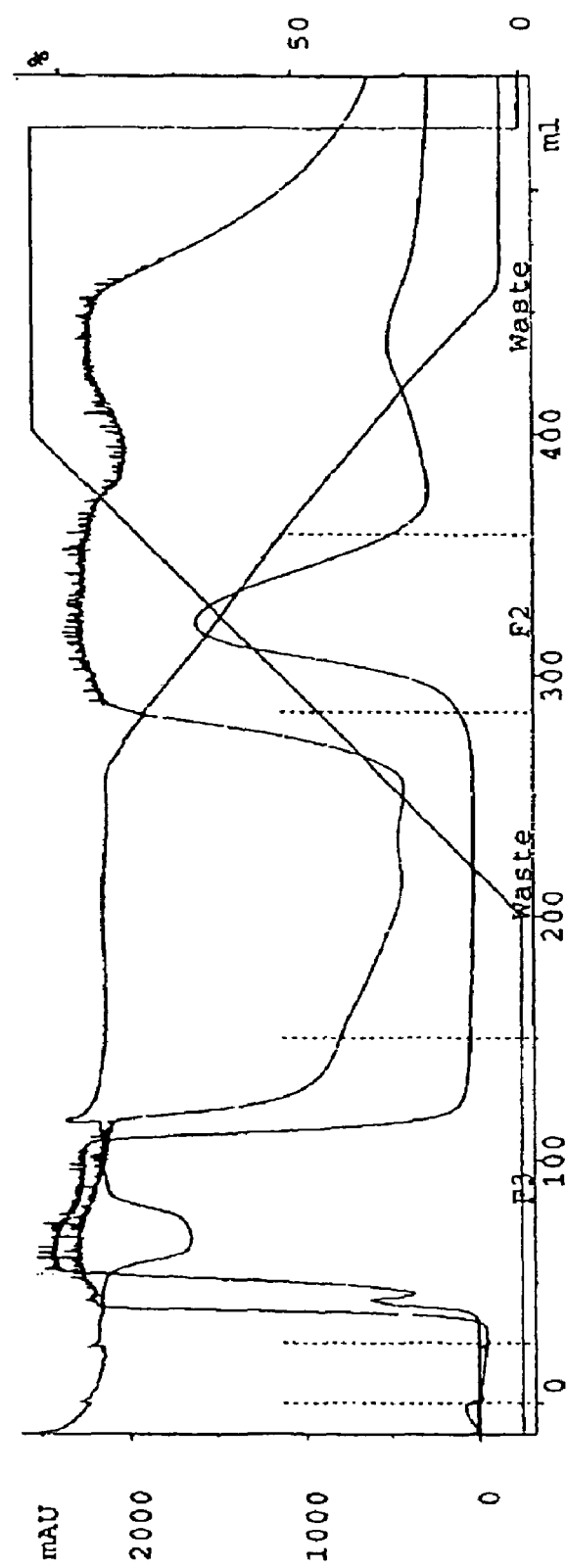
FIG. 40 illustrates the purification of the conjugate HSA: second GRF analogue (SEQ ID NO:29) by a preferred embodiment of the method of the present invention.

The purification of a conjugate made from reacting 2.5 ml 25% 250 mg/ml HSA (Cortex-Biochem, San Leandro, Calif.) with 1 mM second GRF analogue diluted into 22.5 ml of 20 mM sodium phosphate buffer (pH 7.0), 5 mM sodium caprylate and 900 mM $(NH_4)_2SO_4$ was performed on a column of Butyl sepharose using gradient #3 described above. In FIG. 40 the purified conjugate fraction appears in fraction F2.

EXAMPLE 41

Purification of HSA: Third GRF Analogue (SEQ ID NO:30) Conjugate

The third GRF analogue is GRF (1-29) dAla$^2$ Gln$^8$ dArg$^{11}$ Ala$^{15}$ Leu$^{27}$ Lys$^{30}$ ($\epsilon$-MPA)-CONH$_2$ and has the following sequence:

YaDAIFTNSYRKVLAQLSARKLLQDILSRK(MPA)-CONH$_2$

Figure 41:
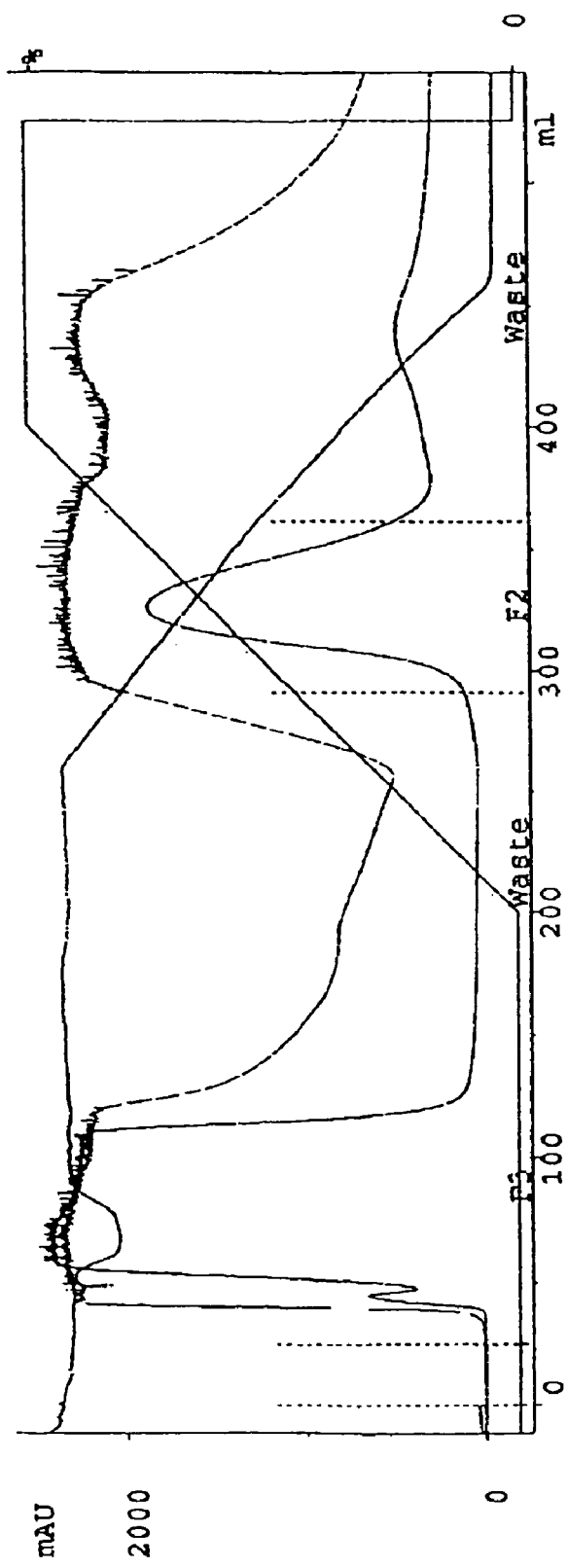
FIG. 41 illustrates the purification of the conjugate HSA: third GRF analogue (SEQ ID NO:30) by a preferred embodiment of the method of the present invention.

The purification of a conjugate made from reacting 2.5 ml 25% 250 mg/ml HSA (Cortex-Biochem, San Leandro, Calif.) with 1 mM third GRF analogue diluted into 22.5 ml of 20 mM sodium phosphate buffer (pH 7.0), 5 mM sodium caprylate and 750 mM $(NH_4)_2SO_4$ was performed on a column of Butyl sepharose using gradient #3 described above. In FIG. 41 the purified conjugate fraction appears in fraction F2.

EXAMPLE 42

Purification of HSA: Fourth GRF Analogue (SEQ ID NO:31) Conjugate

The fourth GRF analogue is GRF (1-29) dAla$^2$ Lys$^{30}$ ($\epsilon$-MPA)-CONH$_2$ and has the following sequence:

YaDAIFTNSYRKVLGQLSARKLLQDIMSRK(MPA)-CONH$_2$

Figure 42:
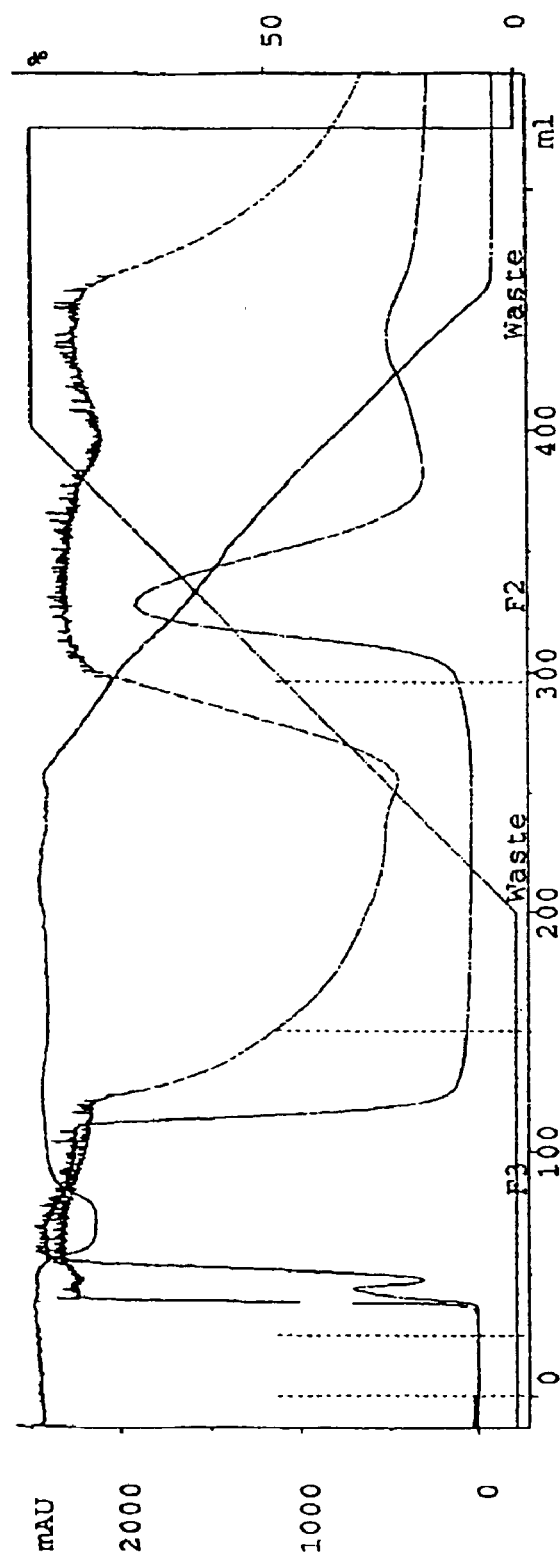
FIG. 42 illustrates the purification of the conjugate HSA: fourth GRF analogue (SEQ ID NO:31) by a preferred embodiment of the method of the present invention.

The purification of a conjugate made from reacting 2.5 ml 25% HSA (Cortex-Biochem, San Leandro, Calif.) with 1 mM fourth GRF analogue diluted in 22.5 ml of 20 mM sodium phosphate buffer (pH 7.0), 5 mM sodium caprylate and 900 mM $(NH_4)_2SO_4$ was performed on a column of Butyl sepharose using gradient #3 described above. In FIG. 42 the purified conjugate fraction appears in fraction F2.

EXAMPLE 43

Purification of HSA: Thirteenth GLP-1 Analogue CJC 1365 (SEQ ID NO:32) Conjugate The thirteenth GLP-1 analogue is GLP-1 (9-36) $Lys^{37}$ (ε-AEEA-MPA)-$CONH_2$ and has the following sequence:

EGTFTSDVSSYLEGQAAKEFIAWLVKGRK(ε-AEEA-MPA)-$CONH_2$

Figure 43:
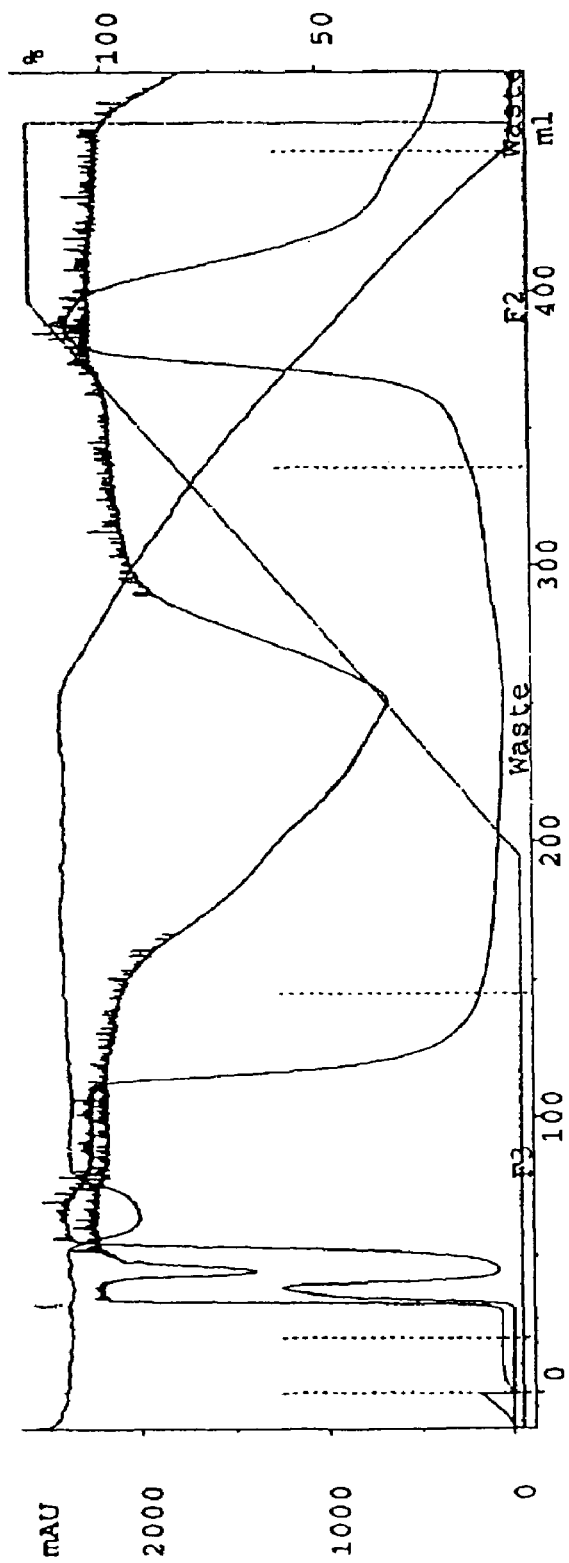
FIG. 43 illustrates the purification of the conjugate HSA: thirteenth GLP-1 analogue CJC 1365 (SEQ ID NO:32) by a preferred embodiment of the method of the present invention.

The purification of a conjugate made from reacting 3.5 ml 25% HSA (Cortex-Biochem, San Leandro, Calif.) and 1 mM thirteenth GLP-1 analogue diluted in 21.5 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 43 the purified conjugate fraction appears in fraction F2.

EXAMPLE 44

Purification of HSA Lactose:First GLP-1 Analogue (SEQ ID NO:1) Conjugate

The first GLP-1 analogue is GLP-1 (7-36) $dAla^8$ $Lys^{37}$ (ε-AEEA-MPA)-$CONH_2$ and his sequence is shown above in Example 1.

Figure 44:
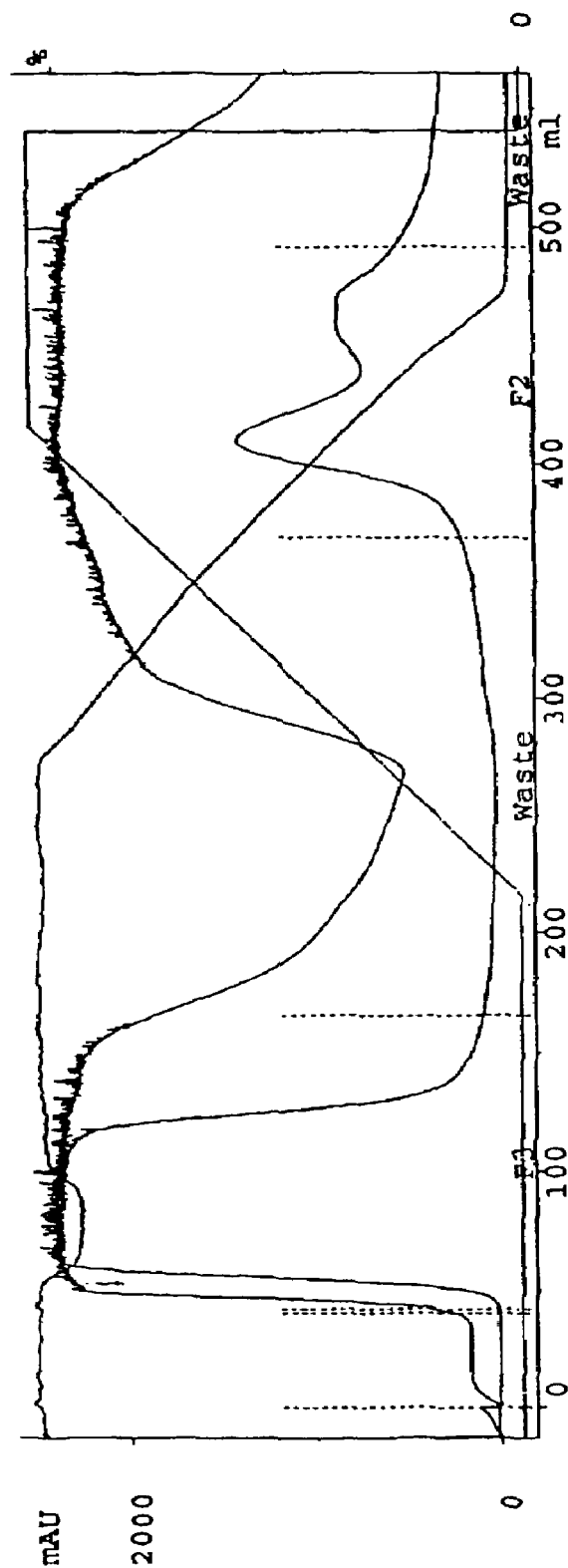
FIG. 44 illustrates the purification of the conjugate HSA lactose: first GLP-1 analogue (SEQ ID NO:1) by a preferred embodiment of the method of the present invention.

The purification of a conjugate made from reacting 4 ml 25% lactosaminated albumin (HSA pre-incubated with excess lactose at 37° C., pH 7.0) with 200 μM first GLP-1 analogue in 4 ml of a buffer made of 20 mM sodium phosphate, 5 mM sodium caprylate and 750 mM $(NH_4)_2SO_4$, (pH 7.0) was performed on a column of Butyl sepharose using gradient #1 described above. In FIG. 44 the purified lactosaminated conjugate fraction appears in fraction F2.

EXAMPLE 45

Purification of HSA: First T20 Analogue (SEQ ID NO:33) Conjugate

The first T20 analogue is Ac-T20 (1-36) $Lys^{37}$ (ε-AEEA-MPA)-$CONH_2$ and ahs the following sequence:

Ac-YTSLIHSLIEESQNQQEKNEQELLELDK-WASLWNWFK(AEEA-MPA)-$CONH_2$

Figure 45:
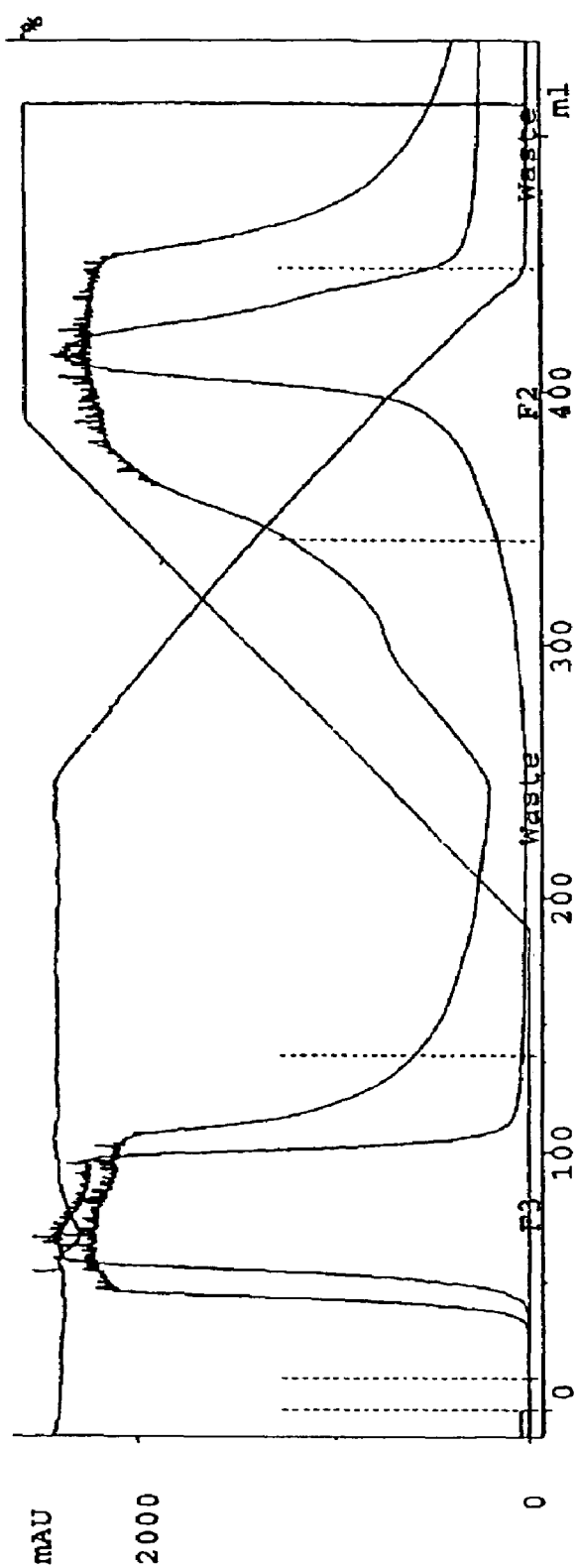
FIG. 45 illustrates the purification of the conjugate HSA: first T20 analogue (SEQ ID NO:33) by a preferred embodiment of the method of the present invention.

The purification of a conjugate made from reacting 2.5 ml 25% HSA with 1 mM first T20 analogue in 10 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 45 the purified conjugate fraction appears in fraction F2.

EXAMPLE 46

Purification of HSA: First T1249 Analogue (SEQ ID NO:34) Conjugate

The first T1249 analogue is Ac-T1249 (1-39) $Lys^{40}$ (ε-AEEA-MPA)-$CONH_2$ and has the following sequence:

AC-WQEWEQKITALLEQA-QIQQEKNEYELQKLDKWASLWEWFK(AEEA-MPA)-$CONH_2$

Figure 46:
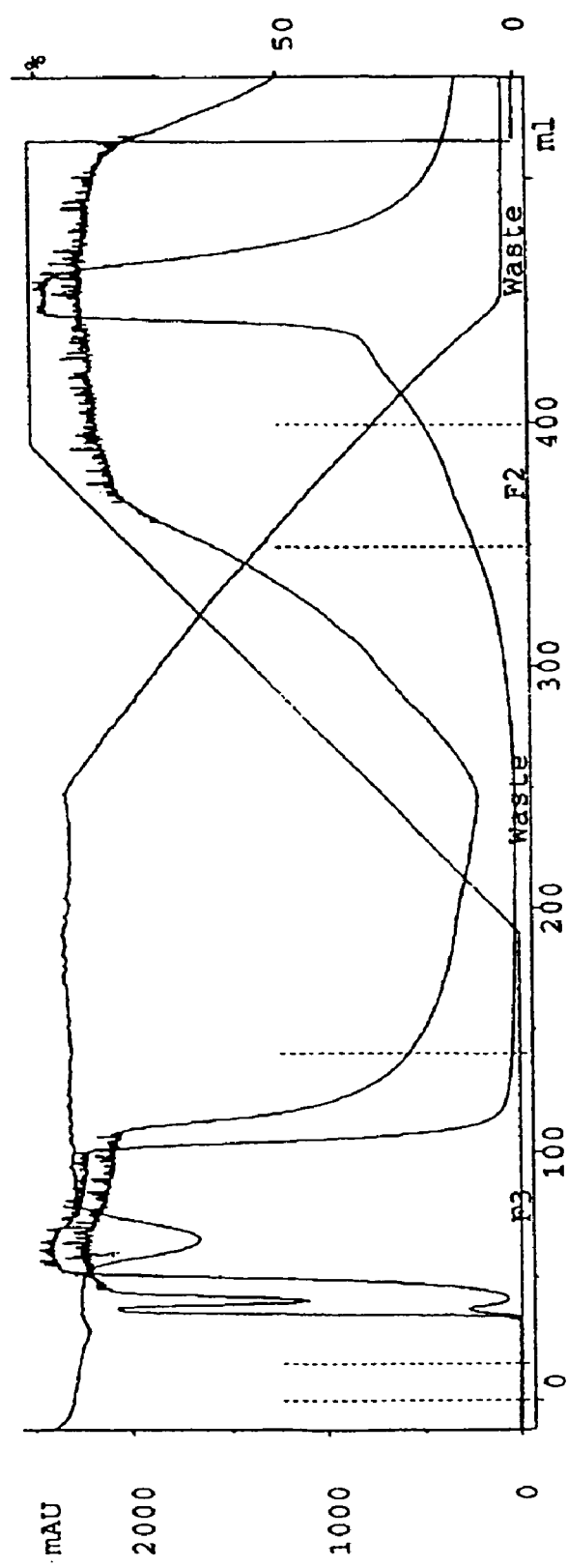
FIG. 46 illustrates the purification of the conjugate HSA: first T1249 analogue (SEQ ID NO:34) by a preferred embodiment of the method of the present invention.

The purification of a conjugate made from reacting 2 ml 25% HSA and 1 mM first T1249 analogue in 10.5 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 46 the purified conjugate fraction appears in fraction F4.

EXAMPLE 47

Purification of a HSA: First GLP-1 Analogue (SEQ ID NO:1)

The first GLP-1 analogue is GLP-1 (7-36) $dAla^8$ $Lys^{37}$ (ε-AEEA-MPA)-$CONH_2$ and his sequence is shown in Example 1.

Figure 47:
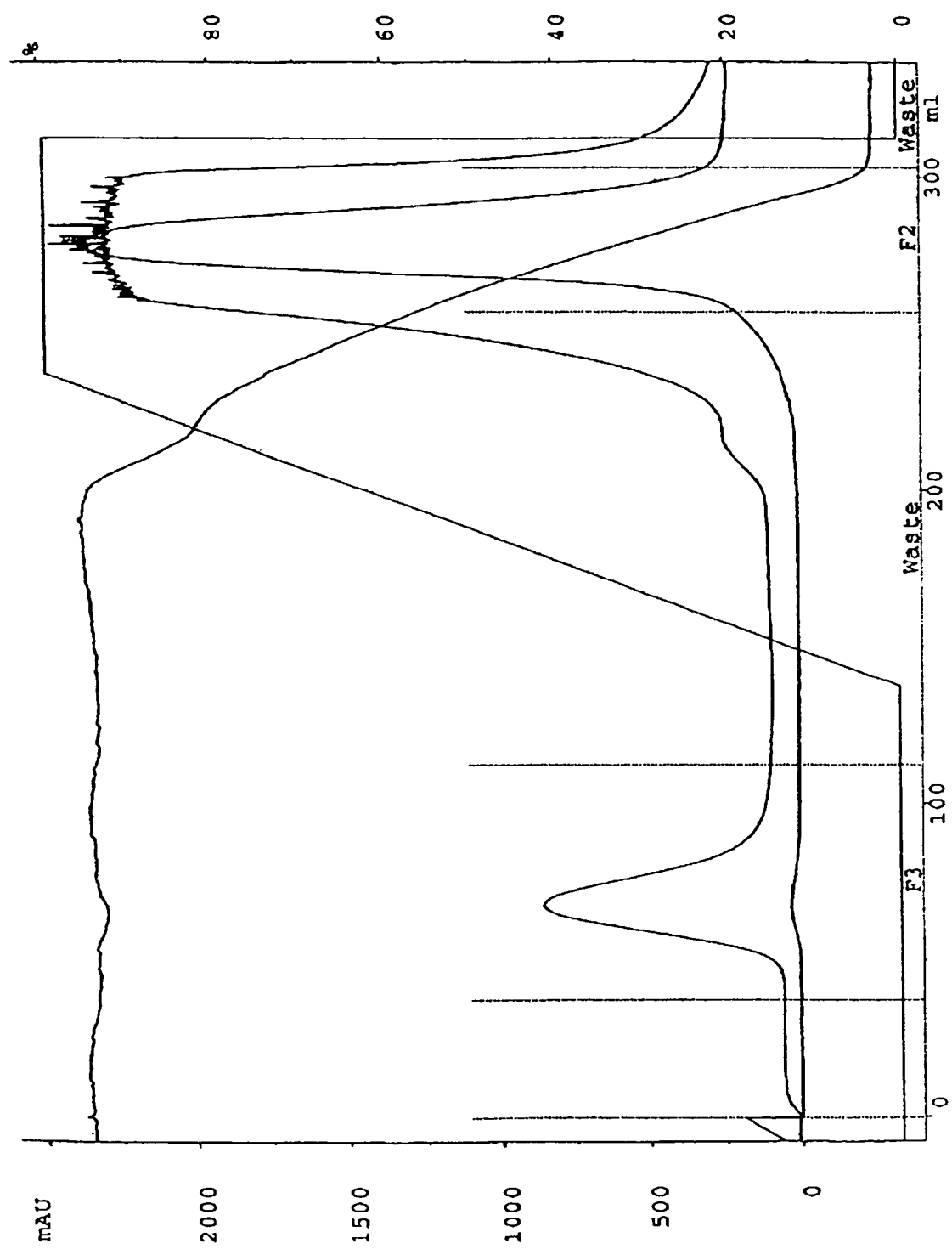
FIG. 47 illustrates the purification of the compound HSA: first GLP-1 analogue (SEQ ID NO:1) by a preferred embodiment of the method of the present invention.

The purification of 114.45 mg of the preformed conjugate of the first GLP-1 analogue in 12.5 ml of 20 mM sodium phosphate buffer (pH 7.0), 5 mM sodium caprylate and 750 mM $(NH_4)_2SO_4$ was performed on a column of Butyl sepharose using gradient #5 described above. FIG. 47 illustrates the separation curve obtained with the conjugate found in fraction F2.

EXAMPLE 48

Purification of a HSA: First C34 Analogue (SEQ ID NO:6)

The first C34 analogue is MPA-AEEA-C34-$CONH_2$ and his sequence is shown above in Example 9.

Figure 48:
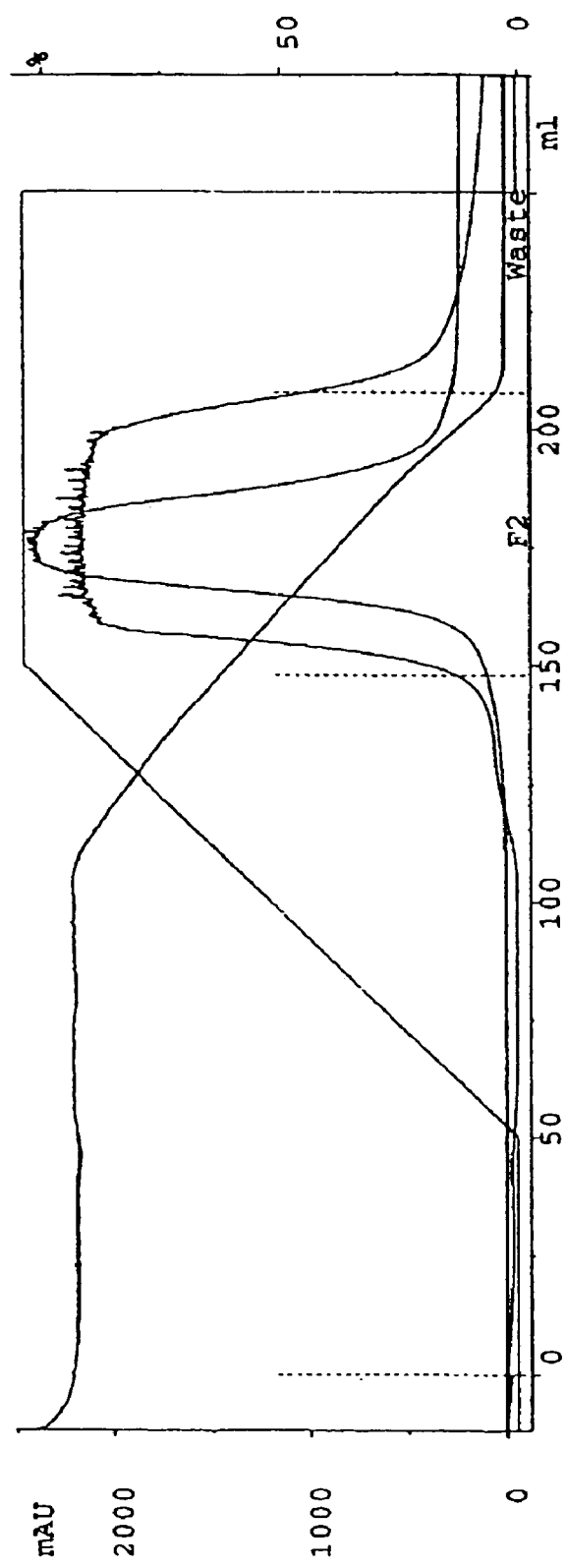
FIG. 48 illustrates the purification of the compound HSA: first C34 analogue (SEQ ID NO:6) by a preferred embodiment of the method of the present invention.

The purification of 114.45 mg of the preformed conjugate of the first C34 analogue in 12.5 ml of 20 mM sodium phosphate buffer (pH 7.0), 5 mM sodium caprylate and 750 mM $(NH_4)_2SO_4$ was performed on a column of Butyl sepharose using gradient #5 described above. FIG. 48 illustrates the separation curve obtained with the conjugate found in fraction F2.

EXAMPLE 49

Purification of a HSA: Second GRF Analogue (SEQ ID NO:29)

The second GRF analogue is GRF(1-29) $Lys^{30}$ (ε-MPA)-$CONH_2$ and his sequence is shown above in Example 40.

Figure 49:
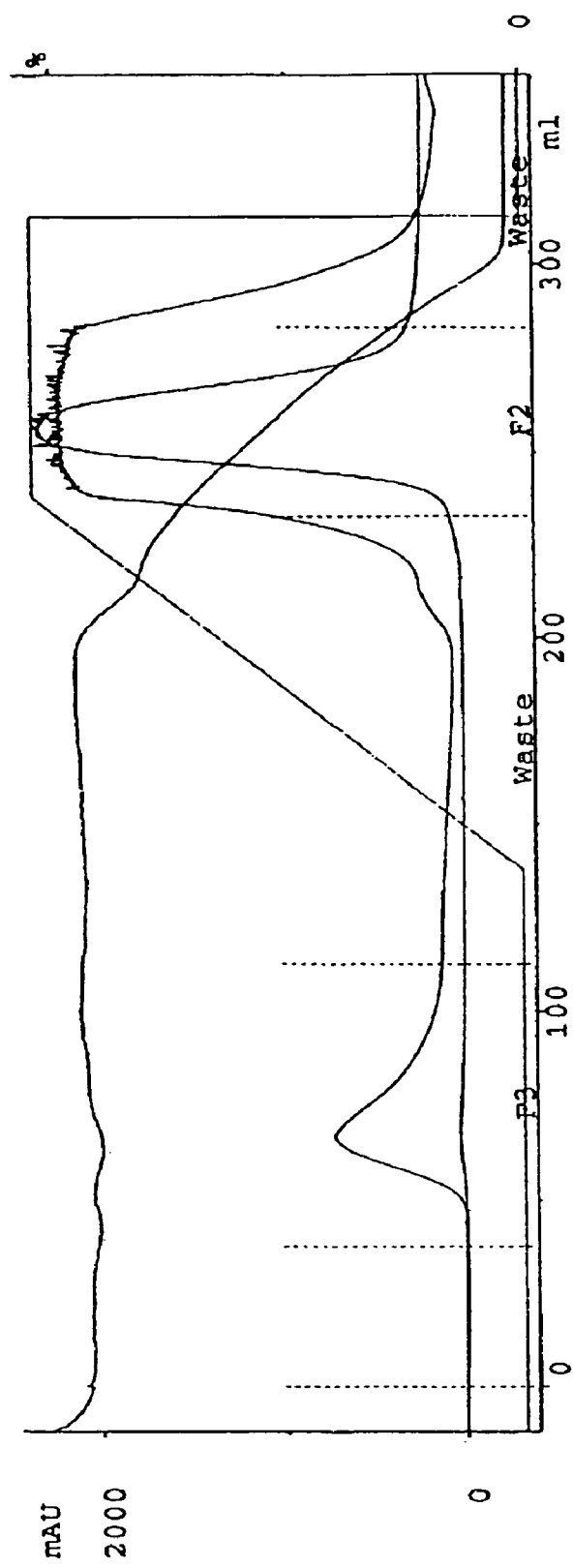
FIG. 49 illustrates the purification of the compound HSA: second GRF analogue (SEQ ID NO:29) by a preferred embodiment of the method of the present invention.

The purification of 125.53 mg of the preformed conjugate of the second GRF analogue in 12.5 ml of 20 mM sodium phosphate buffer (pH 7.0), 5 mM sodium caprylate and 750 mM $(NH_4)_2SO_4$, pH 7.0 was performed on a column of Butyl sepharose using gradient #5 described above. FIG. 49 illustrates the separation curve obtained with the conjugate found in fraction F2.

EXAMPLE 50

"Purification of HSA: Vinorelbine Analogue Conjugate

The vinorelbine analogue is a molecule of vinorelbine with AEEA-MPA coupled thereto as illustrated in the following structure:"

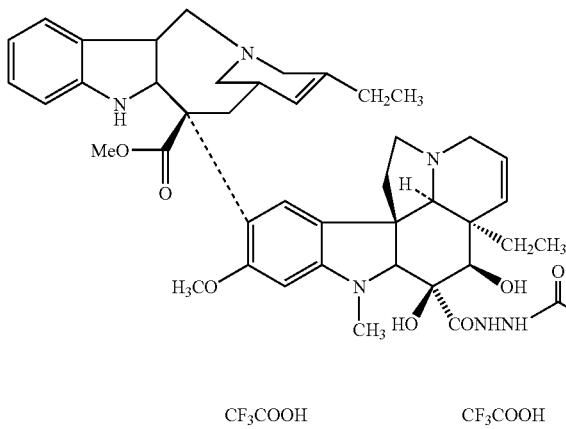
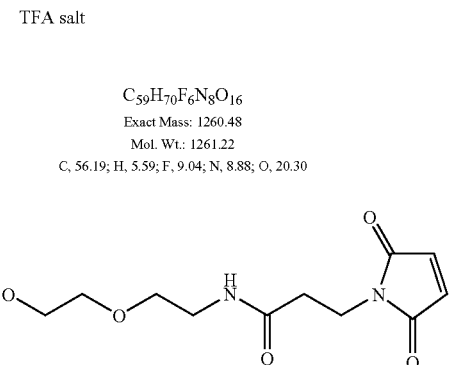

Figure 50:
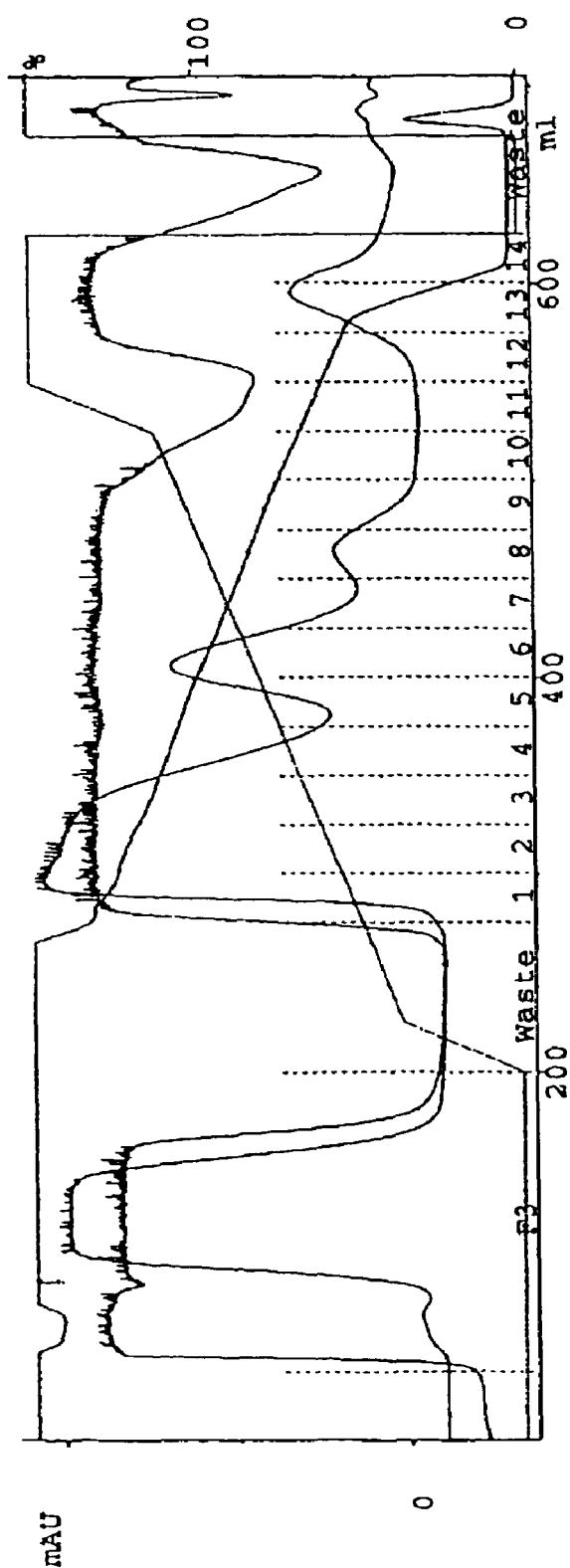
"FIG. 50 illustrates the purification of the conjugate HSA: vinorelbine analogue conjugate by a preferred embodiment of the method of the present invention;"

The purification of a conjugate made from 2.5 ml 25% HSA and 1 mM vinorelbine analogue in 22.5 ml of a buffer made of 20 mM sodium phosphate buffer, 5 mM sodium caprylate and 750 mM $(NH_4)_2SO_4$, pH 7.0 was performed on a column of Butyl sepharose using gradient #4 described above. In FIG. 50 the purified conjugate fraction appears in fraction F2. The conjugate fraction was concentrated with Amicon™ filter 30 kDa.

EXAMPLE 51

Purification of L-Cysteine

Figure 51:
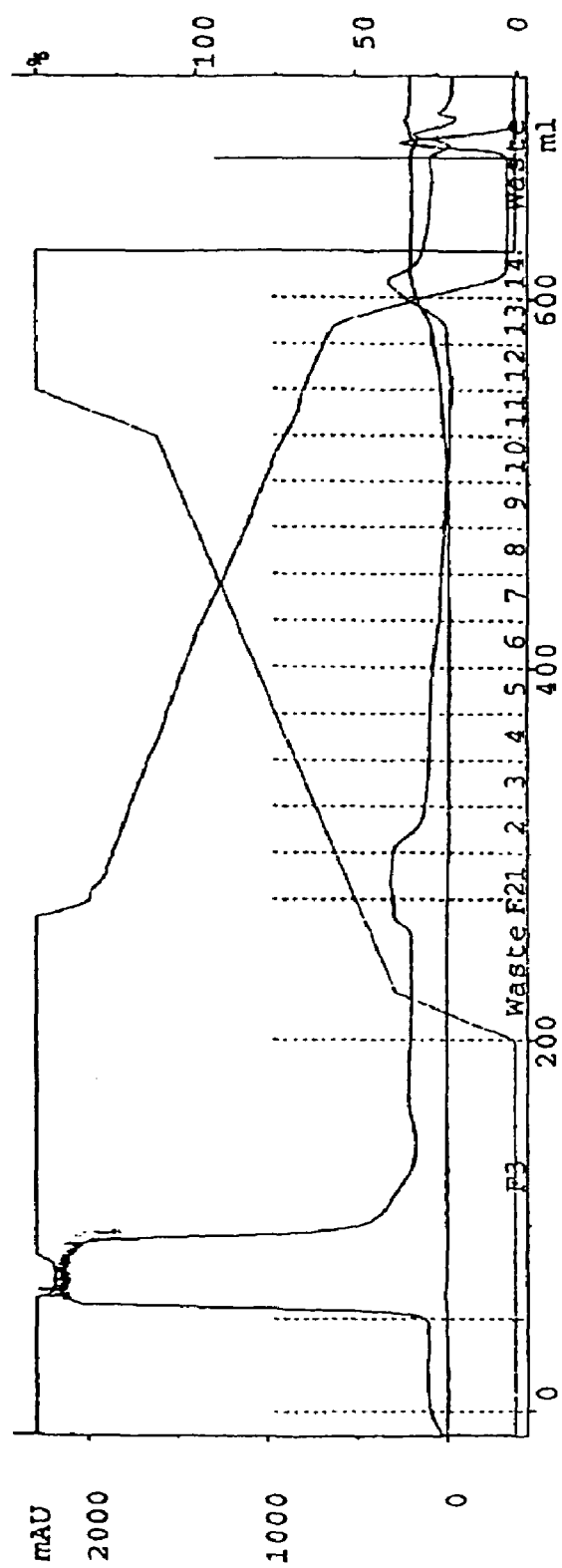
FIG. 51 illustrates the purification of L-cysteine by a preferred embodiment of the method of the present invention.

The purification of 2.5 ml 40 mM L-cysteine in 22.5 ml of 20 mM sodium phosphate buffer (pH 7.0), 5 mM sodium caprylate and 1500 mM $(NH_4)_2SO_4$, was performed on a column of Butyl sepharose using gradient #4 described above. FIG. 51 illustrates the separation curve obtained with L-cysteine eluting within the void volume of the column (fraction F3).

EXAMPLE 52

"Purification of L-Cysteine:Vinorelbine Analogue Conjugate

The vinorelbine analogue is a molecule of vinorelbine with AEEA-MPA coupled thereto as illustrated in the structure shown in Example 50."

Figure 52:
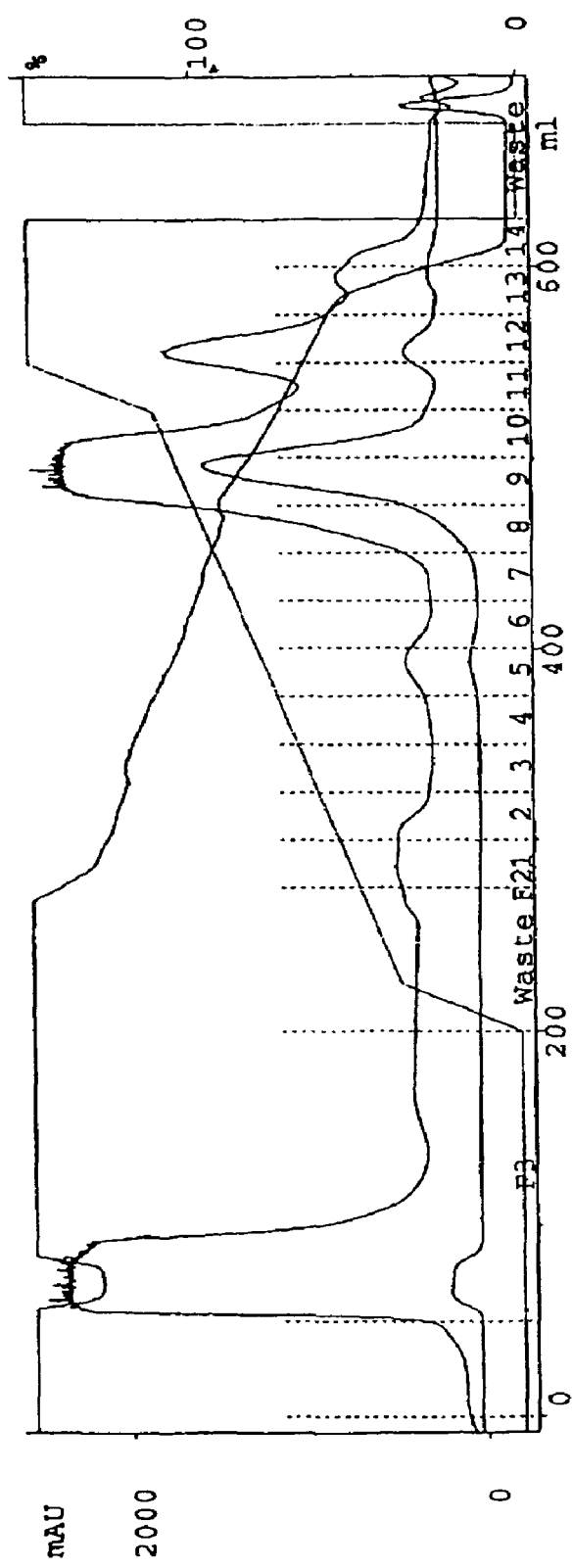
"FIG. 52 illustrates the purification of the conjugate L-Cysteine: vinorelbine analogue by a preferred embodiment of the method of the present invention;"

The purification of a conjugate made from reacting 2.5 ml 40 mM L-cysteine with 1 mM vinorelbine analogue in 22.5 ml of 20 mM sodium phosphate buffer (pH 7.0), 5 mM sodium caprylate and 750 mM $(NH_4)_2SO_4$ was performed on a column of Butyl sepharose using gradient #4 described above. FIG. 52 illustrates the separation curve obtained with the L-cysteine conjugate eluting within fractions F8, F9 and F10.

EXAMPLE 53

Purification of RSA: Third Exendin-4 Analogue (SEQ ID NO:25) Conjugate

The third Exendin-4 analogue is Exendin-4-(1-39) $Lys^{40}$ ($\epsilon$-AEEA-MPA)-$CONH_2$ and his sequence shown in Example 33.

Figure 53:
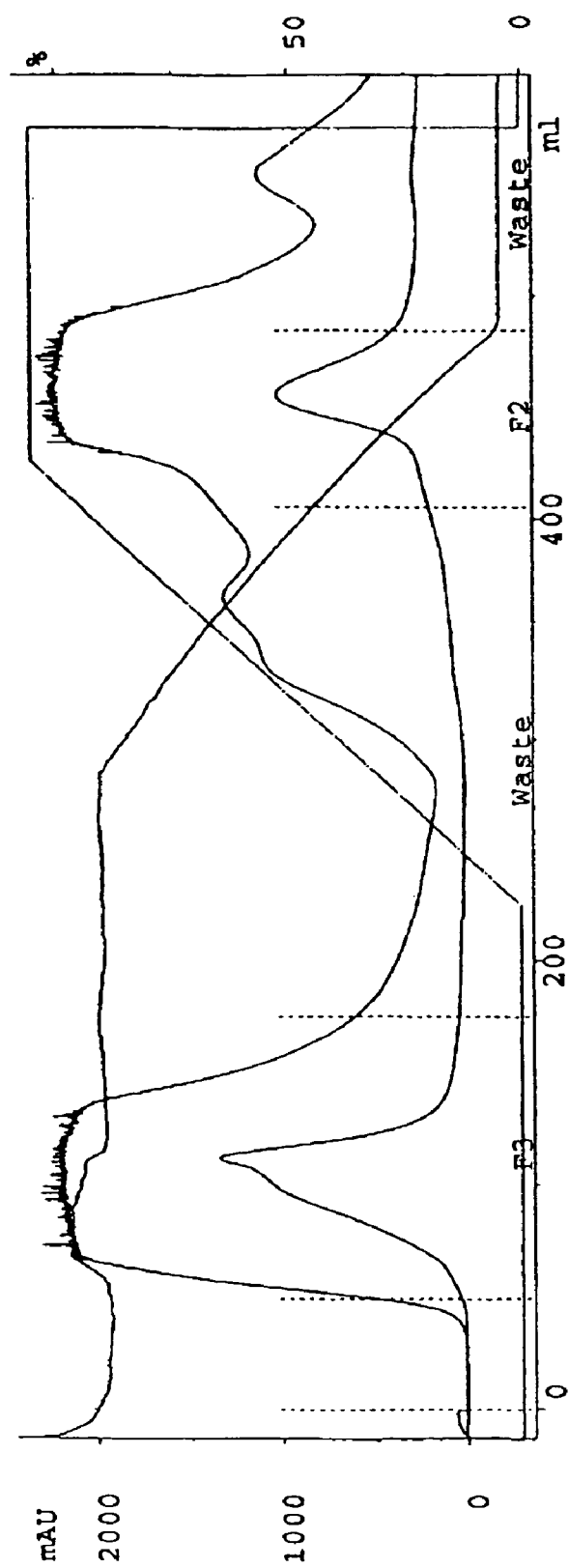
FIG. 53 illustrates the purification of the conjugate RSA: third Exendin-4 analogue (SEQ ID NO:25) by a preferred embodiment of the method of the present invention.

The purification of a conjugate made from reacting 11 ml 5% RSA (rat serum albumin) with 200 μM third Exendin-4 analogue in 11 ml of 20 mM sodium phosphate buffer (pH 7.0), 5 mM sodium caprylate and 750 mM $(NH_4)_2SO_4$, was performed on a column of Butyl sepharose using gradient #1 described above. In FIG. 53 the purified conjugate fraction appears in fraction F2.

EXAMPLE 54

Purification of HSA: Fourth C34 Analogue (SEQ ID NO:36) Conjugate

Figure 54:
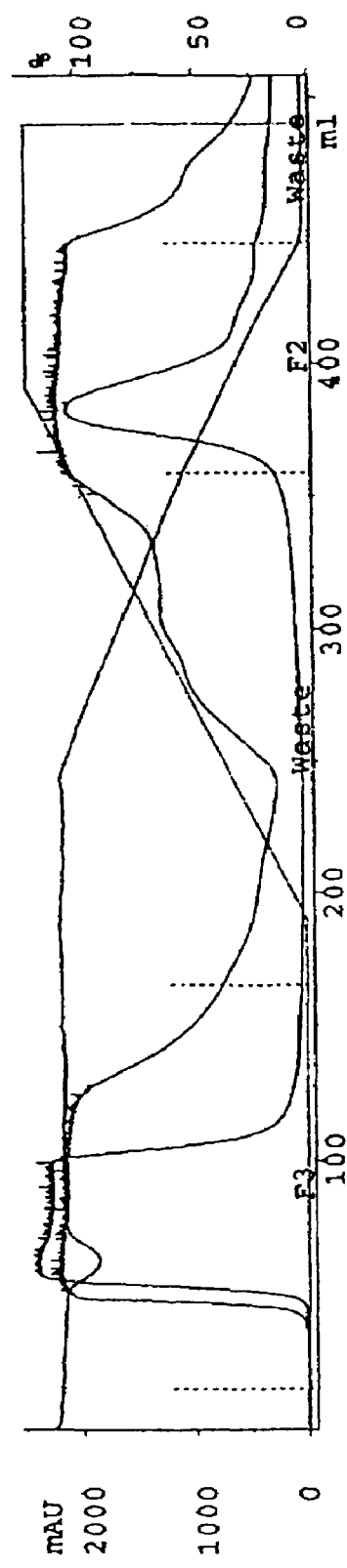
FIG. 54 illustrates the purification of the conjugate HSA: fourth C34 analogue (SEQ ID NO:36) by a preferred embodiment of the method of the present invention.

The fourth C34 analogue is C34 (1-34) $Lys^{13}$ ($\epsilon$-MPA)-$CONH_2$ and has the following sequence:
WMEWDREINNYTK(MPA)LIHSLIEESQN-
QQEKNEQELL-$CONH_2$ The purification of a conjugate made from reacting 2 ml 25% HSA with 1 mM fourth C34 analogue in 13 ml of 20 mM sodium phosphate buffer (pH 7.0), 5 mM sodium caprylate and 750 mM $(NH_4)_2SO_4$ was performed on a column of Butyl sepharose using gradient #1 described above. In FIG. 54 the purified conjugate fraction appears in fraction F2.

EXAMPLE 55

Purification of HSA: Fifth C34 Analogue (SEQ ID NO:37) Conjugate

Figure 55:
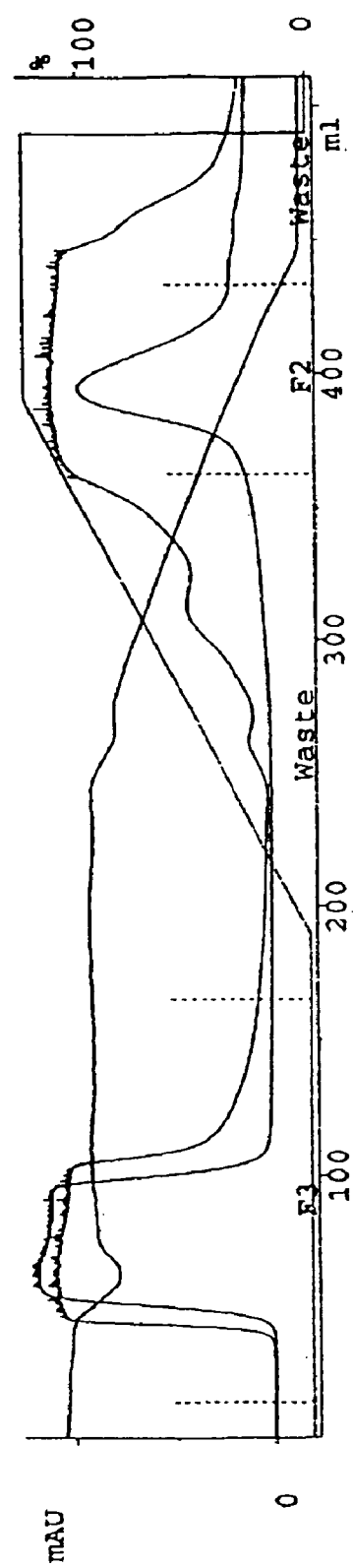
FIG. 55 illustrates the purification of the conjugate HSA: fifth C34 analogue (SEQ ID NO:37) by a preferred embodiment of the method of the present invention.

The fifth C34 analogue is C34 (1-34) $Lys^{35}$ ($\epsilon$-MPA)-$CONH_2$ and has the following sequence:
WMEWDREINNYTSLIHSLIEESQNQQEKNEQELLK
(MPA)-$CONH_2$ The purification of a conjugate made from 2 ml 25% HSA and 1 mM fifth C34 analogue in 13 ml of a buffer made of 20 mM sodium phosphate buffer (pH 7.0), 5 mM sodium caprylate and 750 mM $(NH_4)_2SO_4$, was performed on a column of Butyl sepharose using gradient #1 described above. In FIG. 55 the purified conjugate fraction appears in fraction F2.

EXAMPLE 56

Purification of HSA: Sixth C34 Analogue (SEQ ID NO:38) Conjugate

Figure 56:
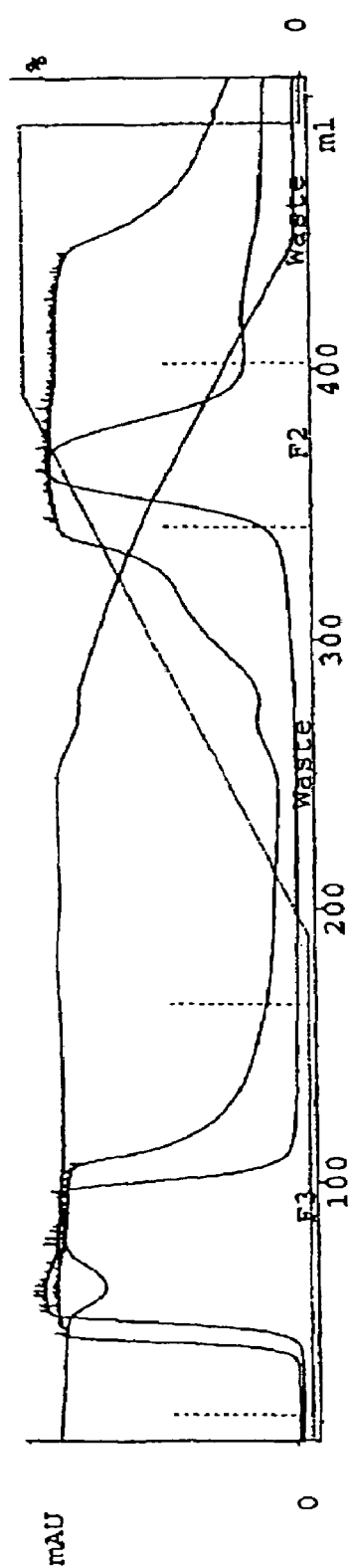
FIG. 56 illustrates the purification of the conjugate HSA: sixth C34 analogue (SEQ ID NO:38) by a preferred embodiment of the method of the present invention.

The sixth C34 analogue MPA-C34 (1-34)—CONH$_2$ and has the following sequence:
MPA-WMEWDREINNYTSLIHSLIEESQN-QQEKNEQELL-CONH$_2$ The purification of a conjugate made from reacting 2 ml 25% HSA and 1 mM sixth C34 analogue in 13 ml of 20 mM sodium phosphate buffer (pH 7.0), 5 mM sodium caprylate and 750 mM (NH$_4$)$_2$SO$_4$ was performed on a column of Butyl sepharose using gradient #1 described above. In FIG. 56 the purified conjugate fraction appears in fraction F2.

EXAMPLE 57

Purification of HSA: Seventh C34 Analogue (SEQ ID NO:39) Conjugate

Figure 57:
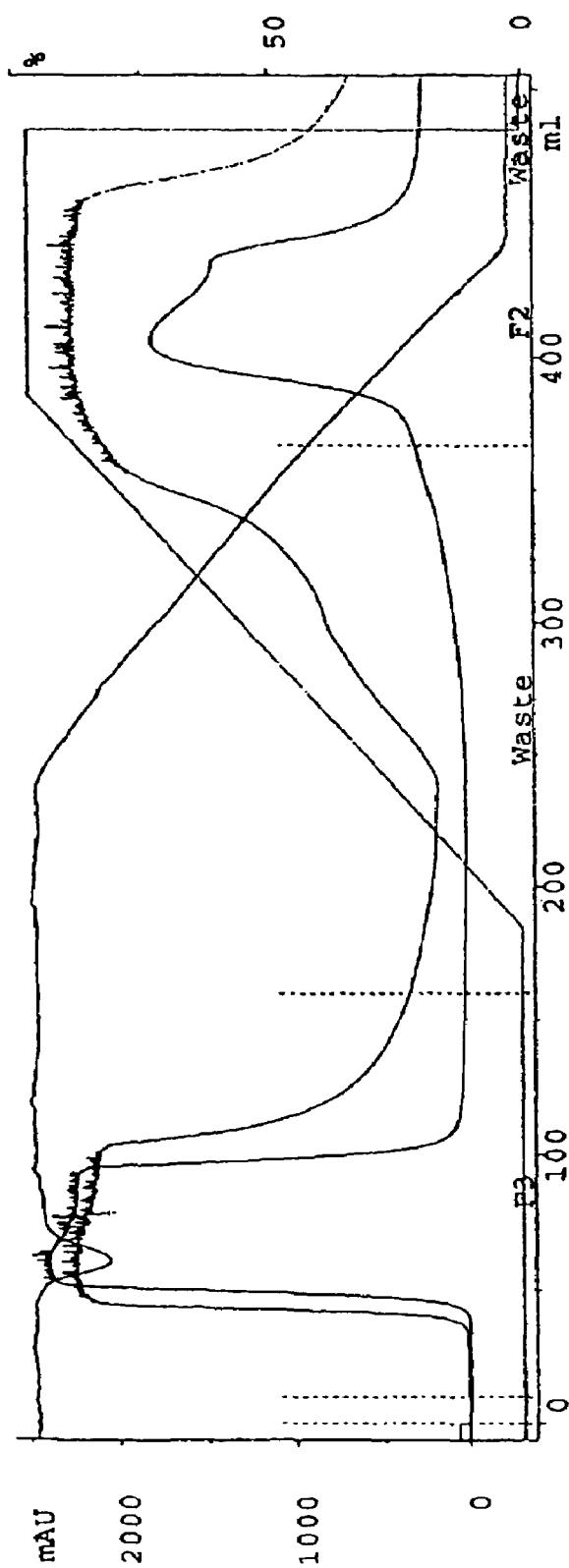
FIG. 57 illustrates the purification of the conjugate HSA: seventh C34 analogue (SEQ ID NO:39) by a preferred embodiment of the method of the present invention.

The seventh C34 analogue is Ac-C34 (1-34) Glu$^2$ Lys$^6$ Lys$^7$ Glu$^9$ Glu$^{10}$ Lys$^{13}$ Lys$^{14}$ Glu$^{16}$ Glu$^{17}$ Lys$^{20}$ Lys$^{21}$ Glu$^{23}$ Glu$^{24}$ Lys$^{27}$ Glu$^{31}$ Lys$^{34}$ Lys$^{35}$ Lys$^{36}$ ($\epsilon$-AEEA-MPA)-CONH$_2$ and has the following sequence:
Ac-WEEWDKKIEEYTKKIEELIKKSE-EQQKKNEEELKKK(AEEA-MPA)-CONH$_2$ The purification of a conjugate made from reacting 2 ml 25% HSA with 1 mM seventh C34 analogue in 13 ml 20 mM sodium phosphate buffer (pH 7.0), 5 mM sodium caprylate and 750 mM (NH$_4$)$_2$SO$_4$, was performed on a column of Butyl sepharose using gradient #1 described above. In FIG. 57 the purified conjugate fraction appears in fraction F2.

EXAMPLE 58

Purification of HSA: Eighth C34 Analogue (SEQ ID NO:40) Conjugate

The eighth C34 analogue is MPA-AEEA-C34 (1-34) Glu$^2$ Lys$^6$ Lys$^7$ Glu$^9$ Glu$^{10}$ Lys 13 Lys$^{14}$ Glu$^{16}$ Lys$^{17}$ Lys$^{20}$ Glu$^{23}$ Glu$^{24}$ Lys$^{27}$ Glu$^{31}$ Lys$^{34}$ Lys$^{35-}$CONH$_2$ and has the following sequence:

MPA-AEEA-WEEWDKKIEEYTKKIEELIKKSE-EQQKKNEEELKK-CONH$_2$

Figure 58:
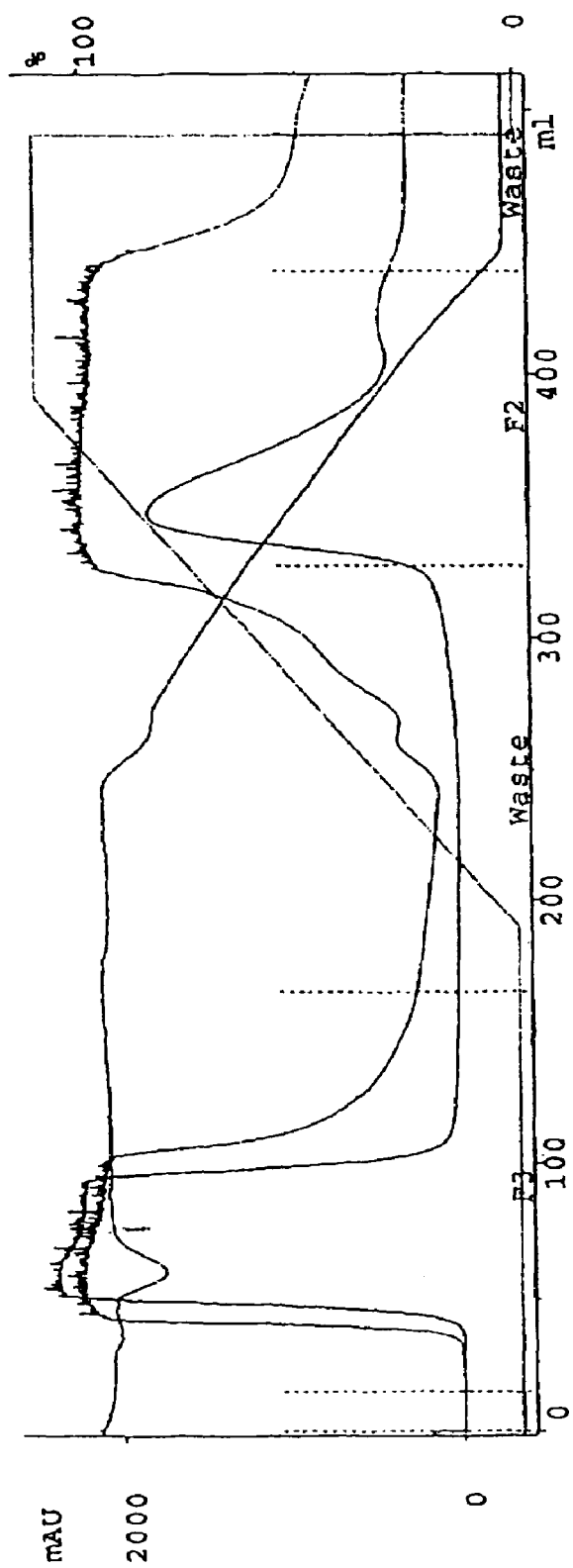
FIG. 58 illustrates the purification of the conjugate HSA: eighth C34 analogue (SEQ ID NO:40) by a preferred embodiment of the method of the present invention.

The purification of a conjugate made from reacting 2 ml 25% HSA with 1 mM eighth C34 analogue in 13 ml of 20 mM sodium phosphate buffer (pH 7.0), 5 mM sodium caprylate and 750 mM (NH$_4$)$_2$SO$_4$, was performed on a column of Butyl sepharose using gradient #1 described above. In FIG. 58 the purified conjugate fraction appears in fraction F2.

EXAMPLE 59

Purification of HSA: First PYY Analogue (SEQ ID NO:41) Conjugate

The first PYY analogue is PYY (3-36) Lys$^4$ ($\epsilon$-OA-MPA)-CONH$_2$ and has the following structure:

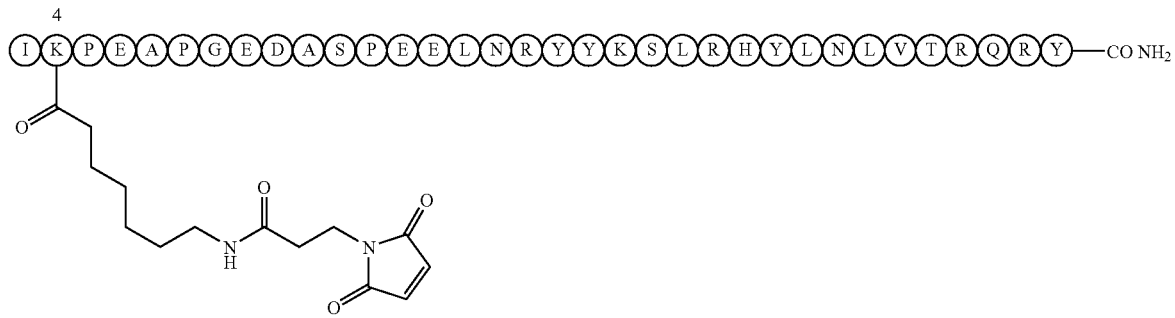

Figure 59:
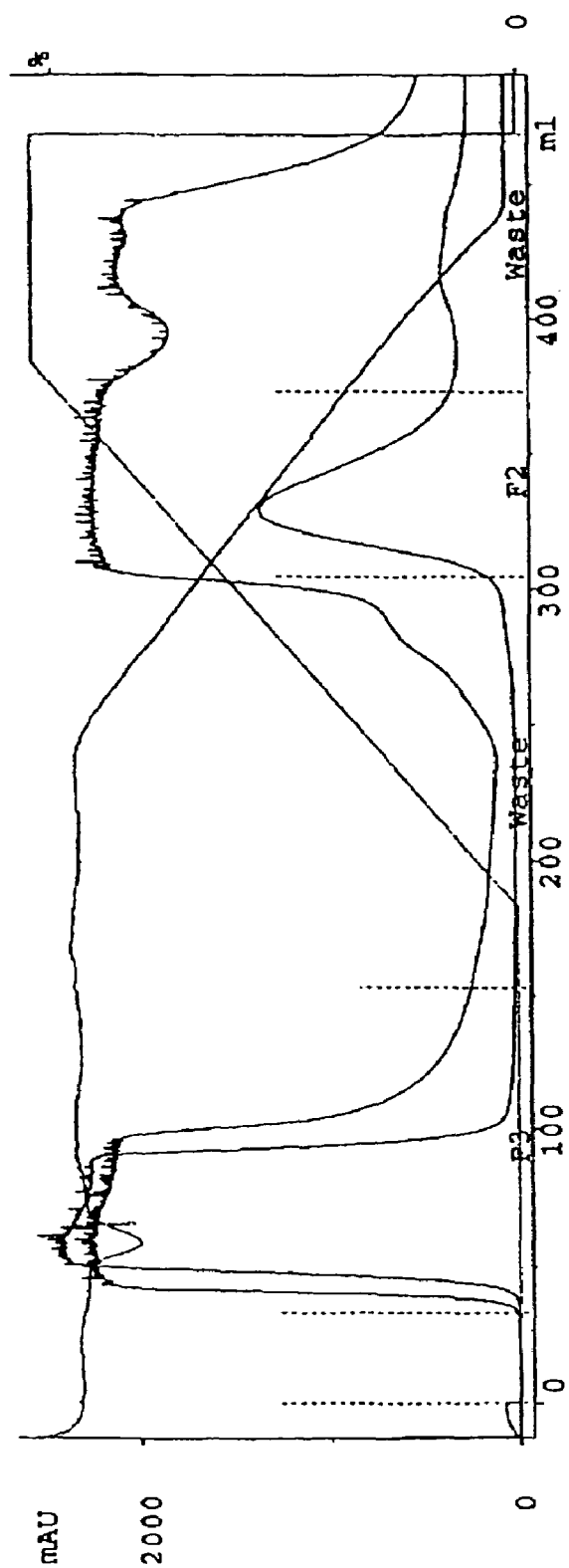
FIG. 59 illustrates the purification of the conjugate HSA: first PYY analogue (SEQ ID NO:41) by a preferred embodiment of the method of the present invention.

The purification of a conjugate made from reacting 1.5 ml 25% HSA with 1 mM first PYY analogue in 6 ml of 20 mM sodium phosphate buffer (pH 7.0), 5 mM sodium caprylate and 750 mM (NH$_4$)$_2$SO$_4$, was performed on a column of Butyl sepharose using gradient #1 described above. In FIG. 59 the purified conjugate fraction appears in fraction F2.

EXAMPLE 60

Purification of HSA: Second PYY Analogue (SEQ ID NO:42) Conjugate

The second PYY analogue is MPA-OA-PYY (3-36)—CONH$_2$ and has the following sequence:

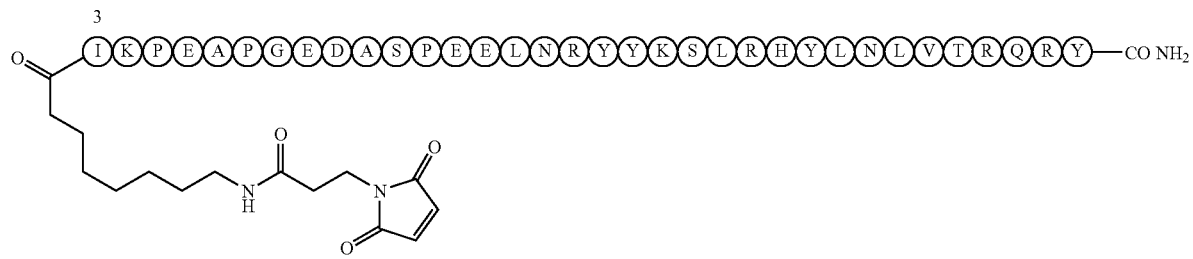

Figure 60:
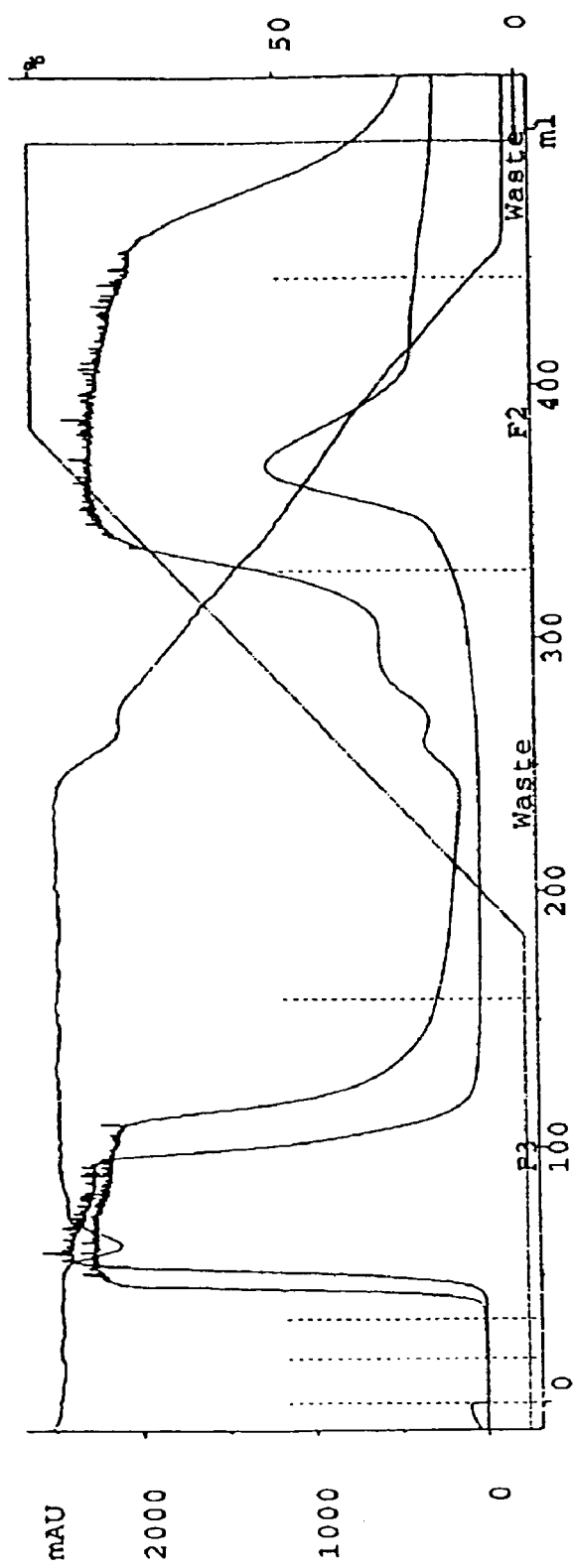
FIG. 60 illustrates the purification of the conjugate HSA: second PYY analogue (SEQ ID NO:42) by a preferred embodiment of the method of the present invention.

The purification of a conjugate made from reacting 1.5 ml 25% HSA with 1 mM second PYY analogue in 6 ml of 20 mM sodium phosphate buffer (pH 7.0), 5 mM sodium caprylate and 750 mM (NH$_4$)$_2$SO$_4$, was performed on a column of Butyl sepharose using gradient #1 described above. In FIG. 60 the purified conjugate fraction appears in fraction F2.

EXAMPLE 61

"Purification of HSA:Fifth Insulin Derivative Conjugate

The fifth insulin derivative is human insulin with AEEAS-AEEAS-MPA on position B29 of B chain (SEQ ID NO: 43) and native A chain (SEQ ID NO: 35); and is represented in FIG. 1 shown above in Example 7."

Figure 61:
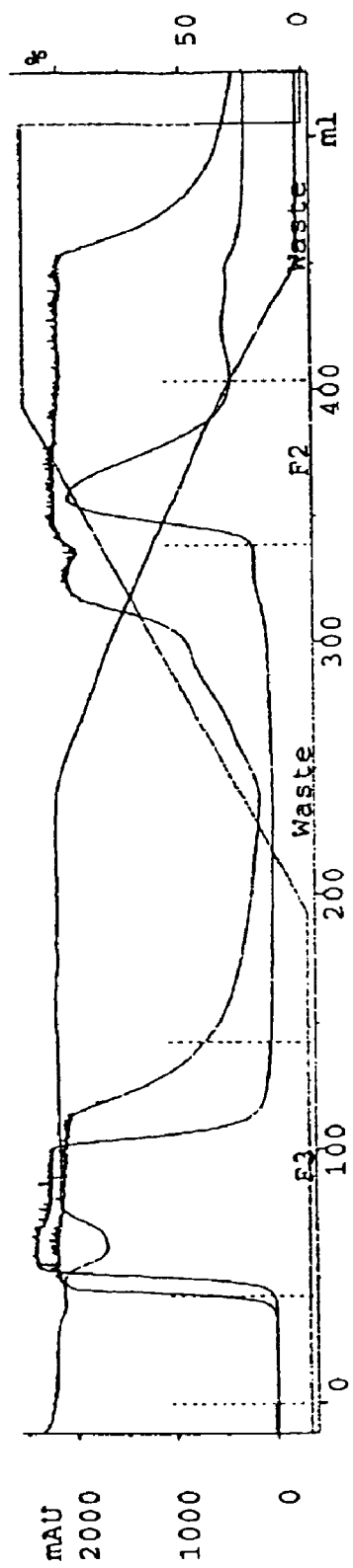
"FIG. 61 illustrates the purification of the conjugate HSA: fifth insulin derivative having modification on chain B (SEQ ID NO:43) by a preferred embodiment of the method of the present invention;"

The purification of a conjugate made from reacting 2 ml 25% HSA with 1 mM fifth insulin derivative in 15 ml of 20 mM sodium phosphate buffer (pH 7.0), 5 mM sodium caprylate and 750 mM (NH$_4$)$_2$SO$_4$ was performed on a column of Butyl sepharose using gradient #1 described above. In FIG. 61 the purified conjugate fraction appears in fraction F2.

EXAMPLE 62

"Purification of HSA: Sixth Insulin Derivative Conjugate

The sixth insulin derivative is human insulin with AEEAS-AEEAS-MPA on position B1 of B chain (SEQ ID NO: 44) and native A chain (SEQ ID NO: 35); and is represented in FIG. 1 shown above in Example 7."

Figure 62:
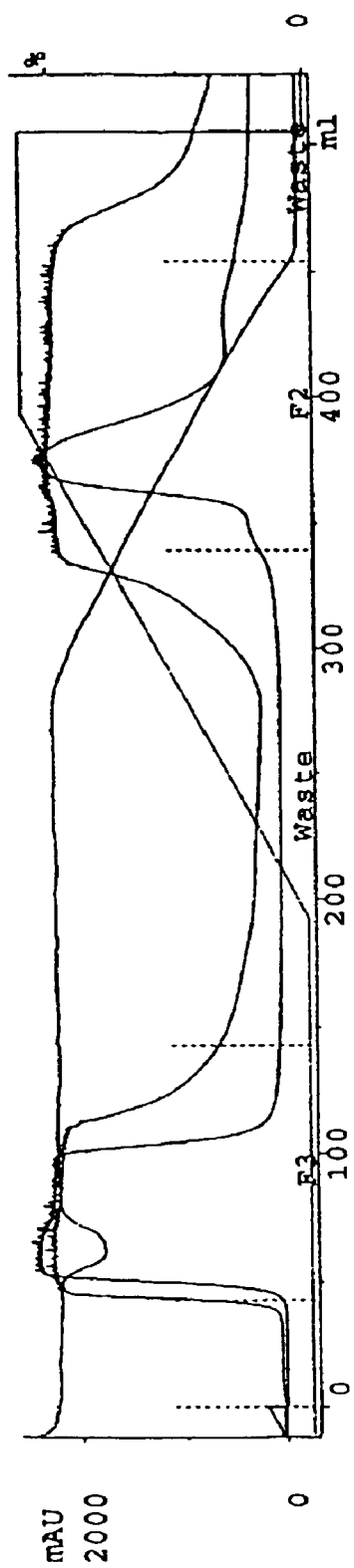
"FIG. 62 illustrates the purification of the conjugate HSA: sixth insulin derivative having modification on chain B (SEQ ID NO:44) by a preferred embodiment of the method of the present invention;"

The purification of a conjugate made from reacting 2.5 ml 25% HSA with 1 mM sixth insulin derivative in 15 ml of 20 mM sodium phosphate buffer (pH 7.0), 5 mM sodium caprylate and 750 mM (NH$_4$)$_2$SO$_4$ was performed on a column of Butyl sepharose using gradient #1 described above. In FIG. 62 the purified conjugate fraction appears in fraction F2.

EXAMPLE 63

"Purification of HSA: Seventh Insulin Derivative Conjugate

The seventh insulin derivative is human insulin with OA-MPA on position B29 of B chain (SEQ ID NO: 45) and native A chain (SEQ ID NO: 35); and is represented in FIG. 1 shown above in Example 7."

Figure 63:
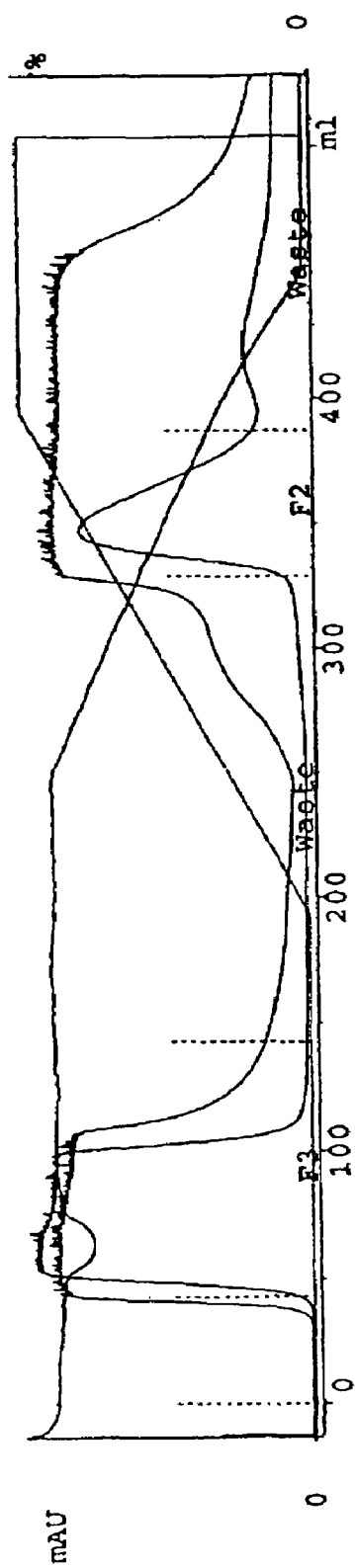
"FIG. 63 illustrates the purification of the conjugate HSA: seventh insulin derivative having modification on chain B (SEQ ID NO:45) by a preferred embodiment of the method of the present invention;"

The purification of a conjugate made from reacting 2 ml 25% HSA with 1 mM seventh insulin derivative in 15 ml of 20 mM sodium phosphate buffer (pH 7.0), 5 mM sodium caprylate and 750 mM (NH$_4$)$_2$SO$_4$ was performed on a column of Butyl sepharose using gradient #1 described above. In FIG. 63 the purified conjugate fraction appears in fraction F2.

EXAMPLE 64

Purification of HSA: Third PYY Analogue (SEQ ID NO:46) Conjugate

The third PYY analogue is MPA-PYY (3-36)—CONH$_2$ and has the following sequence:

MPA-NH-IKPEAPGEDASPEELNRYYASLRHYLN-LVTRQRY-CONH$_2$

Figure 64:
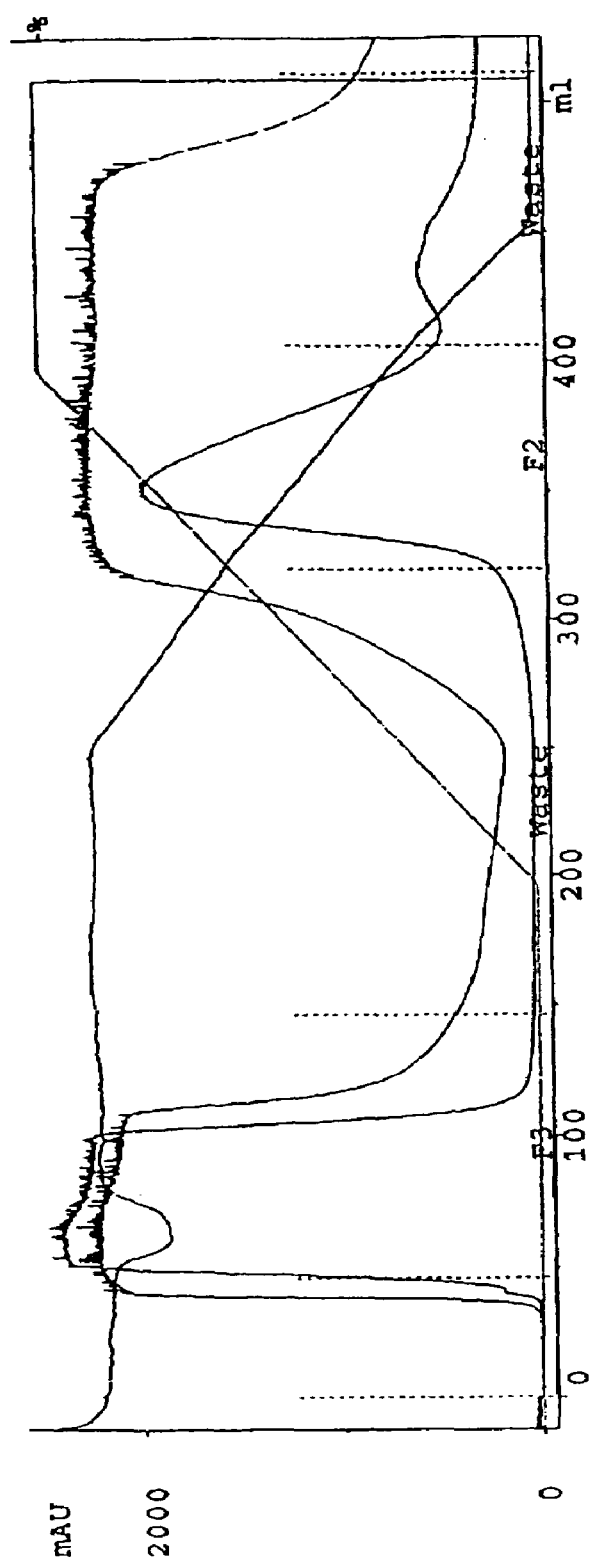
FIG. 64 illustrates the purification of the conjugate HSA: third PYY analogue (SEQ ID NO:46) by a preferred embodiment of the method of the present invention.

The purification of a conjugate made from reacting 3 ml 25% HSA with 1 mM third PYY analogue in 18 ml of 20 mM sodium phosphate buffer (pH 7.0), 5 mM sodium caprylate and 750 mM (NH$_4$)$_2$SO$_4$ was performed on a column of Butyl sepharose using gradient #1 described above. In FIG. 64 the purified conjugate fraction appears in fraction F2.

EXAMPLE 65

Purification of HSA: Fourth PYY Analogue (SEQ ID NO:47) Conjugate

The fourth PYY analogue is PYY (3-36) Lys$^{37}$ ($\epsilon$-MPA)-CONH$_2$ and has the following sequence:

IKPEAPGEDASPEELNRYYASLRHYLNLVTRQRYK (MPA)-CONH$_2$

Figure 65:
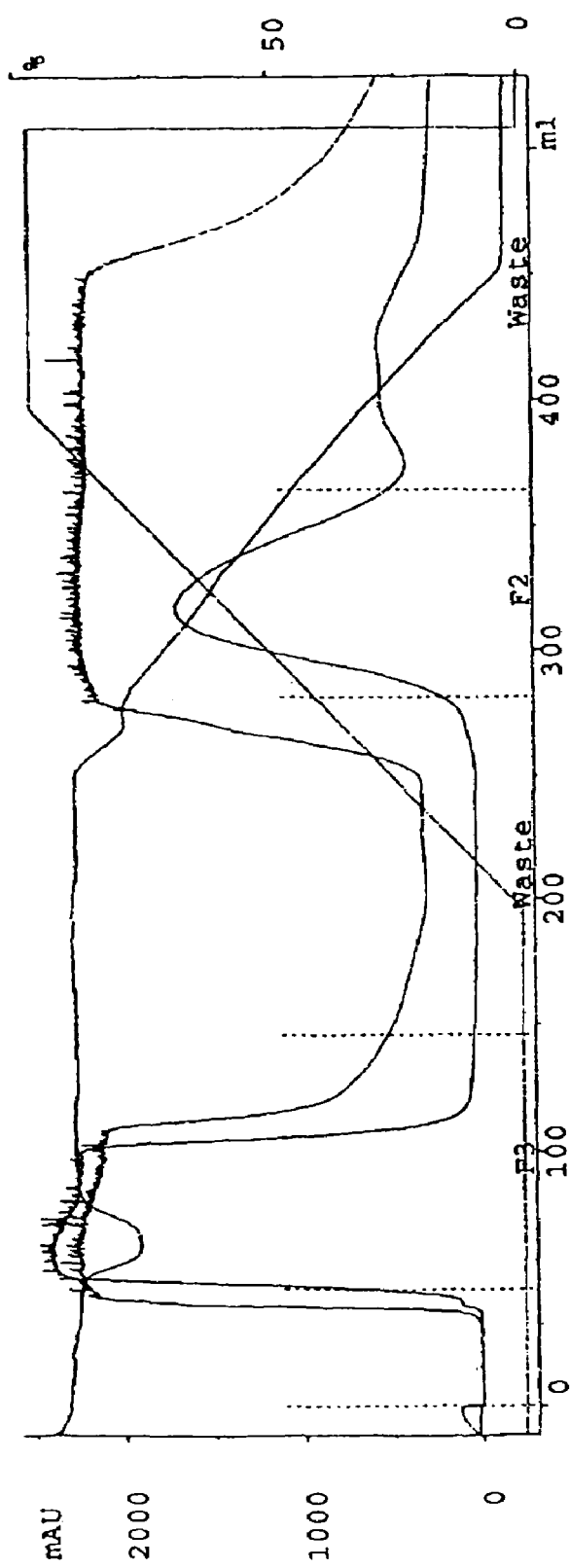
FIG. 65 illustrates the purification of the conjugate HSA: fourth PYY analogue (SEQ ID NO:47) by a preferred embodiment of the method of the present invention.

The purification of a conjugate made from reacting 3 ml 25% HSA with 1 mM fourth PYY analogue in 18 ml of 20 mM sodium phosphate buffer (pH 7.0), 5 mM sodium caprylate and 750 mM (NH$_4$)$_2$SO$_4$ was performed on a column of Butyl sepharose using gradient #1 described above. In FIG. 65 the purified conjugate fraction appears in fraction F2.

EXAMPLE 66

Purification of HSA: Fifth PYY Analogue (SEQ ID NO:48) Conjugate

The fifth PYY analogue is MPA-PYY (22-36)—CONH$_2$ and has the following sequence: (MPA)-ASLRHYLN-LVTRQRY-CONH$_2$.

Figure 66:
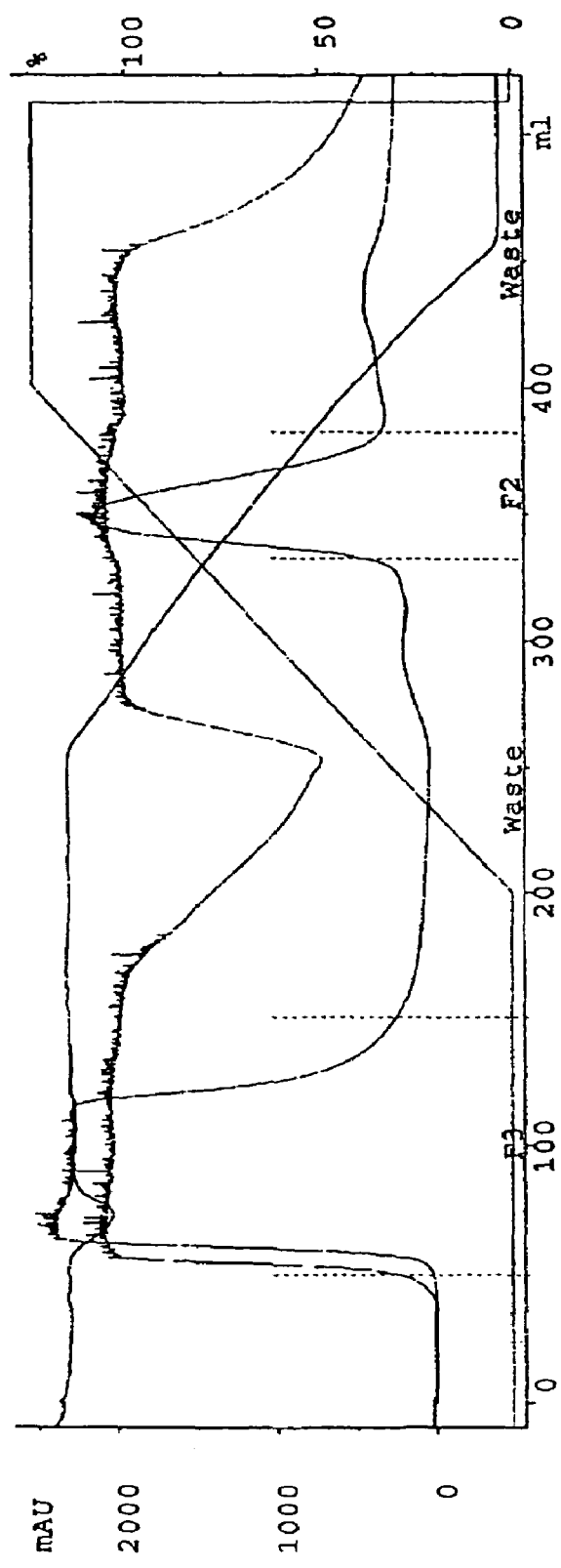
FIG. 66 illustrates the purification of the conjugate HSA: fifth PYY analogue (SEQ ID NO:48) by a preferred embodiment of the method of the present invention.

The purification of a conjugate made from reacting 6 ml 25% HSA with 1 mM fifth PYY analogue in 36 ml of 20 mM sodium phosphate buffer (pH 7.0), 5 mM sodium caprylate and 900 mM (NH$_4$)$_2$SO$_4$ was performed on a column of Butyl sepharose using gradient #3 described above. In FIG. 66 the purified conjugate fraction appears in fraction F2.

EXAMPLE 67

Purification of HSA: Sixth PYY Analogue (SEQ ID NO:49) Conjugate

The sixth PYY analogue is Acetyl-PYY (22-36) Lys$^{37}$ ($\epsilon$-MPA)-CONH$_2$ and has the following sequence: Ac-ASL-RHYLNLVTRQRYK(MPA)-CONH$_2$.

Figure 67:
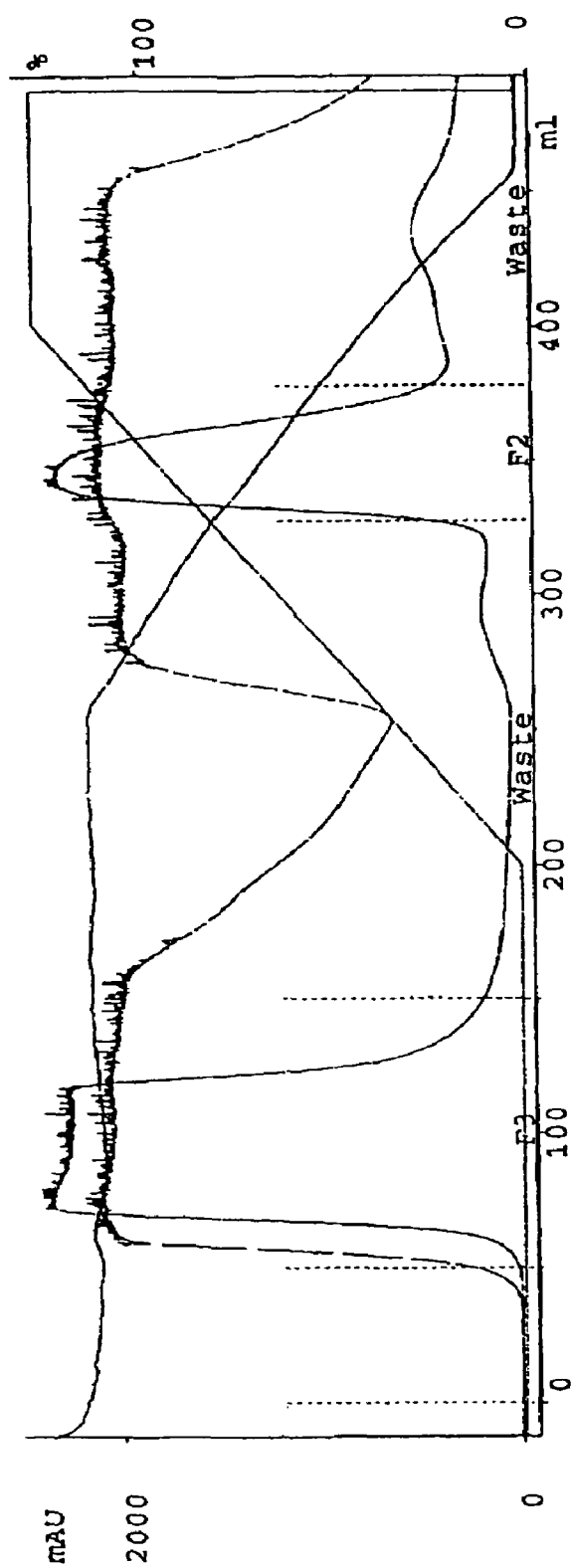
FIG. 67 illustrates the purification of the conjugate HSA: sixth PYY analogue (SEQ ID NO:49) by a preferred embodiment of the method of the present invention.

The purification of a conjugate made from reacting 6 ml 25% HSA with 1 mM sixth PYY analogue in 36 ml of 20 mM sodium phosphate buffer (pH 7.0), 5 mM sodium caprylate and 900 mM (NH$_4$)$_2$SO$_4$ was performed on a column of Butyl sepharose using gradient #3 described above. In FIG. 67 the purified conjugate fraction appears in fraction F2.

EXAMPLE 68

Purification of HSA: Second ANP Analogue (SEQ ID NO:50) Conjugate

The second ANP analogue is MPA-ANP (99-126)—CONH$_2$ and has the following structure:

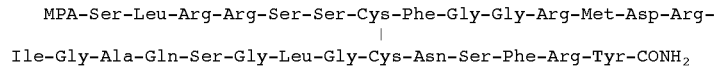

Figure 68:
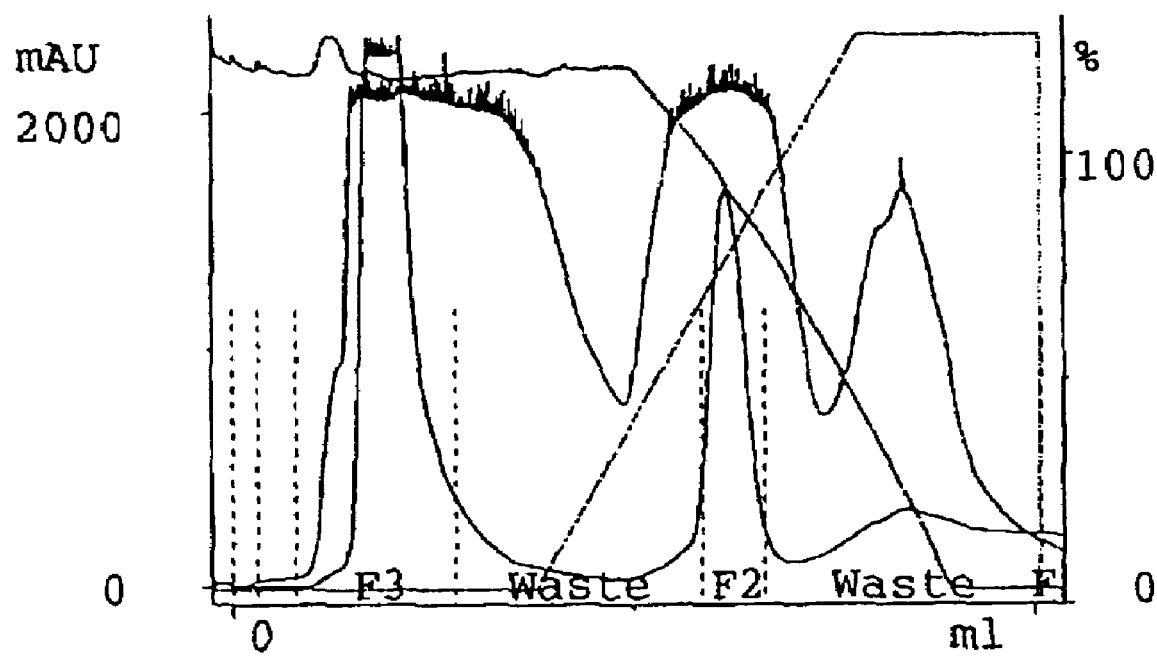
FIG. 68 illustrates the purification of the conjugate HSA: second ANP analogue (SEQ ID NO:50) by a preferred embodiment of the method of the present invention.

The purification of a conjugate made from reacting 1 ml 25% HSA with 1 mM second ANP analogue in 14 ml of 20 mM sodium phosphate buffer (pH 7.0), 5 mM sodium caprylate and 750 mM $(NH_4)_2SO_4$ was performed on a column of Butyl sepharose using gradient #3 described above. In FIG. 68 the purified conjugate fraction appears in fraction F2.

EXAMPLE 69

Purification of HSA: Third ANP Analogue (SEQ ID NO:51) Conjugate

The third ANP analogue is ANP (99-126) having reacted with MAL-dPEG$_4$™ (Quanta Biodesign, Powell, Ohio, USA) coupled to Ser$^{99}$. The resulting ANP analogue is MPA-EEEEP-ANP (99-126) where EEEEP is ethoxy ethoxy ethoxy ethoxy propionic acid; and its sequence is the following:

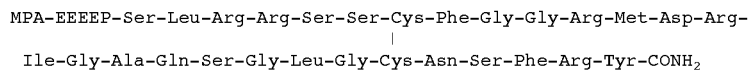

The purification of a conjugate made from reacting 1 ml 25% HSA with 1 mM CJC 1681 in 14 ml of 20 mM sodium phosphate buffer (pH 7.0), 5 mM sodium caprylate and 900 mM $(NH_4)_2SO_4$ was performed on a column of Butyl sepharose using gradient #3 described above. In FIGS. 69A and 69B the purified conjugate fraction appears in fraction F2.

EXAMPLE 70

Purification of HSA: First GLP-1 Analogue (SEQ ID NO:1) Conjugate

The first GLP-1 analogue is GLP-1 (7-36) dAla$^8$ Lys$^{37}$ ($\epsilon$-AEEA-MPA)-CONH$_2$ and his sequence is shown above in Example 1.

Figure 70:
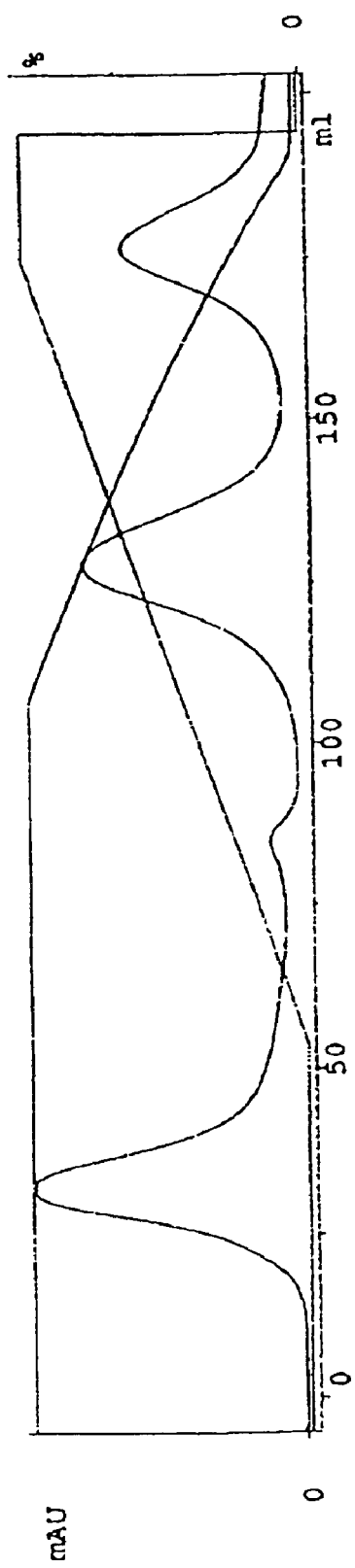
FIG. 70 illustrates the purification of the conjugate HSA: first GLP-1 analogue (SEQ ID NO:1) by a preferred embodiment of the method of the present invention.

The purification of a conjugate made from reacting 1 ml 25% 250 mg/ml HSA (Cortex-Biochem, San Leandro, Calif.) with 1 mM first GLP-1 analogue diluted into 9 ml of buffer made of 20 mM sodium phosphate buffer pH 7.0, 5 mM sodium caprylate and 1.75M $(NH_4)_2SO_4$, was performed on a column of Butyl sepharose using the gradient #6 described above. In FIG. 70 the purified conjugate fraction appears in fraction B.

EXAMPLE 71

Purification of HSA: First GLP-1 Analogue (SEQ ID NO:1) Conjugate

The first GLP-1 analogue is GLP-1 (7-36) dAla$^8$ Lys$^{37}$ ($\epsilon$-AEEA-MPA)-CONH$_2$ and his sequence is shown above in Example 1.

Figure 71:
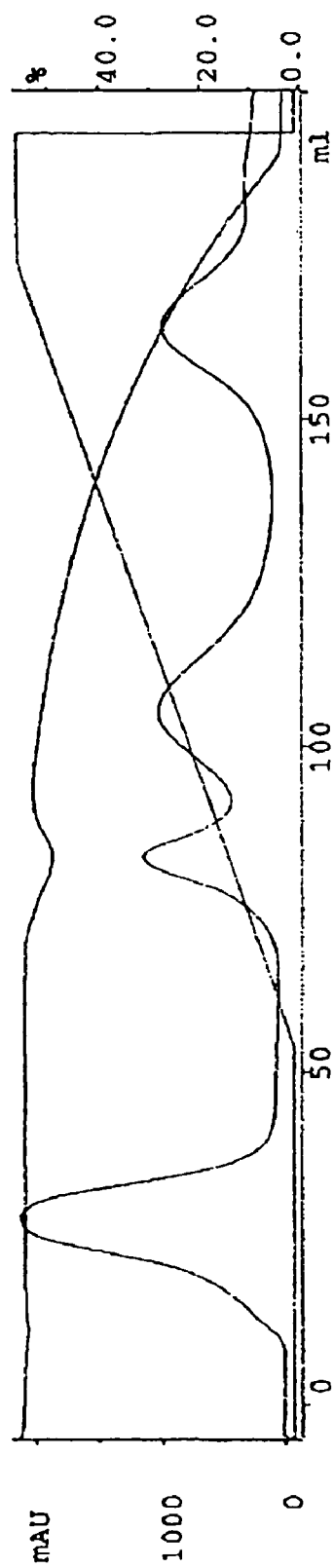
FIG. 71 illustrates the purification of the conjugate HSA: first GLP-1 analogue (SEQ ID NO:1) by a preferred embodiment of the method of the present invention.

The purification of a conjugate made from reacting 1 ml 25% 250 mg/ml HSA (Cortex-Biochem, San Leandro, Calif.) with 1 mM first GLP-1 analogue diluted into 9 ml of buffer made of 20 mM sodium phosphate buffer pH 7.0, 5 mM sodium caprylate and 1.75M magnesium sulfate, was performed on a column of Butyl sepharose using the gradient #6 described above. In FIG. 71 the purified conjugate fraction appears in fraction F2.

EXAMPLE 72

Purification of HSA: First GLP-1 Analogue (SEQ ID NO:1) Conjugate

The first GLP-1 analogue is GLP-1 (7-36) dAla$^8$ Lys$^{37}$ ($\epsilon$-AEEA-MPA)-CONH$_2$ and his sequence is shown above in Example 1.

Figure 72:
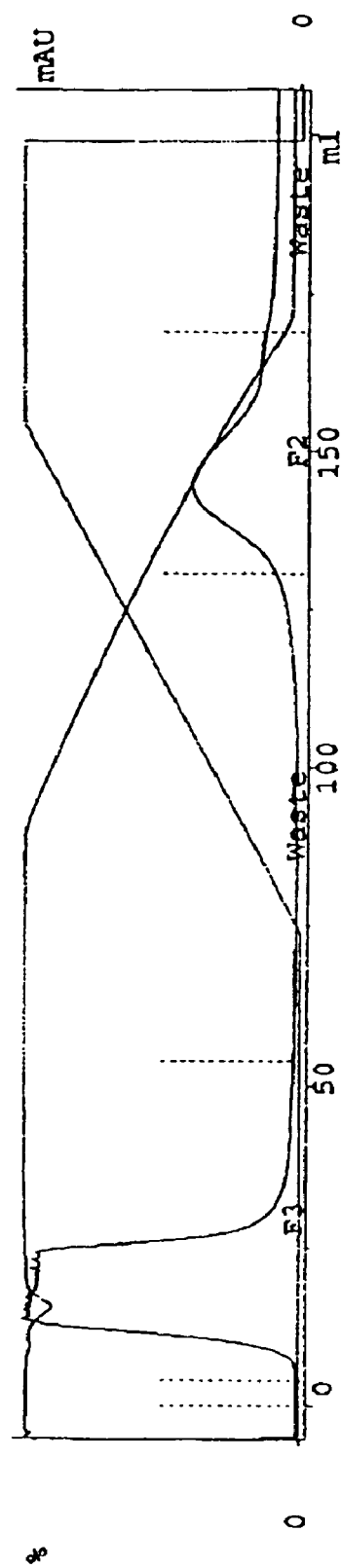
FIG. 72 illustrates the purification of the conjugate HSA: first GLP-1 analogue (SEQ ID NO:1) by a preferred embodiment of the method of the present invention.

Example with 750 mM ammonium sulfate The purification of a conjugate made from reacting 1 ml 25% 250 mg/ml HSA (Cortex-Biochem, San Leandro, Calif.) with 1 mM first GLP-1 analogue diluted into 9 ml of buffer made of 20 mM sodium phosphate buffer pH 7.0, 5 mM sodium caprylate and 750 mM $(NH_4)_2SO_4$, was performed on a column of Butyl sepharose using the gradient #1 described above. In FIG. 72 the purified conjugate fraction appears in fraction F2.

EXAMPLE 73

Purification of HSA: First GLP-1 Analogue (SEQ ID NO:1) Conjugate

The first GLP-1 analogue is GLP-1 (7-36) dAla$^8$ Lys$^{37}$ ($\epsilon$-AEEA-MPA)-CONH$_2$ and his sequence is shown above in Example 1.

Figure 73:
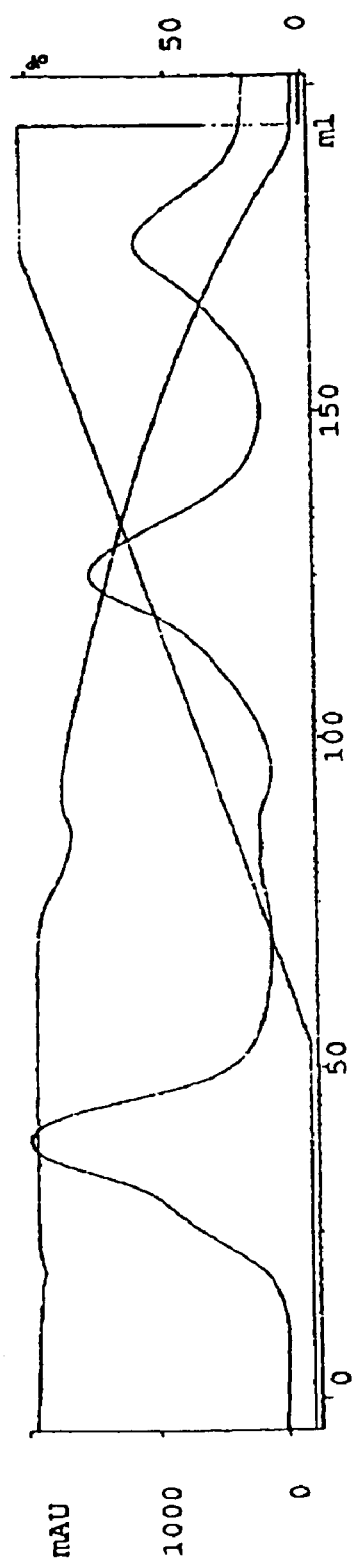
FIG. 73 illustrates the purification of the conjugate HSA: first GLP-1 analogue (SEQ ID NO:1) by a preferred embodiment of the method of the present invention.

Example with 1.75M ammonium phosphate The purification of a conjugate made from reacting 1 ml 25% 250 mg/ml HSA (Cortex-Biochem, San Leandro, Calif.) with 1 mM first GLP-1 analogue diluted into 9 ml of buffer made of 20 mM sodium phosphate buffer pH 7.0, 5 mM sodium caprylate and 1.75M ammonium phosphate, was performed on a column of Butyl sepharose using the gradient #6 described above. In FIG. 73 the purified conjugate fraction appears in fraction B.

EXAMPLE 74

Purification of HSA: First GLP-1 Analogue (SEQ ID NO:1) Conjugate

The first GLP-1 analogue is GLP-1 (7-36) dAla$^8$ Lys$^{37}$ ($\epsilon$-AEEA-MPA)-CONH$_2$ and his sequence is shown above in Example 1.

Figure 74:
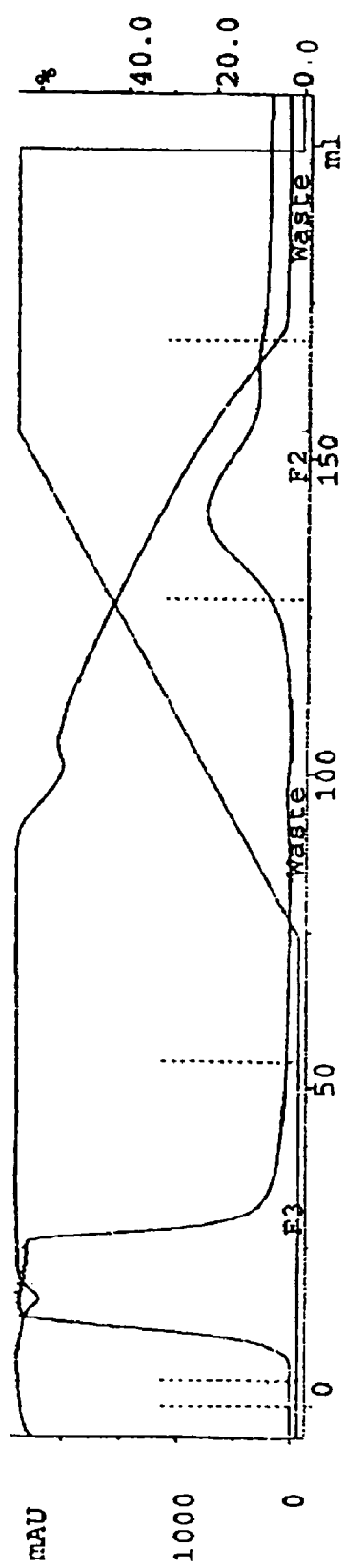
FIG. 74 illustrates the purification of the conjugate HSA: first GLP-1 analogue (SEQ ID NO:1) by a preferred embodiment of the method of the present invention.

Example with 750 mM ammonium phosphate The purification of a conjugate made from reacting 1 ml 25% 250 mg/ml HSA (Cortex-Biochem, San Leandro, Calif.) with 1 mM first GLP-1 analogue diluted into 9 ml of buffer made of 20 mM sodium phosphate buffer pH 7.0, 5 mM sodium caprylate and 750 mM ammonium phosphate, was performed on a column of Butyl sepharose using the gradient #1 described above. In FIG. 74 the purified conjugate fraction appears in fraction F2.

EXAMPLE 75

Purification of HSA: First GLP-2 Analogue (SEQ ID NO:52) Conjugate

The first GLP-2 analogue is GLP-2 (1-33) $Gly^2$ $Lys^{34}$ ($\epsilon$-MPA)-$CONH_2$ and has the following sequence:

HGDGSFSDEMNTILDNLAARDFINWLIQTKITDK (MPA)-$CONH_2$

Figure 75:
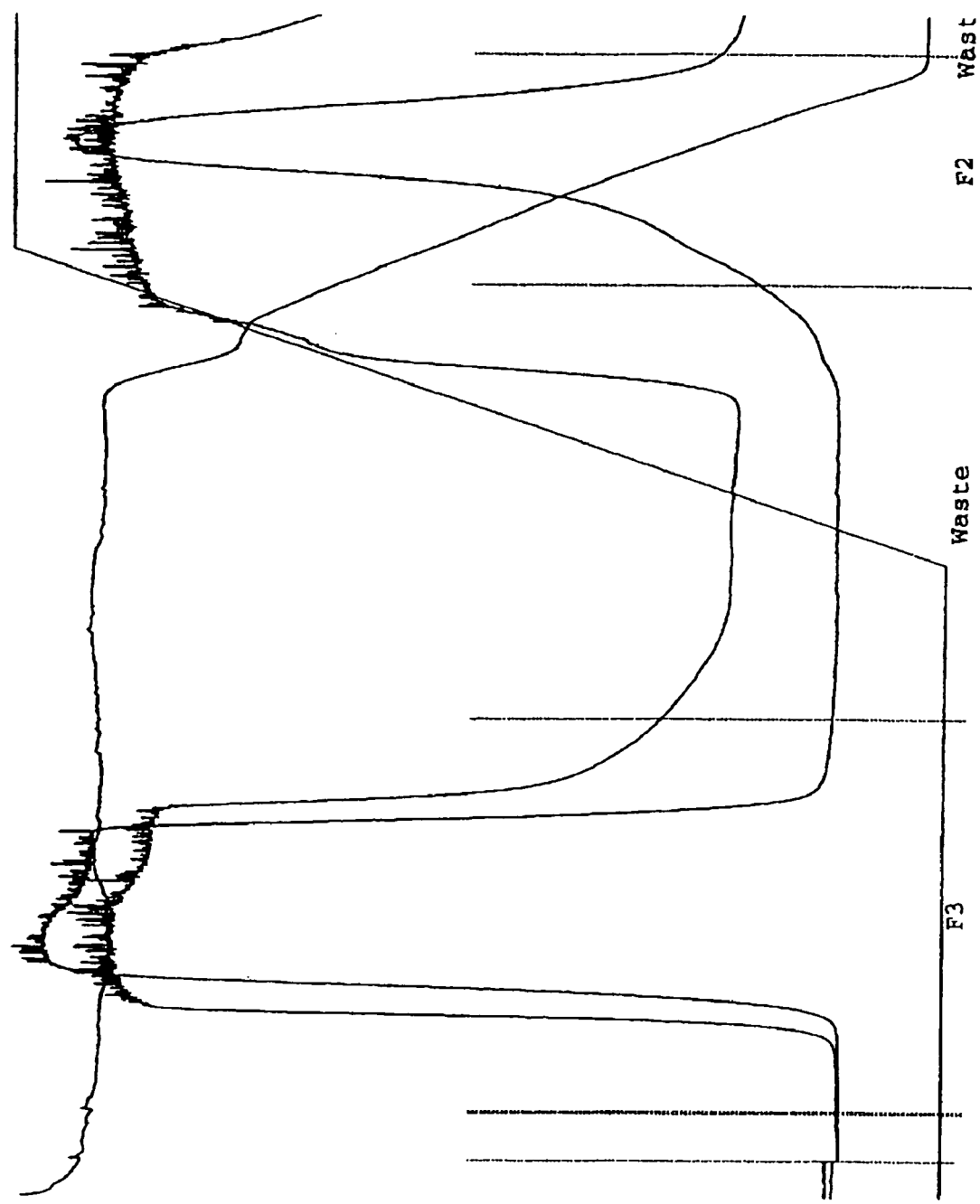
FIG. 75 illustrates the purification of the conjugate HSA: first GLP-2 analogue (SEQ ID NO:52) by a preferred embodiment of the method of the present invention.

The purification of a conjugate made from reacting 2 ml 25% 250 mg/ml HSA (Cortex-Biochem, San Leandro, Calif.) with 1 mM first GLP-2 analogue diluted into 14 ml of buffer made of 20 mM sodium phosphate buffer pH 7.0, 5 mM sodium caprylate and 750 mM $(NH_4)_2SO_4$, was performed on a column of Butyl sepharose using the gradient #1 described above. In FIG. 75 the purified conjugate fraction appears in fraction F2.

EXAMPLE 76

Purification of RSA: First GLP-2 Analogue (SEQ ID NO:52) Conjugate

The first GLP-2 analogue is GLP-2 (1-33) $Gly^2$ $Lys^{34}$ ($\epsilon$-MPA)-$CONH_2$ and his sequence is shown in Example 75.

Figure 76:
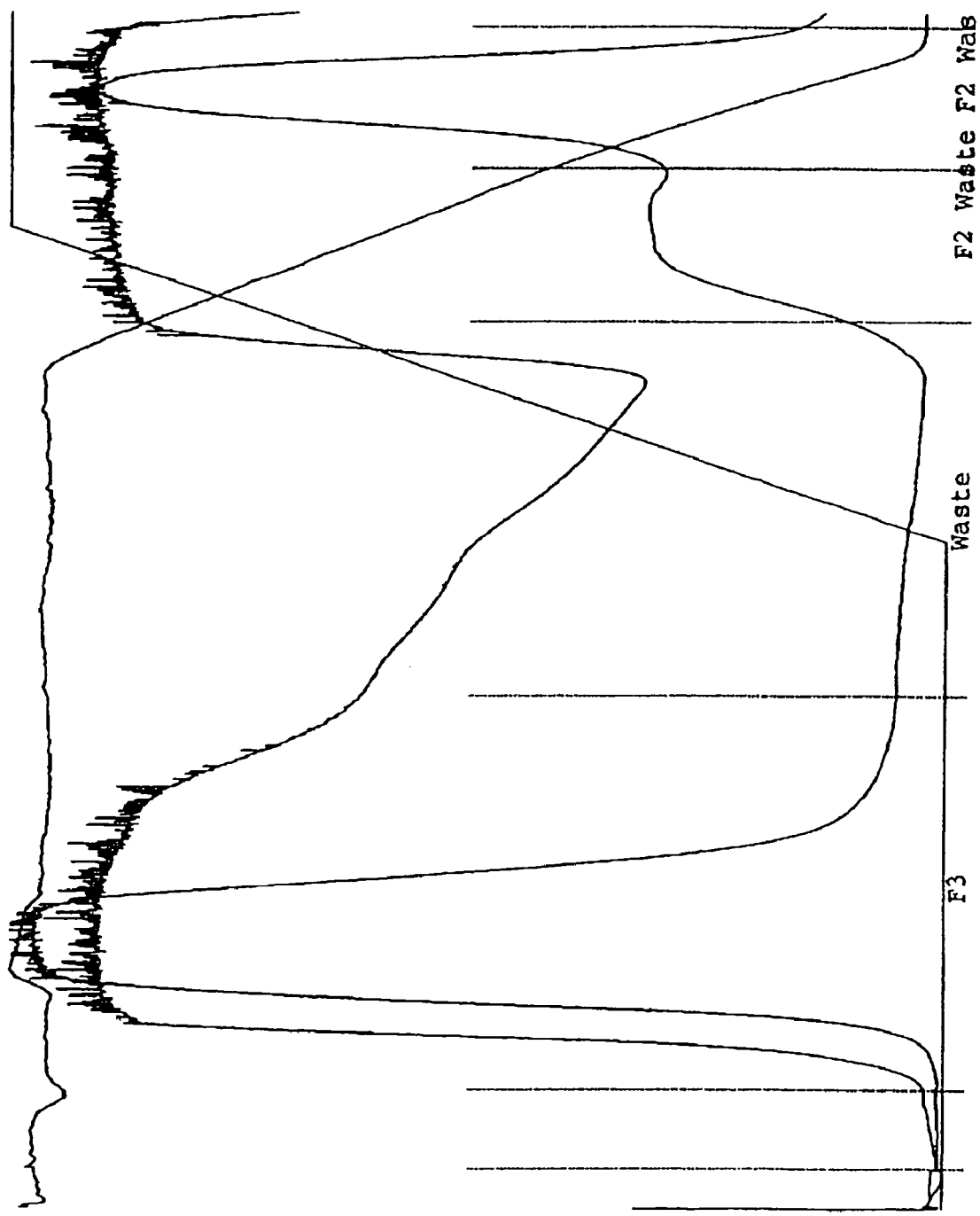
FIG. 76 illustrates the purification of the conjugate RSA: first GLP-2 analogue (SEQ ID NO:52) by a preferred embodiment of the method of the present invention.

The purification of a conjugate made from reacting 9 ml 25% 250 mg/ml RSA (rat serum albumin) with 1 mM first GLP-2 analogue diluted into 14 ml of buffer made of 20 mM sodium phosphate buffer pH 7.0, 5 mM sodium caprylate and 750 mM $(NH_4)_2SO_4$, was performed on a column of Butyl sepharose using the gradient #1 described above. In FIG. 76 the purified conjugate fraction appears in fraction F2.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

What is claimed is:

1. A method for separating albumin conjugate from unconjugated albumin in a solution comprising albumin conjugate and unconjugated albumin, the method comprising:
   a) loading said solution onto a hydrophobic interaction chromatography matrix equilibrated in aqueous buffer at a salt concentration high enough to promote matrix-protein interactions;
   b) applying to said matrix a gradient of decreasing salt concentration; and
   c) collecting said albumin conjugate.

2. The method of claim 1, wherein said albumin conjugate consists of a molecule comprising a Michael acceptor covalently bonded to albumin.

3. The method of claim 2, wherein said Michael acceptor is a maleimide group.

4. The method of claim 3, wherein said maleimide group is maleimid-propionic acid.

5. The method of claim 1, wherein said albumin is selected from the group consisting of serum albumin and recombinant albumin.

6. The method of claim 1, wherein said albumin is selected from the group consisting of human albumin, rat albumin, mouse albumin, swine albumin, bovine albumin, dog albumin, and rabbit albumin.

7. The method of claim 1, wherein said albumin is human serum albumin.

8. The method of claim 1, wherein said albumin is modified with a fatty acid, a metal ion, a sugar, or a combination thereof.

9. The method of claim 8, wherein said sugar is selected from the group consisting of glucose, lactose, and mannose.

10. The method of claim 2, wherein said molecule is selected from the group consisting of a peptide, a DNA, an RNA, and a combination thereof, to which said Michael acceptor is covalently bonded, optionally through a linker.

11. The method of claim 10, wherein said molecule is a peptide having a molecular weight of at least 57 daltons.

12. The method of claim 10, wherein said peptide is selected from the group consisting of glucagon like peptide 1 (GLP-1), atrial natriuretic peptide (ANP), kringle 5 (KS), dynorphin, exendin-4, growth hormone releasing factor (GRF), insulin, natriuretic peptides, enfuvirtide (T-20), T-1249, C-34, soluble C-35 peptide BK (SC-35), peptide YY (PYY), and analogs thereof.

13. The method of claim 10, wherein said molecule is selected from the group consisting of:
   3',4'-didehydro-4'-deoxy-C'-norvincaleukoblastine;
   2'-deoxy-2',2'-difluorocytidine; and
   5β,20-epoxy-1 ,2α,4,7β,10β,13α-hexahydroxy-tax-11-en-9-one, 4,10-diacetate 2-benzoate, 13-ester with (2R, 3S)-N-benzoyl-3-phenylisoserine.

14. The method of claim 10, wherein said molecule is covalently attached to said albumin through an acid sensitive covalent bond or a peptide sequence susceptible to proteolytic cleavage, thereby allowing the separation of said molecule and albumin and the entry of the molecule into a cell.

15. The method of claim 1, wherein said hydrophobic interaction chromatography matrix is a column containing a hydrophobic resin.

16. The method of claim 15, wherein said hydrophobic resin is a bead-formed agarose-based gel filtration matrix covalently coupled to a ligand selected from the group consisting of an octyl group, a phenyl group, and a butyl group.

17. The method of claim 15, wherein said hydrophobic resin is a bead-formed agarose-based gel filtration matrix covalently coupled to a butyl group.

18. The method of claim 1, wherein said gradient of decreasing salt concentration has a starting salt concentration of between 500 and 3000 mM.

19. The method of claim 1, wherein said salt is selected from the group consisting of ammonium phosphate, ammonium sulfate, and magnesium phosphate.

20. The method of claim 1, wherein said salt is ammonium phosphate or ammonium sulfate.

21. The method of claim 1, wherein said salt is ammonium sulfate.

22. The method of claim 2, wherein said bond is between said Michael acceptor and cysteine 34 of said albumin.

23. The method of claim 2, 3, or 4, wherein said molecule is a peptide to which said Michael acceptor is covalently bonded, optionally through a linker.

24. The method of claim 23, wherein said peptide is an analog of glucagon like peptide 1 (GLP-1), glucagon like peptide 2 (GLP-2), atrial natriuretic peptide (ANP), kringle 5 (KS), dynorphin, exendin-4, growth hormone releasing factor (GRF), insulin, natriuretic peptides, enfuvirtide (T-20), T-1249, C-34, soluble C-35 peptide EK (SC-35), or peptide YY (PYY).

25. The method of claim 2, 3, or 4, wherein said molecule is selected from the group consisting of GLP-1 (7-36) dAla$^8$ Lys$^{37}$ (ε-AEEA-MPA)-CONH$_2$ (SEQ ID NO:1),GRF (1-29)

dAla² Gln⁸ Ala¹⁵ Leu²⁷ Lys³⁰ (ε-MPA) CONH₂ (SEQ ID NO:2), Ac-K5 Lys⁸ (ε-MPA)-NH₂ (SEQ ID NO:3), Insulin B1-MPA (SEQ ID NO:4), Insulin A1-MPA (SEQ ID NO:5), MPA-AEEA-C34-CONH₂ (SEQ ID NO:6), C34 (1-34) Lys³³ (ε-AEEA-MPA)-CONH₂ (SEQ ID NO:7), C34 (1-34) Lys¹³ (ε-AEEA-MPA)-CONH₂ (SEQ ID NO:8), GLP-1 (7-36) Lys³⁷ (ε-MPA)-NH₂ (SEQ ID NO:9), GLP-1 (7-36) dAla⁸ Lys³⁷ (ε-MPA)-NH₂ (SEQ ID NO:10), GLP-1 (7-36) Lys²⁶ (ε-AEEA-AEEA-MPA) (SEQ ID NO:11), GLP-1 (7-36) Lys³⁴ (ε-AEEA-AEEA-MPA) (SEQ ID NO:12), Exendin-4-(1-39) Lys⁴⁰ (ε-MPA)-NH₂ (SEQ ID NO:13), Exendin-4 (9-39) Lys⁴⁰ (ε-AEEA-MPA)-CONH₂ (SEQ ID NO:14), Dyn A (1-13) (MPA)-NH₂ (SEQ ID NO:15), MPA-AEEA-ANP (99-126)-CONH₂ (SEQ ID NO:16), Dyn A (7-13) Lys¹³ (ε-MPA)-CONH₂ (SEQ ID NO:17), acetyl-Phe-His-cyclohexylstatyl-Ile-Lys (ε-AEEA-MPA)-CONH₂ (SEQ ID NO:18), GLP-1 (7-36) Lys²³ (ε-AEEA-MPA)-CONH₂ (SEQ ID NO:19), GLP-1 (7-36) Lys¹⁸ (ε-AEEA-MPA)-CONH₂ (SEQ ID NO:20), GLP-1 (7-36) Lys²⁶ (ε-AEEA-MPA)-CONH₂ (SEQ ID NO:21), GLP-1 (7-37) Lys²⁷ (ε-AEEA-MPA)-CONH₂ (SEQ ID NO:22), GLP-1 (7-36) Lys³⁷ (ε-AEEA-AEEA-MPA)-CONH₂ (SEQ ID NO:23), GLP-1 (7-36) Lys³⁷ (ε-AEEA-MPA)-CONH₂ (SEQ ID NO:24), Exendin-4-(1-39) Lys⁴⁰ (ε-AEEA-MPA)-CONH₂ (SEQ ID NO:25), GLP-1 (7-36) Lys³⁴ (ε-AEEA-MPA)-CONH₂ (SEQ ID NO:26), Insulin B1-OA-MPA (SEQ ID NO:27), Insulin B29-MPA (SEQ ID NO:28), GRF (1-29) Lys³⁰ (ε-MPA)-CONH₂ (SEQ ID NO:29), GRF (1-29) dAla² Gln⁸ dArg¹¹ Ala¹⁵ Leu²⁷ Lys³⁰ (ε-MPA)-CONH₂ (SEQ ID NO:30), GRF (1-29) dAla² Lys³⁰ (ε-MPA)-CONH₂ (SEQ ID NO:31), GLP-1 (9-36) Lys³⁷ (ε-AEEA-MPA)-CONH₂ (SEQ ID NO:32), Ac-T20 (1-36) Lys³⁷ (ε-AEEA-MPA)-CONH₂ (SEQ ID NO:33), Ac-T1249 (1-39) Lys⁴⁰ (ε-AEEA-MPA)-CONH₂ (SEQ ID NO:34), 3',4'-didehydro-4'-deoxy-C'-nor-vincaleukoblastine -AEEA-MPA, C34 (1-34) Lys¹³ (ε-MPA)-CONH₂ (SEQ ID NO:36), C34 (1-34) Lys³⁵ (ε-MPA)-CONH₂ (SEQ ID NO:37), MPA-C34 (1-34)-CONH₂ (SEQ ID NO:38), Ac-C34 (1-34) Glu² Lys⁶ Lys⁷ Glu⁹ Glu¹⁰ Lys¹³ Lys¹⁴ Glu¹⁶ Glu¹⁷ Lys²⁰ Lys²¹ Glu²³ Glu²⁴ Lys²⁷ Glu³¹ Lys³⁴ Lys³⁵ Lys³⁶(ε-AEEA-MPA)-CONH₂ (SEQ ID NO:39), MPA-AEEA-C34 (1-34) Glu² Lys⁶ Lys⁷ Glu⁹ Glu¹⁰ Lys¹³ Lys¹⁴ Glu¹⁶ Glu¹⁷ Lys²¹ Glu²³ Glu²⁴ Lys²⁷ Glu³¹ Lys³⁴ Lys³⁵ CONH₂ (SEQ ID NO:40), PYY (3-36) Lys⁴ (ε-OA-MPA)-CONH₂ (SEQ ID NO:41), MPA-OA-PYY (3-36)-CONH₂ (SEQ ID NO:42), Insulin B29-AEES2-MPA (SEQ ID NO:43), Insulin B1-AEES2-MPA (SEQ ID NO:44), Insulin B29-OA-MPA (SEQ ID NO:45), MPA-PYY (3-36)-CONH₂ (SEQ ID NO:46), PYY (3-36) Lys³⁷ (ε-MPA)-CONH₂ (SEQ ID NO:47), MPA-PYY (22-36)-CONH₂ (SEQ ID NO:48), Acetyl-PYY (22-36) Lys³⁷ (ε-MPA)-CONH₂ (SEQ ID NO:49), MPA-ANP (99-126)-CONH₂ (SEQ ID NO:50), MPA-EEEEP-ANP (99-126) (SEQ ID NO:51), and GLP-2 (1-33) Gly² Lys³⁴ (ε-MPA)-CONH₂ (SEQ ID NO:52).

26. The method of claim 24, wherein said peptide is GLP-1 (7-36) dAla⁸ Lys³⁷.

27. The method of claim 24, wherein said peptide is Exendin-4 (1-39) Lys⁴⁰.

28. The method of claim 2, 3, or 4, wherein said molecule is GLP-1 (7-36) dAla⁸ Lys³⁷ (ε-AEEA-MPA)-CONH₂.

* * * * *

UNITED STATES PATENT AND TRADEMARK OFFICE
CERTIFICATE OF CORRECTION

PATENT NO. : 7,307,148 B2  Page 1 of 1
APPLICATION NO. : 11/112277
DATED : December 11, 2007
INVENTOR(S) : Nathalie Bousquet-Gagnon, Omar Quraishi and Dominique P. Bridon It is certified that error appears in the above-identified patent and that said Letters Patent is hereby corrected as shown below:

In claim 12, col. 63, line 66, "soluble C-35 peptide BK (SC-35)" should be replaced with -- soluble C-35 peptide EK (SC-35) --.

Signed and Sealed this

Thirteenth Day of May, 2008

JON W. DUDAS
*Director of the United States Patent and Trademark Office*

(12) EX PARTE REEXAMINATION CERTIFICATE (9027th)
United States Patent
Bousquet-Gagnon et al.

(10) Number: US 7,307,148 C1
(45) Certificate Issued: May 22, 2012

(54) METHOD FOR PURIFICATION OF ALBUMIN CONJUGATES

(75) Inventors: Nathalie Bousquet-Gagnon, St-Jérôme (CA); Omar Quraishi, Hudson (CA); Dominique P. Bridon, San Francisco, CA (US)

(73) Assignee: Conjuchem Biotechnologies Inc., Montreal, Quebec (CA)

Reexamination Request:
No. 90/010,913, Mar. 15, 2010

Reexamination Certificate for:
Patent No.: 7,307,148
Issued: Dec. 11, 2007
Appl. No.: 11/112,277
Filed: Apr. 22, 2005

Certificate of Correction issued May 13, 2008.

Related U.S. Application Data

(60) Provisional application No. 60/565,228, filed on Apr. 23, 2004.

(51) Int. Cl.
*A61K 47/42* (2006.01)
*A61K 47/48* (2006.01)
*B01D 15/08* (2006.01)
*B01D 15/16* (2006.01)
*B01D 15/32* (2006.01)
*C02K 1/00* (2006.01)
*C07K 1/20* (2006.01)
*C07K 14/765* (2006.01)
*C07K 19/00* (2006.01)
*C07D 14/76* (2006.01)

(52) U.S. Cl. ......................................... 530/364
(58) Field of Classification Search ................... 530/364
See application file for complete search history.

(56) References Cited

To view the complete listing of prior art documents cited during the proceeding for Reexamination Control Number 90/010,913, please refer to the USPTO's public Patent Application Information Retrieval (PAIR) system under the Display References tab.

*Primary Examiner* — Gary L. Kunz

(57) ABSTRACT

The present invention relates to a method for separating albumin conjugate from unconjugated albumin in a solution comprising albumin conjugate and unconjugated albumin by loading the solution onto a hydrophobic support equilibrated in aqueous buffer having a high salt content; applying to the support a gradient of decreasing salt concentration; and collecting the eluted albumin conjugate.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 10, 13 and 22 are cancelled.

Claims 1, 2, 11, 12, 14, 18, 23-25 and 28 are determined to be patentable as amended.

Claims 3-9, 15-17, 19-21, 26 and 27, dependent on an amended claim, are determined to be patentable.

New claims 29-46 are added and determined to be patentable.

1. A method for separating albumin *peptide* conjugate from unconjugated albumin in a solution comprising albumin *peptide* conjugate and unconjugated albumin, the method comprising:
   a) loading said solution onto a hydrophobic interaction chromatography matrix equilibrated in aqueous buffer at a salt concentration high enough to promote matrix-protein interactions;
   b) applying to said matrix a gradient of decreasing salt concentration; and
   c) collecting said albumin *peptide* conjugate, *wherein said peptide is covalently bonded to cysteine 34 of albumin.*

2. The method of claim 1, wherein said albumin *peptide* conjugate consists of a [molecule] *peptide* comprising a Michael acceptor covalently bonded to albumin.

11. The method of claim [10] *1*, wherein said [molecule] *peptide* is a peptide having a molecular weight of at least 57 daltons.

12. The method of claim [10] *1*, wherein said peptide is selected from the group consisting of glucagon like peptide 1 (GLP-1), atrial natriuretic peptide (ANP), kringle 5 [(KS)] (*K5*), dynorphin, exendin-4, growth hormone releasing factor (GRF), insulin, natriuretic peptides, enfuvirtide (T-20), T-1249, C-34, soluble C-35 peptide EK (SC-35), peptide YY (PYY), and analogs thereof.

14. The method of claim [10] *1*, wherein said [molecule] *peptide* is covalently attached to said albumin through an acid sensitive covalent bond or a peptide sequence susceptible to proteolytic cleavage, thereby allowing the separation of said [molecule] *peptide* and albumin and the entry of the [molecule] *peptide* into a cell.

18. The method of claim 1, wherein said gradient of decreasing salt concentration has a starting salt concentration of between [500 and 3000 mM] *about 750 and about 1700 mM*.

23. The method of claim 2, 3, or 4, wherein said [molecule is a] peptide [to which] *and* said Michael acceptor [is] *are* covalently bonded [, optionally] through a linker.

24. The method of claim 23, wherein said peptide is [an analog of] *selected from the group consisting of* glucagon like peptide 1 (GLP-1), glucagon like peptide 2 (GLP-2), atrial natriuretic peptide (ANP), kringle 5 [(KS)] (*K5*), dynorphin, exendin-4, growth hormone releasing factor (GRF), insulin, natriuretic peptides, enfuvirtide (T-20), T-1249, C-34, soluble C-35 peptide EK (SC-35), [or] peptide YY (PYY), *and analogs thereof*.

25. The method of claim 2, 3, or 4, wherein said [molecule] *peptide* is selected from the group consisting of GLP-1 (7-36) dAla$^8$ Lys$^{37}$ (ε-AEEA-MPA)-CONH$_2$ (SEQ ID No. 1), GRF (1-29) dAla$^2$ [Gin$^8$] *Gln$^8$* Ala$^{15}$ Leu$^{27}$ Lys$^{30}$ (ε-MPA) CONH$_2$ (SEQ ID No. 2), Ac-K5 Lys$^8$ (ε-MPA)-NH$_2$ (SEQ ID No. 3), Insulin B1-MPA (SEQ ID No. 4), Insulin A1-MPA (SEQ ID No. 5), MPA-AEEA-C34-CONH$_2$ (SEQ ID No. 6), C34 (1-34) Lys$^{35}$ (ε-AEEA-MPA)-CONH$_2$ (SEQ ID No. 7), C34 (1-34) Lys$^{13}$ (ε-AEEA-MPA)-CONH$_2$ (SEQ ID No. 8), GLP-1 (7-36) Lys$^{37}$ (ε-MPA)-NH$_2$ (SEQ ID No. 9), GLP-1 (7-36) dAla$^8$ Lys$^{37}$ (ε-MPA)-NH$_2$ (SEQ ID No. 10), GLP-1 (7-36) Lys$^{26}$ (ε-AEEA-AEEA-MPA) (SEQ ID No. 11), GLP-1 (7-36) Lys$^{34}$ (ε-AEEA-AEEA-MPA) (SEQ ID No. 12), Exendin-4-(1-39) Lys$^{40}$ (ε-MPA)-NH$_2$ (SEQ ID No. 13), Exendin-4 (9-39) Lys$^{40}$ (ε-AEEA-MPA)-CONH$_2$ (SEQ ID No. 14), Dyn A (1-13) (MPA)-NH$_2$ (SEQ ID No. 15), MPA-AEEA-ANP (99-126)-CONH$_2$ (SEQ ID No. 16), Dyn A (7-13) Lys$^{13}$ (ε-MPA)-CONH$_2$ (SEQ ID No. 17), acetyl-Phe-His-cyclohexylstatyl-lle-Lys (ε-AEEA-MPA)-CONH$_2$ (SEQ ID No. 18), GLP-1 (7-36) Lys$^{23}$ (ε-AEEA-MPA)-CONH$_2$ (SEQ ID No. 19), GLP-1 (7-36) Lys$^{18}$ (ε-AEEA-MPA)-CONH$_2$ (SEQ ID No. 20), GLP-1 (7-36) Lys$^{26}$ (ε-AEEA-MPA)-CONH$_2$ (SEQ ID No. 21), GLP-1 (7-37) Lys$^{27}$ (ε-AEEA-MPA)-CONH$_2$ (SEQ ID No. 22), GLP-1 (7-36) Lys$^{37}$ (ε-AEEA-AEEA-MPA)-CONH$_2$ (SEQ ID No. 23), GLP-1 (7-36) Lys$^{37}$ (ε-AEEA-MPA)-CONH$_2$ (SEQ ID No. 24), Exendin-4-(1-39) Lys$^{40}$ (ε-AEEA-MPA)-CONH$_2$ (SEQ ID No. 25), GLP-1 (7-36) Lys$^{34}$ (ε-AEEA-MPA)-CONH$_2$ (SEQ ID No. 26), Insulin B1-OA-MPA (SEQ ID No. 27), Insulin B29-MPA (SEQ ID No. 28), GRF (1-29) Lys$^{30}$ (ε-MPA)-CONH$_2$ (SEQ ID No. 29), GRF (1-29), dAla$^2$ Gln$^8$ dArg$^{11}$ Ala$^{15}$ Leu$^{27}$ Lys$^{30}$ (ε-MPA)-CONH$_2$ (SEQ ID No. 30), GRF (1-29) dAla$^2$ Lys$^{30}$ (ε-MPA)-CONH$_2$ (SEQ ID No. 31), GLP-1 (9-36) Lys$^{37}$ (ε-AEEA-MPA)-CONH$_2$ (SEQ ID No. 32), Ac-T20 (1-36) Lys$^{37}$ (ε-AEEA-MPA)-CONH$_2$ (SEQ ID No. 33), Ac-T1249 (1-39) Lys$^{40}$ (ε-AEEA-MPA)-CONH$_2$ (SEQ ID No. 34), 3',4'-didehydro-4'-deoxy-C'-norvincaleukoblastine -AEEA-MPA, C34 (1-34) Lys$^{13}$ (ε-MPA)-CONH$_2$ (SEQ ID No. 36), C34 (1-34) Lys$^{35}$ (ε-MPA)-CONH$_2$ (SEQ ID No. 37), MPA-C34 (1-34)-CONH$_2$ (SEQ ID No. 38), Ac-C34 (1-34) Glu$^2$ Lys$^6$ Lys$^7$ Glu$^9$ Glu$^{10}$ Lys$^{13}$ Lys$^{14}$ Glu$^{16}$ Glu$^{17}$ Lys$^{20}$ Lys$^{21}$ Glu$^{23}$ Glu$^{24}$ Lys$^{27}$ Glu$^{31}$ Lys$^+$Lys$^{35}$ Lys$^{36}$(ε-AEEA-MPA)-CONH$_2$ (SEQ ID No. 39), MPA-AEEA-C34 (1-34) Glu$^2$ Lys$^6$ Lys$^7$ Glu$^9$ Glu$^{10}$ Lys$^{13}$ Lys$^{14}$ Glu$^{16}$ Glu$^{17}$ Lys$^{21}$ Glu$^{23}$ Glu$^{24}$ Lys$^{27}$ Glu$^{31}$ Lys$^{34}$ Lys$^{35}$ CONH$_2$ (SEQ ID No. 40), PYY (3-36) Lys$^4$ (ε-OA-MPA)-CONH$_2$ (SEQ ID No. 41), MPA-OA-PPY (3-36)-CONH$_2$ (SEQ ID No. 42), Insulin B29-AEES2-MPA (SEQ ID No. 43), Insulin B1-AEES2-MPA (SEQ ID No. 44), Insulin B29-OA-MPA (SEQ ID No. 45), MPA-PYY (3-36)-CONH$_2$ (SEQ ID No. 46), PYY (3-36) Lys$^{37}$ (ε-MPA)-CONH$_2$ (SEQ ID No. 47), MPA-PYY (22-36)-CONH$_2$ (SEQ ID No. 48), Acetyl-PYY (22-36) Lys$^{37}$ (ε-MPA)-CONH$_2$ (SEQ ID No. 49), MPA-ANP (99-126)-CONH$_2$ (SEQ ID No. 50), MPA-EEEEP-ANP (99-126) (SEQ ID No. 51), and GLP-2 (1-33) Gly$^2$ Lys$^{34}$ (ε-MPA)-CONH$_2$ (SEQ ID No. 52).

28. The method of claim 2, 3, or 4, wherein said [molecule] *peptide* is GLP-1 (7-36) dAla$^8$ Lys$^{37}$ (ε-AEEA-MPA)-CONH$_2$.

29. The method of claim 1, wherein said albumin is selected from the group consisting of human albumin, rat albumin, mouse albumin, swine albumin, dog albumin, and rabbit albumin.

30. The method of claim 2, wherein said molecule is selected from the group consisting of a DNA, an RNA, and a combination of a peptide, a DNA, and an RNA, to which said Michael acceptor is covalently bonded, optionally through a linker.

31. The method of claim 1, wherein said aqueous buffer comprises sodium caprylate.

32. The method of claim 1, wherein said peptide is selected from the group consisting of glucagon like peptide 1 (GLP-1), atrial natriuretic peptide (ANP), kringle 5 (K5), dynorphin, C-34, insulin, and analogs thereof.

33. The method of claim 1, wherein said peptide is selected from the group consisting of growth hormone releasing factor (GRF), natriuretic peptides, enfuvirtide (T-20), T-1249, soluble C-35 peptide EK (SC-35), peptide YY (PYY), and analogs thereof.

34. The method of claim 1, wherein said peptide is exendin-4 or an analog thereof.

35. The method of claim 1, wherein the said salt is ammonium phosphate.

36. The method of claim 1, wherein said salt is magnesium phosphate.

37. A method for separating peptide-albumin conjugate from unconjugated albumin in a solution comprising peptide-albumin conjugate and unconjugated albumin, the method comprising:

a) loading said solution onto a hydrophobic interaction chromatography matrix equilibrated in aqueous buffer at a salt concentration high enough to promote matrix-protein interactions;

b) applying to said matrix a gradient of decreasing salt concentration; and c) collecting said peptide-albumin conjugate.

38. The method of claim 37, wherein said gradient of decreasing salt concentration has a starting salt concentration of between about 750 mM to about 1700 mM.

39. The method of claim 37, wherein said aqueous buffer comprises sodium caprylate.

40. The method of claim 37, wherein said peptide is covalently bonded to Cys34 of albumin.

41. The method of claim 37, wherein said albumin is human albumin.

42. The method of claim 37, wherein said albumin is serum albumin.

43. The method of claim 37, wherein said albumin is recombinant albumin.

44. The method of claim 37, wherein said hydrophobic interaction chromatography matrix is a column containing a hydrophobic resin.

45. The method of claim 44, wherein said hydrophobic resin is a bead-formed agarose-based gel filtration matrix covalently coupled to a ligand selected from the group consisting of an octyl group, a phenyl group, and a butyl group.

46. The method of claim 45, wherein said hydrophobic resin is a bead-formed agarose-based gel filtration matrix covalently coupled to a butyl group.

* * * * *

SEQUENCE LISTING

```
<160> NUMBER OF SEQ ID NOS: 53

<210> SEQ ID NO 1
<211> LENGTH: 31
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 2
<223> OTHER INFORMATION: Xaa is D-Ala
<220> FEATURE:
<221> NAME/KEY: MOD_RES
<222> LOCATION: 31
<223> OTHER INFORMATION: Xaa is Lys linked to AEEA-MPA

<400> SEQUENCE: 1

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Xaa
             20                  25                  30

<210> SEQ ID NO 2
<211> LENGTH: 30
<212> TYPE: PRT
<213> ORGANISM: Artificial Sequence
<220> FEATURE:
<223> OTHER INFORMATION: GRF Analogue
<220> FEATURE:
<221> NAME/KEY: MOD_RES
<222> LOCATION: 2
<223> OTHER INFORMATION: Xaa is Ala or D-Ala
<220> FEATURE:
<221> NAME/KEY: MOD_RES
<222> LOCATION: 30
<223> OTHER INFORMATION: Xaa is Lys linked to MPA

<400> SEQUENCE: 2

Tyr Xaa Asp Ala Ile Phe Thr Gln Ser Tyr Arg Lys Val Leu Ala Gln
```

```
                1               5                  10                 15
Leu Ser Ala Arg Lys Leu Leu Gln Asp Ile Leu Ser Arg Xaa
                20                  25                 30

<210> SEQ ID NO 3
<211> LENGTH: 8
<212> TYPE: PRT
<213> ORGANISM: Artificial Sequence
<220> FEATURE:
<223> OTHER INFORMATION: K5 Analogue
<220> FEATURE:
<221> NAME/KEY: MOD_RES
<222> LOCATION: 8
<223> OTHER INFORMATION: Xaa is Lys linked to MPA

<400> SEQUENCE: 3

Pro Arg Lys Leu Tyr Asp Tyr Xaa
1               5

<210> SEQ ID NO 4
<211> LENGTH: 30
<212> TYPE: PRT
<213> ORGANISM: Homo sapiens
<220> FEATURE:
<221> NAME/KEY: MOD_RES
<222> LOCATION: 1
<223> OTHER INFORMATION: Xaa is Phe linked to MPA

<400> SEQUENCE: 4

Xaa Val Asn Gln His Leu Cys Gly Ser His Leu Val Glu Ala Leu Tyr
1               5                  10                 15
Leu Val Cys Gly Glu Arg Gly Phe Phe Tyr Thr Pro Lys Thr
                20                  25                 30

<210> SEQ ID NO 5
<211> LENGTH: 21
<212> TYPE: PRT
<213> ORGANISM: Homo sapiens
<220> FEATURE:
<221> NAME/KEY: MOD_RES
<222> LOCATION: 1
<223> OTHER INFORMATION: Xaa is Gly linked to MPA

<400> SEQUENCE: 5

Xaa Ile Val Glu Gln Cys Cys Thr Ser Ile Cys Ser Leu Tyr Gln Leu
1               5                  10                 15
Glu Asn Tyr Cys Asn
                20

<210> SEQ ID NO 6
<211> LENGTH: 34
<212> TYPE: PRT
<213> ORGANISM: Artificial Sequence
<220> FEATURE:
<223> OTHER INFORMATION: C34 Analogue
<220> FEATURE:
<221> NAME/KEY: MOD_RES
<222> LOCATION: 1
<223> OTHER INFORMATION: Xaa is Trp linked to AEEA-MPA

<400> SEQUENCE: 6

Xaa Met Glu Trp Asp Arg Glu Ile Asn Asn Tyr Thr Ser Leu Ile His
1               5                  10                 15
Ser Leu Ile Glu Glu Ser Gln Asn Gln Gln Glu Lys Asn Glu Gln Glu
                20                  25                 30
Leu Leu
```

<210> SEQ ID NO 7
<211> LENGTH: 35
<212> TYPE: PRT
<213> ORGANISM: Artificial Sequence
<220> FEATURE:
<223> OTHER INFORMATION: C34 Analogue
<220> FEATURE:
<221> NAME/KEY: MOD_RES
<222> LOCATION: 35
<223> OTHER INFORMATION: Xaa is Lys linked to AEEA-MPA

<400> SEQUENCE: 7

Trp Met Glu Trp Asp Arg Glu Ile Asn Asn Tyr Thr Ser Leu Ile His
 1               5                  10                  15

Ser Leu Ile Glu Glu Ser Gln Asn Gln Gln Glu Lys Asn Glu Gln Glu
            20                  25                  30

Leu Leu Xaa
        35

<210> SEQ ID NO 8
<211> LENGTH: 34
<212> TYPE: PRT
<213> ORGANISM: Artificial Sequence
<220> FEATURE:
<223> OTHER INFORMATION: C34 Analogue
<220> FEATURE:
<221> NAME/KEY: MOD_RES
<222> LOCATION: 13
<223> OTHER INFORMATION: Xaa is Lys linked to AEEA-MPA

<400> SEQUENCE: 8

Trp Met Glu Trp Asp Arg Glu Ile Asn Asn Tyr Thr Xaa Leu Ile His
 1               5                  10                  15

Ser Leu Ile Glu Glu Ser Gln Asn Gln Gln Glu Lys Asn Glu Gln Glu
            20                  25                  30

Leu Leu

<210> SEQ ID NO 9
<211> LENGTH: 31
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 31
<223> OTHER INFORMATION: Xaa is Lys linked to MPA

<400> SEQUENCE: 9

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Xaa
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 2
<223> OTHER INFORMATION: Xaa is D-Ala
<220> FEATURE:
<221> NAME/KEY: MOD_RES
<222> LOCATION: 31
<223> OTHER INFORMATION: Xaa is Lys linked to MPA

<400> SEQUENCE: 10

His Xaa Glu Gly Thr Phe Thr Ser Asp Val Ser Ser Tyr Leu Glu Gly
 1               5                   10                  15

Gln Ala Ala Lys Glu Phe Ile Ala Trp Leu Val Lys Gly Arg Xaa
             20                  25                  30

<210> SEQ ID NO 11
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 20
<223> OTHER INFORMATION: Xaa is Lys linked to AEEA-AEEA-MPA

<400> SEQUENCE: 11

His Ala Glu Gly Thr Phe Thr Ser Asp Val Ser Ser Tyr Leu Glu Gly
 1               5                   10                  15

Gln Ala Ala Xaa Glu Phe Ile Ala Trp Leu Val Lys Gly Arg
             20                  25                  30

<210> SEQ ID NO 12
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 28
<223> OTHER INFORMATION: Xaa is Lys linked to AEEA-AEEA-MPA

<400> SEQUENCE: 12

His Ala Glu Gly Thr Phe Thr Ser Asp Val Ser Ser Tyr Leu Glu Gly
 1               5                   10                  15

Gln Ala Ala Lys Glu Phe Ile Ala Trp Leu Val Xaa Gly Arg
             20                  25                  30

<210> SEQ ID NO 13
<211> LENGTH: 40
<212> TYPE: PRT
<213> ORGANISM: Artificial Sequence
<220> FEATURE:
<223> OTHER INFORMATION: Exendin-4 Analogue
<220> FEATURE:
<221> NAME/KEY: MOD_RES
<222> LOCATION: 40
<223> OTHER INFORMATION: Xaa is Lys linked to MPA

<400> SEQUENCE: 13

His Gly Glu Gly Thr Phe Thr Ser Asp Leu Ser Lys Gln Met Glu Glu
 1               5                   10                  15

Glu Ala Val Arg Leu Phe Ile Glu Trp Leu Lys Asn Gly Gly Pro Ser
             20                  25                  30

Ser Gly Ala Pro Pro Pro Ser Xaa
         35                  40

<210> SEQ ID NO 14
<211> LENGTH: 32
<212> TYPE: PRT
<213> ORGANISM: Artificial Sequence

```
<220> FEATURE:
<223> OTHER INFORMATION: Exendin-4 Analogue
<220> FEATURE:
<221> NAME/KEY: MOD_RES
<222> LOCATION: 32
<223> OTHER INFORMATION: Xaa is Lys linked to AEEA-MPA

<400> SEQUENCE: 14

Asp Leu Ser Lys Gln Met Glu Glu Ala Val Arg Leu Phe Ile Glu
 1               5                  10                  15

Trp Leu Lys Asn Gly Gly Pro Ser Ser Gly Ala Pro Pro Ser Xaa
            20                  25                  30

<210> SEQ ID NO 15
<211> LENGTH: 13
<212> TYPE: PRT
<213> ORGANISM: Artificial Sequence
<220> FEATURE:
<223> OTHER INFORMATION: Dynorphin A Analogue
<220> FEATURE:
<221> NAME/KEY: MOD_RES
<222> LOCATION: 13
<223> OTHER INFORMATION: Xaa is Lys linked to MPA

<400> SEQUENCE: 15

Tyr Gly Gly Phe Leu Arg Arg Ile Arg Pro Lys Leu Xaa
 1               5                  10

<210> SEQ ID NO 16
<211> LENGTH: 28
<212> TYPE: PRT
<213> ORGANISM: Artificial Sequence
<220> FEATURE:
<223> OTHER INFORMATION: ANP Analogue
<220> FEATURE:
<221> NAME/KEY: MOD_RES
<222> LOCATION: 1
<223> OTHER INFORMATION: Xaa is Ser linked to AEEA-MPA

<400> SEQUENCE: 16

Xaa Leu Arg Arg Ser Ser Cys Phe Gly Gly Arg Met Asp Arg Ile Gly
 1               5                  10                  15

Ala Gln Ser Gly Leu Gly Cys Asn Ser Phe Arg Tyr
            20                  25

<210> SEQ ID NO 17
<211> LENGTH: 7
<212> TYPE: PRT
<213> ORGANISM: Artificial Sequence
<220> FEATURE:
<223> OTHER INFORMATION: Dynorphin A Analogue
<220> FEATURE:
<221> NAME/KEY: MOD_RES
<222> LOCATION: 7
<223> OTHER INFORMATION: Xaa is Lys linked to MPA

<400> SEQUENCE: 17

Arg Ile Arg Pro Lys Leu Xaa
 1               5

<210> SEQ ID NO 18
<211> LENGTH: 4
<212> TYPE: PRT
<213> ORGANISM: Artificial Sequence
<220> FEATURE:
<223> OTHER INFORMATION: ACE Inhibitor
<220> FEATURE:
<221> NAME/KEY: MOD_RES
<222> LOCATION: 2
```

```
<223> OTHER INFORMATION: Xaa is His linked to cyclohexylstatyl
<220> FEATURE:
<221> NAME/KEY: MOD_RES
<222> LOCATION: 4
<223> OTHER INFORMATION: Xaa is Lys linked to AEEA-MPA

<400> SEQUENCE: 18

Phe Xaa Ile Xaa
 1

<210> SEQ ID NO 19
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 17
<223> OTHER INFORMATION: Xaa is Lys linked to AEEA-MPA

<400> SEQUENCE: 19

His Ala Glu Gly Thr Phe Thr Ser Asp Val Ser Ser Tyr Leu Glu Gly
 1               5                  10                  15

Xaa Ala Ala Lys Glu Phe Ile Ala Trp Leu Val Lys Gly Arg
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 12
<223> OTHER INFORMATION: Xaa is Lys linked to AEEA-MPA

<400> SEQUENCE: 20

His Ala Glu Gly Thr Phe Thr Ser Asp Val Ser Xaa Tyr Leu Glu Gly
 1               5                  10                  15

Gln Ala Ala Lys Glu Phe Ile Ala Trp Leu Val Lys Gly Arg
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 20
<223> OTHER INFORMATION: Xaa is Lys linked to AEEA-MPA

<400> SEQUENCE: 21

His Ala Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Gly Arg
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: GLP-1 Analogue
<220> FEATURE:
```

```
<221> NAME/KEY: MOD_RES
<222> LOCATION: 21
<223> OTHER INFORMATION: Xaa is Lys linked to AEEA-MPA

<400> SEQUENCE: 22

His Ala Glu Gly Thr Phe Thr Ser Asp Val Ser Ser Tyr Leu Glu Gly
1               5                   10                  15

Gln Ala Ala Lys Xaa Phe Ile Ala Trp Leu Val Lys Gly Arg
            20              25                  30

<210> SEQ ID NO 23
<211> LENGTH: 31
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 31
<223> OTHER INFORMATION: Xaa is Lys linked to AEEA-AEEA-MPA

<400> SEQUENCE: 23

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20              25                  30

<210> SEQ ID NO 24
<211> LENGTH: 31
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 31
<223> OTHER INFORMATION: Xaa is Lys linked to AEEA-MPA

<400> SEQUENCE: 24

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20              25                  30

<210> SEQ ID NO 25
<211> LENGTH: 40
<212> TYPE: PRT
<213> ORGANISM: Artificial Sequence
<220> FEATURE:
<223> OTHER INFORMATION: Exendin-4 Analogue
<220> FEATURE:
<221> NAME/KEY: MOD_RES
<222> LOCATION: 40
<223> OTHER INFORMATION: Xaa is Lys linked to AEEA-MPA

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20              25                  30

Ser Gly Ala Pro Pro Pro Ser Xaa
            35                  40

<210> SEQ ID NO 26
<211> LENGTH: 31
<212> TYPE: PRT
```

```
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 28
<223> OTHER INFORMATION: Xaa is Lys linked to AEEA-MPA

<400> SEQUENCE: 26

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Gly Arg Lys
            20                  25                  30

<210> SEQ ID NO 27
<211> LENGTH: 30
<212> TYPE: PRT
<213> ORGANISM: Homo sapiens
<220> FEATURE:
<221> NAME/KEY: MOD_RES
<222> LOCATION: 1
<223> OTHER INFORMATION: Xaa is Phe linked to OA-MPA

<400> SEQUENCE: 27

Xaa Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30

<210> SEQ ID NO 28
<211> LENGTH: 30
<212> TYPE: PRT
<213> ORGANISM: Homo sapiens
<220> FEATURE:
<221> NAME/KEY: MOD_RES
<222> LOCATION: 29
<223> OTHER INFORMATION: Xaa is Lys linked to MPA

<400> SEQUENCE: 28

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Xaa Thr
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: GRF Analogue
<220> FEATURE:
<221> NAME/KEY: MOD_RES
<222> LOCATION: 30
<223> OTHER INFORMATION: Xaa is Lys linked to MPA

<400> SEQUENCE: 29

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Xaa
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: GRF Analogue
```

```
<220> FEATURE:
<221> NAME/KEY: MOD_RES
<222> LOCATION: 2
<223> OTHER INFORMATION: Xaa is D-Ala
<220> FEATURE:
<221> NAME/KEY: MOD_RES
<222> LOCATION: 11
<223> OTHER INFORMATION: Xaa is D-Arg
<220> FEATURE:
<221> NAME/KEY: MOD_RES
<222> LOCATION: 30
<223> OTHER INFORMATION: Xaa is Lys linked to MPA

<400> SEQUENCE: 30

Tyr Xaa Asp Ala Ile Phe Thr Gln Ser Tyr Xaa Lys Val Leu Arg Gln
 1               5                  10                  15

Leu Ser Ala Arg Lys Leu Leu Gln Asp Ile Leu Ser Arg Xaa
             20                  25                  30

<210> SEQ ID NO 31
<211> LENGTH: 30
<212> TYPE: PRT
<213> ORGANISM: Artificial Sequence
<220> FEATURE:
<223> OTHER INFORMATION: GRF Analogue
<220> FEATURE:
<221> NAME/KEY: MOD_RES
<222> LOCATION: 2
<223> OTHER INFORMATION: Xaa is D-Ala
<220> FEATURE:
<221> NAME/KEY: MOD_RES
<222> LOCATION: 30
<223> OTHER INFORMATION: Xaa is Lys linked to MPA

<400> SEQUENCE: 31

Tyr Xaa Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Xaa
             20                  25                  30

<210> SEQ ID NO 32
<211> LENGTH: 29
<212> TYPE: PRT
<213> ORGANISM: Artificial Sequence
<220> FEATURE:
<223> OTHER INFORMATION: GLP-1 Analogue
<220> FEATURE:
<221> NAME/KEY: MOD_RES
<222> LOCATION: 29
<223> OTHER INFORMATION: Xaa is Lys linked to AEEA-MPA

<400> SEQUENCE: 32

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg Xaa
             20                  25

<210> SEQ ID NO 33
<211> LENGTH: 37
<212> TYPE: PRT
<213> ORGANISM: Artificial Sequence
<220> FEATURE:
<223> OTHER INFORMATION: T20 Analogue
<220> FEATURE:
<221> NAME/KEY: MOD_RES
<222> LOCATION: 37
<223> OTHER INFORMATION: Xaa is Lys linked to AEEA-MPA

<400> SEQUENCE: 33
```

```
Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe Xaa
            35

<210> SEQ ID NO 34
<211> LENGTH: 40
<212> TYPE: PRT
<213> ORGANISM: Artificial Sequence
<220> FEATURE:
<223> OTHER INFORMATION: T1249 Analogue
<220> FEATURE:
<221> NAME/KEY: MOD_RES
<222> LOCATION: 40
<223> OTHER INFORMATION: Xaa is Lys linked to AEEA-MPA

<400> SEQUENCE: 34

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe Xaa
            35                  40

<210> SEQ ID NO 35
<211> LENGTH: 21
<212> TYPE: PRT
<213> ORGANISM: Homo sapiens

<400> SEQUENCE: 35

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 36
<211> LENGTH: 34
<212> TYPE: PRT
<213> ORGANISM: Artificial Sequence
<220> FEATURE:
<223> OTHER INFORMATION: C34 Analogue
<220> FEATURE:
<221> NAME/KEY: MOD_RES
<222> LOCATION: 13
<223> OTHER INFORMATION: Xaa is Lys linked to MPA

<400> SEQUENCE: 36

Trp Met Glu Trp Asp Arg Glu Ile Asn Asn Tyr Thr Xaa Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 37
<211> LENGTH: 35
<212> TYPE: PRT
<213> ORGANISM: Artificial Sequence
<220> FEATURE:
<223> OTHER INFORMATION: C34 Analogue
<220> FEATURE:
<221> NAME/KEY: MOD_RES
<222> LOCATION: 35
<223> OTHER INFORMATION: Xaa is Lys linked to MPA
```

```
<400> SEQUENCE: 37

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Xaa
        35

<210> SEQ ID NO 38
<211> LENGTH: 34
<212> TYPE: PRT
<213> ORGANISM: Artificial Sequence
<220> FEATURE:
<223> OTHER INFORMATION: C34 Analogue
<220> FEATURE:
<221> NAME/KEY: MOD_RES
<222> LOCATION: 1
<223> OTHER INFORMATION: Xaa is Trp linked to MPA

<400> SEQUENCE: 38

Xaa Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 39
<211> LENGTH: 36
<212> TYPE: PRT
<213> ORGANISM: Artificial Sequence
<220> FEATURE:
<223> OTHER INFORMATION: C34 Analogue
<220> FEATURE:
<221> NAME/KEY: MOD_RES
<222> LOCATION: 36
<223> OTHER INFORMATION: Xaa is Lys linked to AEEA-MPA

<400> SEQUENCE: 39

Trp Glu Glu Trp Asp Lys Lys Ile Glu Glu Tyr Thr Lys Lys Ile Glu
1               5                   10                  15

Glu Leu Ile Lys Lys Ser Glu Glu Gln Gln Lys Lys Asn Glu Glu Glu
            20                  25                  30

Leu Lys Lys Xaa
        35

<210> SEQ ID NO 40
<211> LENGTH: 35
<212> TYPE: PRT
<213> ORGANISM: Artificial Sequence
<220> FEATURE:
<223> OTHER INFORMATION: C34 Analogue
<220> FEATURE:
<221> NAME/KEY: MOD_RES
<222> LOCATION: 1
<223> OTHER INFORMATION: Xaa is Trp linked to MPA

<400> SEQUENCE: 40

Xaa Glu Glu Trp Asp Lys Lys Ile Glu Glu Tyr Thr Lys Lys Ile Glu
1               5                   10                  15

Glu Leu Ile Lys Lys Ser Glu Glu Gln Gln Lys Lys Asn Glu Glu Glu
            20                  25                  30

Leu Lys Lys
        35
```

```
<210> SEQ ID NO 41
<211> LENGTH: 34
<212> TYPE: PRT
<213> ORGANISM: Artificial Sequence
<220> FEATURE:
<223> OTHER INFORMATION: PYY Analogue
<220> FEATURE:
<221> NAME/KEY: MOD_RES
<222> LOCATION: 2
<223> OTHER INFORMATION: Xaa is Lys linked to OA-MPA

<400> SEQUENCE: 41

Ile Xaa Pro Glu Ala Pro Gly Glu Asp Arg Ser Pro Glu Glu Leu Asn
 1               5                  10                  15

Arg Tyr Tyr Lys Ser Leu Arg His Tyr Leu Asn Leu Val Thr Arg Gln
             20                  25                  30

Arg Tyr

<210> SEQ ID NO 42
<211> LENGTH: 34
<212> TYPE: PRT
<213> ORGANISM: Artificial Sequence
<220> FEATURE:
<223> OTHER INFORMATION: PYY Analogue
<220> FEATURE:
<221> NAME/KEY: MOD_RES
<222> LOCATION: 1
<223> OTHER INFORMATION: Xaa is Ile linked to OA-MPA

<400> SEQUENCE: 42

Xaa Lys Pro Glu Ala Pro Gly Glu Asp Arg Ser Pro Glu Glu Leu Asn
 1               5                  10                  15

Arg Tyr Tyr Lys Ser Leu Arg His Tyr Leu Asn Leu Val Thr Arg Gln
             20                  25                  30

Arg Tyr

<210> SEQ ID NO 43
<211> LENGTH: 30
<212> TYPE: PRT
<213> ORGANISM: Homo sapiens
<220> FEATURE:
<221> NAME/KEY: MOD_RES
<222> LOCATION: 29
<223> OTHER INFORMATION: Xaa is Lys linked to AEEAS-AEEAS-MPA

<400> SEQUENCE: 43

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Xaa Thr
             20                  25                  30

<210> SEQ ID NO 44
<211> LENGTH: 30
<212> TYPE: PRT
<213> ORGANISM: Homo sapiens
<220> FEATURE:
<221> NAME/KEY: MOD_RES
<222> LOCATION: 1
<223> OTHER INFORMATION: Xaa is Phe linked to AEEAS-AEEAS-MPA

<400> SEQUENCE: 44

Xaa Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
```

```
                     20                  25                  30

<210> SEQ ID NO 45
<211> LENGTH: 30
<212> TYPE: PRT
<213> ORGANISM: Homo sapiens
<220> FEATURE:
<221> NAME/KEY: MOD_RES
<222> LOCATION: 29
<223> OTHER INFORMATION: Xaa is Lys linked to OA-MPA

<400> SEQUENCE: 45

Phe Val Asn Gln His Leu Cys Gly Ser His Leu Val Glu Ala Leu Tyr
  1               5                  10                  15

Leu Val Cys Gly Glu Arg Gly Phe Phe Tyr Thr Pro Xaa Thr
                 20                  25                  30

<210> SEQ ID NO 46
<211> LENGTH: 34
<212> TYPE: PRT
<213> ORGANISM: Artificial Sequence
<220> FEATURE:
<223> OTHER INFORMATION: PYY Analogue
<220> FEATURE:
<221> NAME/KEY: MOD_RES
<222> LOCATION: 1
<223> OTHER INFORMATION: Xaa is Ile linked to MPA

<400> SEQUENCE: 46

Xaa Lys Pro Glu Ala Pro Gly Glu Asp Arg Ser Pro Glu Glu Leu Asn
  1               5                  10                  15

Arg Tyr Tyr Ala Ser Leu Arg His Tyr Leu Asn Leu Val Thr Arg Gln
                 20                  25                  30

Arg Tyr

<210> SEQ ID NO 47
<211> LENGTH: 35
<212> TYPE: PRT
<213> ORGANISM: Artificial Sequence
<220> FEATURE:
<223> OTHER INFORMATION: PYY Analogue
<220> FEATURE:
<221> NAME/KEY: MOD_RES
<222> LOCATION: 35
<223> OTHER INFORMATION: Xaa is Lys linked to MPA

<400> SEQUENCE: 47

Ile Lys Pro Glu Ala Pro Gly Glu Asp Arg Ser Pro Glu Glu Leu Asn
  1               5                  10                  15

Arg Tyr Tyr Ala Ser Leu Arg His Tyr Leu Asn Leu Val Thr Arg Gln
                 20                  25                  30

Arg Tyr Xaa
         35

<210> SEQ ID NO 48
<211> LENGTH: 15
<212> TYPE: PRT
<213> ORGANISM: Artificial Sequence
<220> FEATURE:
<223> OTHER INFORMATION: PYY Analogue
<220> FEATURE:
<221> NAME/KEY: MOD_RES
<222> LOCATION: 1
<223> OTHER INFORMATION: Xaa is Arg linked to MPA

<400> SEQUENCE: 48
```

```
Xaa Ser Leu Arg His Tyr Leu Asn Leu Val Thr Arg Gln Arg Tyr
1               5                   10                  15
```

<210> SEQ ID NO 49
<211> LENGTH: 16
<212> TYPE: PRT
<213> ORGANISM: Artificial Sequence
<220> FEATURE:
<223> OTHER INFORMATION: PYY Analogue
<220> FEATURE:
<221> NAME/KEY: MOD_RES
<222> LOCATION: 16
<223> OTHER INFORMATION: Xaa is Lys linked to MPA

<400> SEQUENCE: 49

```
Arg Ser Leu Arg His Tyr Leu Asn Leu Val Thr Arg Gln Arg Tyr Xaa
1               5                   10                  15
```

<210> SEQ ID NO 50
<211> LENGTH: 28
<212> TYPE: PRT
<213> ORGANISM: Artificial Sequence
<220> FEATURE:
<223> OTHER INFORMATION: ANP Analogue
<220> FEATURE:
<221> NAME/KEY: MOD_RES
<222> LOCATION: 1
<223> OTHER INFORMATION: Xaa is Ser linked to MPA

<400> SEQUENCE: 50

```
Xaa Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25
```

<210> SEQ ID NO 51
<211> LENGTH: 28
<212> TYPE: PRT
<213> ORGANISM: Artificial Sequence
<220> FEATURE:
<223> OTHER INFORMATION: ANP Analogue
<220> FEATURE:
<221> NAME/KEY: MOD_RES
<222> LOCATION: 1
<223> OTHER INFORMATION: Xaa is Ser linked to EEEEP-MPA

<400> SEQUENCE: 51

```
Xaa Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25
```

<210> SEQ ID NO 52
<211> LENGTH: 34
<212> TYPE: PRT
<213> ORGANISM: Artificial Sequence
<220> FEATURE:
<223> OTHER INFORMATION: GLP-2 Analogue
<220> FEATURE:
<221> NAME/KEY: MOD_RES
<222> LOCATION: 34
<223> OTHER INFORMATION: Xaa is Lys linked to MPA

<400> SEQUENCE: 52

```
His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30
```

```
Asp Xaa

<210> SEQ ID NO 53
<211> LENGTH: 30
<212> TYPE: PRT
<213> ORGANISM: Homo sapiens

<400> SEQUENCE: 53

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30
```